US012669511B2

(12) United States Patent
Adams et al.

(10) Patent No.: US 12,669,511 B2
(45) Date of Patent: Jun. 30, 2026

(54) METABOLITES AS DIAGNOSTICS FOR AUTISM SPECTRUM DISORDER IN CHILDREN WITH GASTROINTESTINAL SYMPTOMS

(71) Applicants:Arizona Board of Regents on Behalf of Arizona State University, Tempe, AZ (US); Rensselaer Polytechnic Institute, Troy, NJ (US)

(72) Inventors: James B. Adams, Tempe, AZ (US); Juergen Hahn, Troy, NY (US); Dae-Wook Kang, Tempe, AZ (US); Rosa Krajmalnik-Brown, Tempe, AZ (US)

(73) Assignees: Arizona Board of Regents on Behalf of Arizona State University, Tempe, AZ (US); Rensselaer Polytechnic Institute, Troy, NY (US)

( * ) Notice: Subject to any disclaimer, the term of this patent is extended or adjusted under 35 U.S.C. 154(b) by 1304 days.

(21) Appl. No.: 17/601,219

(22) PCT Filed: Apr. 6, 2020

(86) PCT No.: PCT/US2020/026910
§ 371 (c)(1),
(2) Date: Oct. 4, 2021

(87) PCT Pub. No.: WO2020/206443
PCT Pub. Date: Oct. 8, 2020

(65) Prior Publication Data
US 2022/0163538 A1      May 26, 2022

Related U.S. Application Data

(60) Provisional application No. 62/830,051, filed on Apr. 5, 2019.

(51) Int. Cl.
*G01N 33/68* (2006.01)

(52) U.S. Cl.
CPC ..... *G01N 33/6893* (2013.01); *G01N 2570/00* (2013.01); *G01N 2800/06* (2013.01); *G01N 2800/28* (2013.01)

(58) Field of Classification Search
CPC ........... G01N 33/6893; G01N 2570/00; G01N 2800/06; G01N 2800/28
See application file for complete search history.

(56) References Cited

U.S. PATENT DOCUMENTS

2013/0005806 A1   1/2013   Beaudet et al.
2015/0294081 A1*  10/2015  Geigenmuller ......... G16Z 99/00
                                                            702/19

(Continued)

FOREIGN PATENT DOCUMENTS

WO      2014/036182 A2    3/2014
WO      2014124166 A2     8/2014

(Continued)

OTHER PUBLICATIONS

Banerjee et al. (Hypothesis testing, type I and type II errors, Ind Psychiatry J, Jul.-Dec. 2009;18(2):127-131) (Year: 2009).*

(Continued)

*Primary Examiner* — Bao-Thuy L Nguyen
*Assistant Examiner* — Chau N.B. Tran
(74) *Attorney, Agent, or Firm* — Polsinelli PC

(57) ABSTRACT

Provided herein are metabolites and methods of using the metabolites for diagnosing and treating Autism Spectrum Disorder (ASD) in a subject with a gastrointestinal problem, for determining a personalized treatment protocol for the subject, and for monitoring the therapeutic effect of an ASD treatment protocol in the subject being treated with the ASD treatment protocol.

15 Claims, 32 Drawing Sheets

(56) References Cited

U.S. PATENT DOCUMENTS

2017/0067884 A1    3/2017  Srivastava et al.
2020/0061127 A1*   2/2020  Adams .................... A61K 35/66

FOREIGN PATENT DOCUMENTS

WO      2015006160 A2    1/2015
WO      2015157601 A1   10/2015
WO      2017172521 A1   10/2017
WO      2017197252 A1   11/2017
WO      2018089794 A1    5/2018
WO      2019046646 A1    3/2019

OTHER PUBLICATIONS

Agilent Technologies (Basics of LC/MS,2001) (Year: 2001).*
Yousri (Whole-exome sequencing identifies common and rare variant metabolic QTLs in a Middle Eastern population, Nature Communications vol. 9, Article No. 333 (2018)) (Year: 2018).*
Delaney (Metabolic profiles of exercise in patients with McArdle disease or mitochondrial myopathy, PNAS Aug. 1, 2017, vol. 114, No. 31) (Year: 2017).*
McFabe (Enteric short-chain fatty acids: microbial messengers of metabolism, mitochondria, and mind: implications in autism spectrum disorders, Microb Ecol Health Dis . May 29, 2015) (Year: 2015).*
ElBaz (Study of plasma amino acid levels in children with autism: An Egyptian sample, The Egyptian Journal of Medical Human Genetics (2014) 15, 181-186) (Year: 2014).*
Blusztajn (Levels of phospholipid catabolic intermediates, glycerophosphocholine and glycerophosphoethanolamine (1-(1-enyl-oleoyl)-GPE (p. 18:1)*), are elevated in brains of Alzheimer's disease but not of Down's syndrome patients, Brain Research (1990), 536(1-2), 240-4) (Year: 1990).*
Wang (Gastrointestinal microbiota and metabolite biomarkers in children with autism spectrum disorders, Biomarkers Med. (2014) 8 (3), 331-344) (Year: 2014).*
Manzi (Autism and Metabolic Diseases, Journal of Child Neurology / vol. 23, No. 3, Mar. 2008) (Year: 2008).*
Extended European Search Report issued in related application EP20781937.6 on Apr. 20, 2023, 10 pages.
West et al., Metabolomics as a Tool for Discovery of Biomarkers of Autism Spectrum Disorder in the Blood Plasma of Children, PLOS One, vol. 9, Issue 11, Nov. 2014, 13 pages.
Dieme et al., Metabolomics Study of Urine in Autism Spectrum Disorders Using a Multiplatform Analytical Methodology, Journal of Proteome Research 2015, 14, 5273-5282, 2015, 10 pages.
Yap et al., Urinary Metabolic Phenotyping Differentiates Children with Autism from Their Unaffected Siblings and Age-Matched Controls, Journal of Proteome Research 2010, 9, 2996-3004, 2010, 9 pages.
Nadal-Desbarats, Combined 1H-NMR and 1H-13C HSQC-NMR to improve urinary screening in autism spectrum disorders, Analyst, 2014, 139, 3460, 2014, 10 pages.
Srikantha et al., Microbiota-gut-brain-axis and Autism Spectrum Disorders, doi:10.20944/preprints201811.0171.v1, 2018, 30 pages.
Extended European Search Report issued in corresponding European Application No. 20783364.1 on Apr. 21, 2023, 9 pages.
Wang et al., Elevated Fecal Short Chain Fatty Acid and Ammonia Concentrations in Children with Autism Spectrum Disorder, Dig Dis Sci (2012) 57:2096-2202, 7 pages, 2012.
Abu-Akel et al., Mind the prevalence rate: overestimating the clinical utility of psychiatric diagnostic classifiers, Psychological Medicine, 48, 1225-1227, 3 pages, 2017.
Fein et al., Optimizing Outcome in Autism Spectrum Disorders, Policy Insights from the Behavioral and Brain Sciences vol. 4(1), 71-78, 2017.
Adams et al., Significant Association of Urinary Toxic Metals and Autism-Related Symptoms—A Nonlinear Statistical Analysis with Cross Validation, PLoS One 12(1), 24 pages, 2017.

Adams et al., Gastrointestinal flora and gastrointestinal status in children with autism-comparisons to typical children and correlation with autism severity, BMC Gastroenterology 2011, 11:22, 13 pages, 2011.
Fisher, The use of multiple measurements in taxonomic problems, The Annals of Human Genetics, 11 pages, 1936.
Fletcher-Watson et al., The potential of eye-tracking as a sensitive measure of behavioural change in response to intervention, Scientific Reports 8:14715, 7 pages, 2018.
French et al., Annual Research Review: Early intervention for infants and young children with, or at-risk of, autism spectrum disorder: a systematic review, The Journal of Child Psychology and Psychiatry, 59:4, 13 pages, 2018.
Frye et al., Approaches to studying and manipulating the enteric microbiome to improve autism symptoms, Microbial Ecology in Health and Disease, 15 pages, 2015.
Gaugler et al., Most genetic risk for autism resides with common variation, Nature Genetics, 7 pages, 204.
Holingue et al., Gastrointestinal Symptoms in Autism Spectrum Disorder: A Review of the Literature on Ascertainment and Prevalence, Autism Research 11:24-36 13 pages, 2018.
Howsmon et al., Classification and adaptive behavior prediction of children with autism spectrum disorder based upon multivariate data analysis of markers of oxidative stress and DNA methylation, PLoS Computational Biology 13(3):e1005385, 15 pages, 2017.
Howsmon et al., Multivariate techniques enable a biochemical classification of children with autism spectrum disorder versus typically-developing peers: A comparison and validation study, AIChE Bioengineering & Translational Medicine, 10 pages, 2018.
Kang et al., Microbiota Transfer Therapy alters gut ecosystem and improved gastrointestinal and autism symptoms: an open-label study, Microbiome 5:10, 16 pages, 2017.
Krajmalnik-Brown et al., Gut bacteria in children with autism spectrum disorders: challenges and promise of studying how a complex community influences a complex disease, Microbial Ecology in Health and Disease, 9 pages, 2015.
Li et al., The microbiota-gut-grain axis and its potential therapeutic role in autism spectrum disorder, Neuroscience 324: 131-139, 9 pages, 2016.
Mandy et al., Annual Research Review: The role of the environment in the developmental psychopathology of autism spectrum condition, Journal of Child Psychology and Psychiatry 57:3, 22 pages, 2016.
West et al., Metabolimics as a Tool for Discovery of Biomarkers of Autism Spectrum Disorder in the Blood Plasma of Children, PLoS One 9(11), 13 pages, 2014.
McPartland, Considerations in biomarker development for neurodevelopmental disorders, Curr Opin Neurol, 29(2), 9 pages, 2016.
Murias et al., Validation of Eye-Tracking Measure of Social Attention as a Potential Biomarker for Autism Clinical Trials, Autism Research 11:161-174, 9 pages, 2018.
Orinstein et al., Intervention History of Children and Adolescents with High-Functioning Autism and Optimal Outcomes, J Dev Behav Pediatr, 35(4): 247-256, 18 pages, 2014.
Pierce et al., To Screen or Not to Screen Universally for Autism is not the Question: Why the Task Force Got It Wrong, The Journal of Pediatrics, 13 pages, 2016.
Baio et al., Prevalence of Autism Spectrum Disorder Among Children Aged 8 Years—Autism and Developmental Disabilities Monitoring Network, 11 Sites, United States, 2014, Surveillance Summaries, 28 pages, 2014.
Ryberg, Evidence for the Implementation of the Early Start Denver Model for Young Children With Autism Spectrum Disorder, Journal of the American Psychiatric Nurses Associate, vol. 21(5) 327-337, 11 pages, 2015.
Soke et al., Prevalence of Co-occurring Medical and Behavioral Conditions/Symptoms Among 4- and 8-Year-Old Children with Autism Spectrum Disorder in Selected Areas of the United States in 2010, Journal of Autism and Developmental Disorders 48:2663-2676, 14 pages, 2018.
Vargason et al., On the Use of Multivariate Methods for Analysis of Data from Biological Networks, Processes, 11 pages, 2017.

(56)          References Cited

OTHER PUBLICATIONS

Vargason et al., Comparison of Three Clinical Trial Treatments for Autism Spectrum Disorder Through Multivariate Analysis of Changes in Metabolic Profiles and Adaptive Behavior, Frontiers in Cellular Neuroscience, vol. 12, Article 503, 15 pages, 2018.

Vargason et al., Gastrointestinal Symptoms and Oral Antibiotic Use in Children with Autism Spectrum Disorder: Retrospective Analysis of a Privately Insured U.S. Population, Journal of Autism and Developmental Disorders 49:647-659, 13 pages, 2019.

Vuong et al., Emerging Roles for the Gut Microbiome in Autism Spectrum Disorder, Society of Biological Psychiatry, 13 pages, 2017.

Yang et al., Brain responses to biological motion predict treatment outcome in young children with autism, Translational Psychiatry, 8 pages, 2016.

Zwaigenbaum et al., Stability of Diagnostic Assessment for Autism Spectrum Disorder between 18 and 36 Months in a High-Risk Cohort, Autism Research 9:790-800, 11 pages, 2016.

Kang et al., Fecal Microbiota Transplant Improved Gastrointestinal and Autism Symptoms by Changing the Gut Bacterial Community and Fecal Metabolites, ASM Microbe 2017, New Orleans, 14 pages, 2014.

Khemakhem et al., Novel biomarkers of metabolic dysfunction is autism spectrum disorder: potential for biological diagnostic markers, Metab Brain Dis 32:1983-1997, 15 pages, 2017.

International Search Report from related International Application No. PCT/US2020/026910, 15 pages, Jul. 31, 2020.

Hicks et al., Validation of a Salivary RNA Test for Childhood Autism Spectrum Disorder, Frontiers in Genetics, Nov. 2018, vol. 9, No. 534, pp. 1-11; abstract; p. 3, first column second paragraph; figure 2; p. 9, heading conclusion.

Metalmd, Technical Information Guide Inherited Metabolic Disorder Test, 2017 [retrieved May 21, 2020], retrieved from the internet: url: file:///U:/Downloads/Downloads/Meta_IMD_Technical_Information_Guide%20(2).pdf>; p. 2, heading test summary.

Office Action Article 94(3) for European Application No. 20783364.1, dated Jun. 3, 2024, (6 Pages).

Canadian Intellectual Property Office, Office Action, Application No. 3,136,301, Mar. 24, 2025, 5 pages.

Aoki, Y. et al., "Age-related change in brain metabolite abnormalities in autism: a meta-analysis of proton magnetic resonance spectroscopy studies", Translational Psychiatry, Jan. 17, 2012, 12 pages.

Canadian Intellectual Property Office, Office Action, Application No. 3,136,301, Mar. 20, 2026, 6 pages.

\* cited by examiner

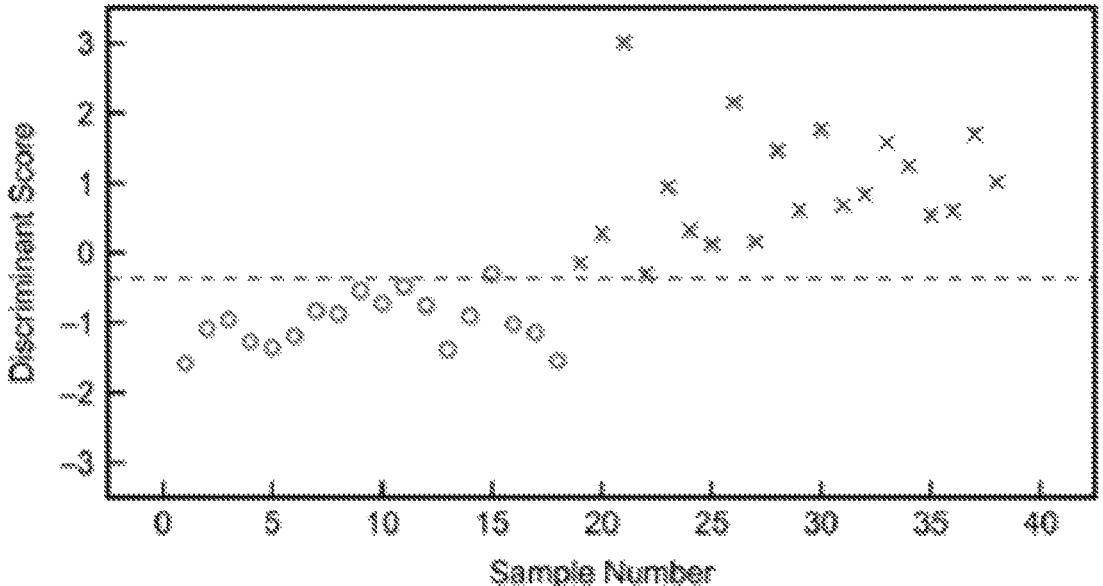
FIG. 11C
FIG. 11D

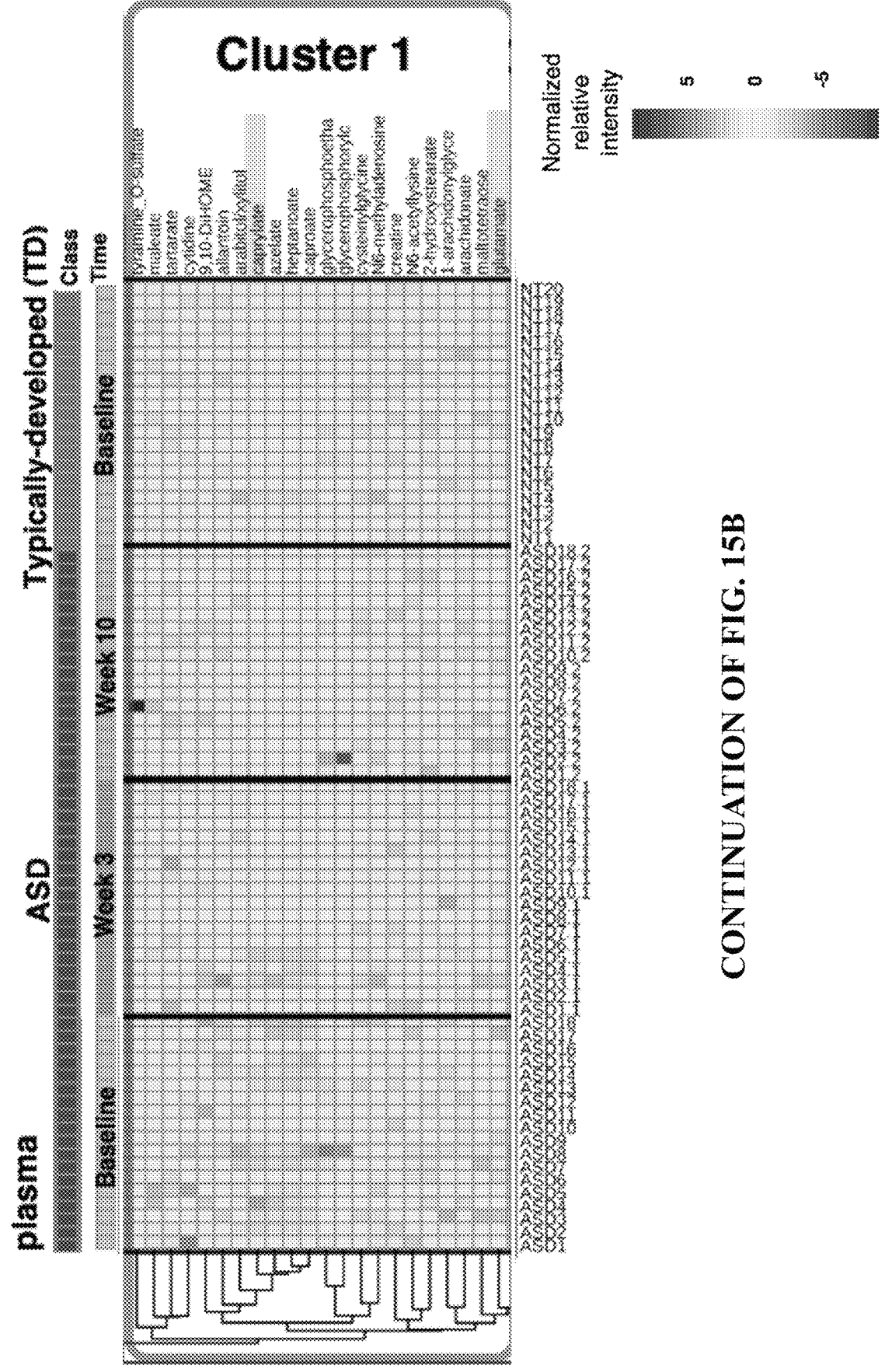
CONTINUATION OF FIG. 15B

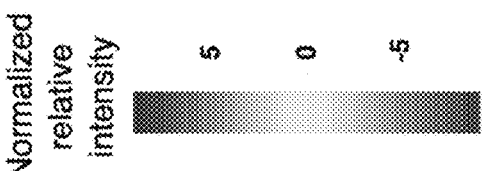
CONTINUATION OF FIG. 15B

METABOLITES AS DIAGNOSTICS FOR AUTISM SPECTRUM DISORDER IN CHILDREN WITH GASTROINTESTINAL SYMPTOMS

CROSS-REFERENCE TO RELATED APPLICATIONS

This application is a U.S. National Stage Application of International Application No. PCT/US2020/026910, filed Apr. 6, 2020, which claims priority from U.S. Provisional Patent Application No. 62/830,051, filed Apr. 5, 2019, the contents of all of which are incorporated herein by reference in their entirety.

FIELD OF THE INVENTION

The present disclosure generally relates to specific and sensitive methods for early detection of autism spectrum disorder (ASD) in a child, and more particularly to methods of diagnosing ASD in a subject with a gastrointestinal (GI) problem.

BACKGROUND

The diagnosis of autism spectrum disorder (ASD) is currently based on assessment of behavioral symptoms in patients considered to be at risk. Such symptoms include major impairments in social communication and skills, stereotyped motor behaviors, and tightly focused intellectual interests. Strong evidence exists that the underlying causes of ASD are present in earliest infancy and even prenatally, and involve a complex interaction of genetic and environmental factors. Yet diagnosis of ASD at early ages is extremely difficult because some symptoms are simply not present in early infancy, and other symptoms are difficult to distinguish from normal development. One national prevalence study of eight-year-olds with ASD found that the median age of diagnosis was 46 months for autism and 52 months for ASD; however, this study did not account for children and adults diagnosed at ages above eight years, so the true median age of diagnosis is even higher. Stable diagnoses of ASD have been found in children as young as 18 months, representing a significant disconnect between current and ideal outcomes.

At the same time, early diagnosis is important because available interventions are most effective if started early in life. A number of different intervention models have been demonstrated to be significantly helpful for many children with ASD, such as the Early Start Denver Model which has been found effective when started in early infancy. Early intervention may maximize the opportunity for improving neural connectivity while brain plasticity is still high, likely helping to reduce the severity of ASD or even prevent it from fully manifesting.

Even though ASD is currently diagnosed solely based upon clinical observations of children, certain physiological factors are believed to contribute or be affected by ASD. Development of a biomarker-based test for ASD, using quantifiable measures rather than qualitative judgement, could assist with screening for and diagnosing ASD earlier in childhood. This, in turn, would indicate if further evaluation is needed and allow for intervention and/or therapy to begin as early as possible. The value of ASD-related biomarkers goes beyond diagnosis, as they also offer the potential to evaluate treatment efficacy. This would serve as a complement to current behavioral and symptom assessments and help to further elucidate the underlying biological mechanisms affecting ASD symptoms. For example, multivariate statistical analysis of changes in plasma metabolites has been found to offer value for modeling changes in metabolic profiles and adaptive behavior resulting from clinical intervention. Functional neuroimaging biomarkers may also be promising indicators of biological response to treatment. In addition, eye-tracking metrics could represent further avenues for quantifying changes in behavior resulting from intervention and clinical trials. As with diagnostic biomarkers, such approaches can help to mitigate subjectivity in treatment assessment arising from the use of purely behavioral measures.

A need thus exists for efficient and reliable methods of early diagnosis of ASD in children, to indicate early intervention to prevent ASD and/or reduce the severity of symptoms.

SUMMARY OF THE INVENTION

One aspect of the present disclosure encompasses a method for diagnosing Autism Spectrum Disorder (ASD) in a subject with a gastrointestinal (GI) problem. The gastrointestinal problem can be constipation, diarrhea, or a combination of constipation and diarrhea.

The method comprises measuring the level of one or a combination of two or more metabolites selected from the metabolites listed in Tables 2, 3, 12, 18, 19, or 20 and any combination thereof, in a biological sample obtained from the subject. A level of the one or combination of metabolites in the biological sample significantly different from the level of the one or combination of metabolites in a control panel of metabolite levels obtained from typically developing (TD) individuals with no GI problems is indicative of a diagnosis of ASD with GI disorder.

The one or more metabolites can be measured by preparing a sample extract and using Ultrahigh Performance Liquid Chromatography-Tandem Mass Spectroscopy (UPLC-MS/MS) to obtain the levels of the one or more metabolites. A significantly different level of the one or combination of metabolites can be determined by applying each of the measured levels of the metabolites against a database of metabolite control measured levels created by measuring metabolite levels of the one or more metabolites in control TD individuals with no GI problems. The database can be stored on a computer system.

When the level of one metabolite is measured, applying the measured levels of the metabolites comprises computing a receiver operating characteristic (ROC) curve for each metabolite, and calculating the area under the ROC curve (AUROC). When the level of one metabolite is measured, an AUROC value of 0.7 or more is indicative of a diagnosis of ASD with GI disorder.

When the levels of a combination of two or more metabolites are measured, calculating the Type I (FPR; false positive rate) and Type II (FNR; false negative rate) errors for the combination of metabolites using FDA or logistic regression. When the levels of a combination of two or more metabolites are measured, a Type I error of about or below 10% and a Type II error of about or below 10% is indicative of a diagnosis of ASD with GI disorder.

Another aspect of the present disclosure encompasses a method for diagnosing ASD in a subject diagnosed with a GI problem. The method comprises obtaining or having obtained a biological sample from the subject, and preparing a sample extract. The method further comprises measuring the level of one or a combination of two or more metabolites selected from the metabolites listed in Tables 2, 3, 12, 18, 19, and 20 in the sample extract using Ultrahigh Performance Liquid Chromatography-Tandem Mass Spectroscopy (UHPLC-MS/MS). Each of the measured levels of the metabolites is applied against a database of metabolite control measured levels created by measuring metabolite levels of the one or more metabolites in control subjects with no history of bearing a child with ASD. The database is stored on a computer system.

When the level of one metabolite is measured, applying the measured levels of the metabolites comprises computing a receiver operating characteristic (ROC) curve for each metabolite, and calculating the area under the ROC curve (AUROC). When the level of one metabolite is measured, an AUROC value of 0.7 or more is indicative of a diagnosis of ASD with GI disorder.

When the levels of a combination of two or more metabolites are measured, calculating the Type I (FPR; false positive rate) and Type II (FNR; false negative rate) errors for the combination of metabolites using FDA or logistic regression. When the levels of a combination of two or more metabolites are measured, a Type I error of about or below 10% and a Type II error of about or below 10% is indicative of a diagnosis of ASD with GI disorder.

In any of the aspects described above, the level of a metabolite can be measured using reverse phase chromatography positive ionization methods optimized for hydrophilic compounds (LC/MS Pos Polar), reverse phase chromatography positive ionization methods optimized for hydrophobic compounds (LC/MS Pos Lipid), reverse phase chromatography with negative ionization conditions (LC/MS Neg); and, a HILIC chromatography method coupled to negative (LC/MS Polar).

The level of a metabolite can be calculated from a peak area and standard calibration curve obtained for the metabolite using the UPLC-MS/MS. Further, measuring can also comprise identifying each metabolite by automated comparison of the ion features in the sample extract to a reference library of chemical standard entries that included retention time, molecular weight (m/z), preferred adducts, and in-source fragments as well as associated MS spectra. The levels of metabolites associated with the metabolic abnormality can also be measured. The biological sample can comprise any one of synovial, whole blood, blood plasma, serum, urine, breast milk, and saliva.

In some aspects, the biological sample is blood plasma. When the biological sample is blood plasma, the level of one metabolite can be measured, and the metabolite can be selected from the metabolites in Table 4, Table 12, and Table 18. In some aspects, the level of a combination of two metabolites are measured. The two metabolites can be tyramine O-sulfate and inosine 5'-monophosphate. In other aspects, the levels of a combination of three metabolites are measured. The three metabolites are sarcosine, tyramine O-sulfate, and inosine 5'-monophosphate. Further, the sarcosine, tyramine O-sulfate, and inosine 5'-monophosphate metabolites can each represent a group of metabolites correlated with the metabolites. The group of metabolites correlated with sarcosine, tyramine O-sulfate, and inosine 5'-monophosphate metabolites can be as listed in Table 14. In other aspects, the levels of a combination of four metabolites are measured. The four metabolites are sarcosine, tyramine O-sulfate, inosine 5'-monophosphate, and arachidonate (20:4n6). In yet other aspects, the levels of a combination of five metabolites are measured. The five metabolites can be sarcosine, tyramine 0-sulfate, 1-arachidonoyl- GPI*(20:4)*, inosine 5'-monophosphate, and sphingomyelin (d18:2/23:0, d18:1/23:1, d17:1/24:1)*.

In some aspects, the biological sample is a fecal sample. When the biological sample is a fecal sample, the one or more metabolites can be selected from the metabolites in Table 5, 20, and 21. In some aspects, the metabolites can be imidazole propionate, indole, 2-hydroxy-3-methylvalerate, hydroxyproline, and theobromine.

The method can diagnose ASD in the subject with a sensitivity of at least about 80%, at least 90% or up to 100%, a specificity of at least about 80%, about 90%, or up to 100%, or both. In some aspects, the method diagnoses ASD in the subject with a sensitivity of about 94% and a specificity of about 100%. In other aspects, the method diagnoses ASD in the subject with a sensitivity of about 100% and a specificity of about 100%.

The method can further comprise assigning a medical, behavioral, and/or nutritional treatment protocol to the subject. A treatment protocol can be personalized to the subject. The treatment protocol can comprise restoring the level of one or more metabolites identified as being significantly different in the biological sample obtained from the subject when compared to the level of the one or more metabolites in the control panel of metabolite levels obtained from TD individuals. In some aspects, the treatment protocol comprises supplementation with sarcosine, tyramine O-sulfate, and combinations thereof. In other aspects, the treatment protocol comprises a fecal microbiota transplant. In one aspect, the fecal microbiota transplant restores the levels of sarcosine and tyramine O-sulfate in the subject.

Yet another aspect of the present disclosure encompasses a method of restoring the level of one or more metabolites identified as significantly different in a biological sample obtained from a subject with a GI problem having or at risk of having ASD to a level of the one or more metabolites in a the control panel of metabolite levels obtained from TD individuals. The method comprises administering to the subject an amount of a pharmaceutical composition comprising a fecal microbiota preparation. The one or more metabolites are sarcosine, IMP, or combinations thereof, or one or more metabolites correlated with sarcosine and IMP, wherein the one or more metabolites correlated with sarcosine and IMP are as listed in Table 14.

Another aspect of the present disclosure encompasses a method of determining a personalized treatment protocol for a subject with a GI problem having or at risk of having ASD. The method comprises measuring in a biological sample obtained from the subject the level of one or combination of two or more metabolites selected from the metabolites listed in Tables 2, 3, 12, 18, 19, and 20 and any combination thereof, identifying one or a combination of metabolites having a level in the biological sample significantly different from the level of the one or combination of metabolites in a control sample obtained from a typically developing subject with no GI problem, and assigning a personalized medical, behavioral, or nutritional treatment protocol to the subject, wherein a level of the one or combination of metabolites in the biological sample significantly different from the level of the one or combination of metabolites in the control sample is indicative of a diagnosis of ASD with GI disorder.

An additional aspect of the present disclosure encompasses a method of monitoring the therapeutic effect of an ASD treatment protocol in a subject with a GI problem having or at risk of having ASD. The method comprises measuring in a first biological sample obtained from the subject the level of one or a combination of metabolites selected from the metabolites listed in Tables 2, 3, 12, 18, 19, and 20 and any combination thereof, measuring in a second biological sample obtained from the subject the level of the one or combination of metabolites, and comparing the level of the one or combination of metabolites in the first sample and the second sample. Maintenance of the level of the one or combination of metabolites or a change of the level of the one or combination of metabolites to a level of the one or combination of metabolites in a control sample is indicative that the treatment protocol is therapeutically effective in the subject. The treatment protocol can be fecal matter transplant.

Yet another aspect of the present disclosure encompasses a kit for performing the method of any one of the methods described above. The kit comprises: (a) a container for collecting the biological sample from the subject; (b) solutions and solvents for preparing an extract from a biological sample obtained from the subject; and (c) instructions for (i) preparing the extract, (ii) measuring the level of one or more metabolites selected from the metabolites listed in Tables 2, 3, 12, 18, 19, and 20 using Ultrahigh Performance Liquid Chromatography-Tandem Mass Spectroscopy (UPLC-MS/MS); and (iii) applying the measured metabolite levels against a database of metabolite control values created by measuring metabolite levels in TD individuals with no GI problems.

BRIEF DESCRIPTION OF THE DRAWINGS

FIG. 11C. FDA using the best combination of three metabolites. Cross-validated scores.

FIG. 11D. FDA using the best combination of three metabolites. Confusion matrix from cross-validation based on classification with the shown threshold.

FIG. 17A. Correlation between sulfate reducing *Desulfovibrio* and sulfate levels (Spearman correlation, p<0.005).

FIG. 17A. Correlation between and p-cresol sulfate and sulfate level. (Spearman correlation, p<0.005).

FIG. 18. Possible metabolic features that Microbiota Transfer Therapy (MTT) induced for the improvement on gastrointestinal and behavioral symptoms in children with ASD.

DETAILED DESCRIPTION

Figure 1:
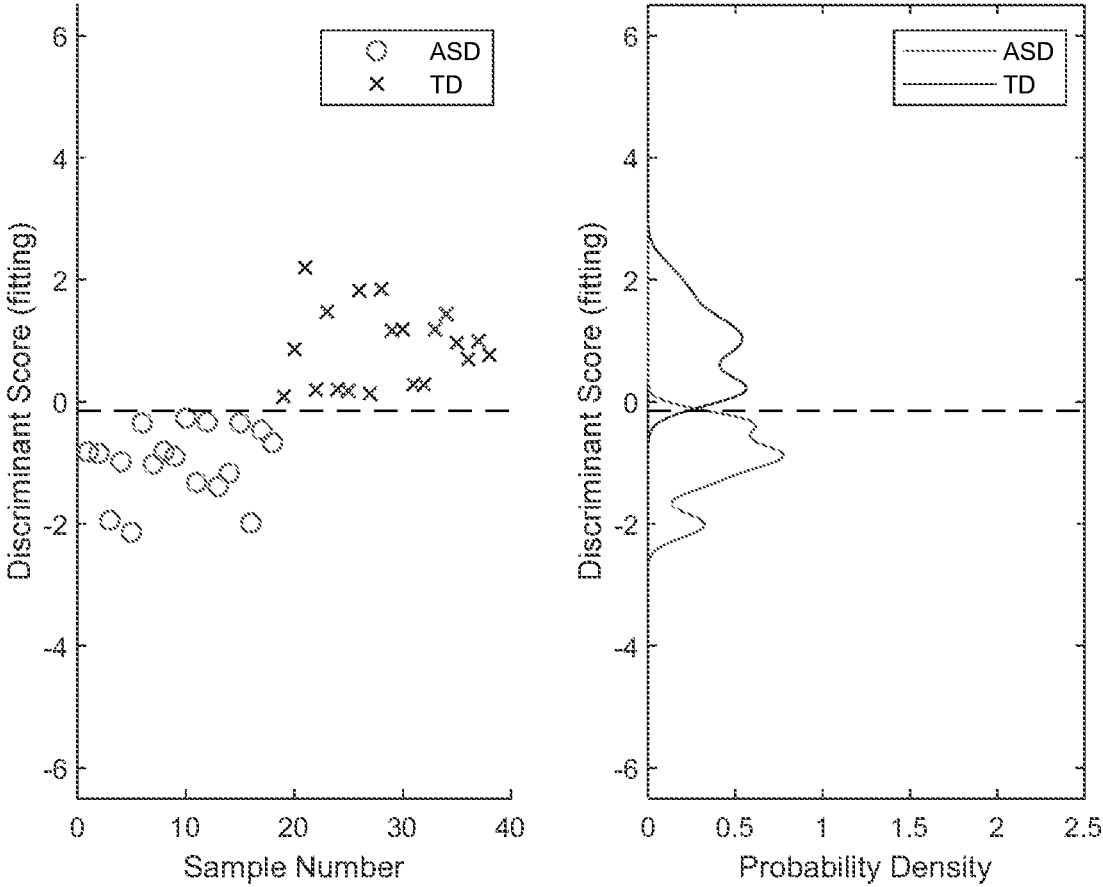
FIG. 1. Fitting results of plasma metabolites inosine 5'-monophosphate (IMP), valylglycine, 1-(1-enyl-oleoyl)-GPE (P-18:1)*, gamma-glutamylglutamate. Type I error: 3.3% and Type II error: 4.0%.

The present disclosure is based in part on the surprising discovery of metabolite biomarkers measured in a biological sample obtained from a subject with a gastrointestinal problem and methods of using the biomarkers to Autism Spectrum Disorder (ASD) in the subject. Using the methods described herein, the metabolites can be used to diagnose ASD with a surprising level of specificity and sensitivity approaching 100%.

I. Methods

One aspect of the present disclosure provides a method of diagnosing ASD by measuring the level of metabolites in a biological sample obtained from a subject. The subject can be, without limitation, a human, a non-human primate, a mouse, a rat, a guinea pig, and a dog. In some aspects, the subject is a human subject. The subject can be a premature newborn, a term newborn, a neonate, an infant, a toddler, a young child, a child, an adolescent, a pediatric patient, a geriatric patient. In one aspect, the subject is a child patient below about 18, 15, 12, 10, 8, 6, 4, 3, 2, or 1 year old. In another aspect, the subject is an adult patient. In another aspect, the subject is an elderly patient. In another aspect, the subject is about between 1 and 5, between 2 and 10, between 3 and 18, between 21 and 50, between 21 and 40, between 21 and 30, between 50 and 90, between 60 and 90, between 70 and 90, between 60 and 80, or between 65 and 75 years old.

In one aspect, the subject has a gastrointestinal (GI) problem. Beyond its core symptoms, ASD is also associated with a number of co-occurring conditions that contribute to significant heterogeneity in clinical manifestations of the disorder. GI problems are one such group of conditions that are common in children with ASD and are strongly correlated with more severe ASD-related symptoms. Non-limiting examples of GI problems of the subject include constipation, diarrhea, irritable bowel syndrome, hemorrhoids, anal fissures, perianal abscesses, anal fistula, diverticular disease, colon polyps and cancer, colitis such as ulcerative colitis, Crohn's disease, ischemic colitis, and radiation colitis. In some aspects, the subject has a GI problem selected from diarrhea, constipation, or combination thereof.

A sample may include but is not limited to, a cell, a cellular organelle, an organ, a tissue, a tissue extract, a biofluid, or an entire organism. The sample may be a heterogeneous or homogeneous population of cells or tissues. As such, metabolite levels or concentrations can be measured within cells, tissues, organs, or other biological samples obtained from the subject. For instance, the biological sample can be bone marrow extract, whole blood, blood plasma, serum, peripheral blood, urine, phlegm, synovial fluid, milk, saliva, mucus, sputum, exudates, cerebrospinal fluid, intestinal fluid, cell suspensions, tissue digests, tumor cell containing cell suspensions, cell suspensions, and cell culture fluid which may or may not contain additional substances (e.g., anticoagulants to prevent clotting). The sample can comprise cells or can be cell free. Samples that include cells comprises metabolites that exist primarily inside of cells as well as those that primarily exist outside of cells. In some aspects, the sample is a fecal sample. In another aspect, the sample is a plasma sample.

In some aspects, multiple biological samples may be obtained for diagnosis by the methods of the present invention, e.g., at the same or different times. A sample, or samples obtained at the same or different times, can be stored and/or analyzed by different methods.

Methods for obtaining and extracting the metabolome from a wide range of biological samples, including cell cultures, urine, blood/serum, and both animal- and plant-derived tissues are known in the art. Although these protocols are readily available, the variable stability of metabolites and the source of a sample means that even minor changes in procedure can have a major impact on the observed metabolome. For instance, the fast turnover rate of enzymes and the variable temperature and chemical stability of metabolites require that metabolomics samples be collected quickly and handled uniformly and that all enzymatic activity be rapidly quenched in order to minimize biologically irrelevant deviations between samples that may result from the processing protocol.

In some aspects, multiple biological samples may be obtained for diagnosis by the methods of the present invention, e.g., at the same or different times. A sample, or samples obtained at the same or different times, can be stored and/or analyzed by different methods.

A metabolomics extraction protocol can focus on a subset of metabolites (for example, water-soluble metabolites or lipids). Furthermore, an extraction protocol may focus on either a highly reproducible and quantitative extraction of a restricted set of metabolites (targeted metabolomics) or the global collection of all possible metabolites (untargeted metabolomics). As such, the extraction protocols can and will vary depending on the metabolites, number of metabolites to be measured, and the biological sample in which the metabolites are measured, among other variables, and can be determined experimentally.

Methods of measuring the level of metabolites in a sample are known, and can and will vary depending on the metabolites, the number of metabolites to be measured, and the biological sample in which the metabolites are measured, among other variables, and can be determined experimentally. Such concentration can be expressed in many ways including, for example, the number of molecules per unit weight or unit volume, and the relative ratio between the levels of two metabolites, wherein optionally, one of the two metabolites is a control metabolite that substantially maintains its levels regardless of any treatment. Metabolite abundance or levels may be identified using, for example, Mass Spectrometry such as MALDI/TOF (time-of-flight), SELDI/TQF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, Ultrahigh Performance Liquid Chromatography-Tandem Mass Spectroscopy (UPLC-MS/MS), tandem mass spectrometry (e.g., MS/MS, MS/MS/MS, ESI-MS MS etc.), secondary ion mass spectrometry (SIMS), and/or ion mobility spectrometry (e.g. GC-FMS, FMS-MS, LC-FMS, LC-FMS-MS among others), enzyme assays, and variations on these methods. In some aspects, the metabolites are measured using Ultrahigh Performance Liquid Chromatography-Tandem Mass Spectroscopy (UPLC-MS/MS).

In some aspects, a sample extract is subjected to one or more than one measurement. For instance, a sample can be divided into more than one aliquot to measure metabolites using more than one analytical method, each directed to measure of a group of metabolites with similar characteristics. In some aspects, the level of metabolites in aliquots of the sample extract are measured using reverse phase chromatography positive ionization methods optimized for hydrophilic compounds (LC/MS Pos Polar); reverse phase chromatography positive ionization methods opti-mized for hydrophobic compounds (LC/MS Pos Lipid); reverse phase chromatography with negative ionization conditions (LC/MS Neg); and a HILIC chromatography method coupled to negative (LC/MS Polar).

The level of a metabolite can be determined from a peak area and standard calibration curve obtained for the metabolite using the UPLC-MS/MS. Additionally, measuring metabolites can further include identifying each metabolite such as by automated comparison of the ion features in the sample extract to a reference library of chemical standard entries that include retention time, molecular weight (m/z), preferred adducts, and in-source fragments as well as associated MS spectra.

In one aspect, the method comprises measuring the level of one, or a combination of two or more metabolites in the sample. For instance, the level of one or the levels of 2, 3, 4, 5, 6, 7, 8, 9, 10, 15, 20, 25, 30, 40, 50, 60 or more metabolites can be measured. The metabolites and combinations of metabolites can be selected from the metabolites listed in Tables 2, 3, 12, 18, 19, and 20.

As shown and described in further detail in the examples, a level of the measured one or combination of metabolites in the biological sample significantly different from the level of the one or combination of metabolites in a control panel of metabolite levels, is diagnostic of ASD. A significantly different level of the one or combination of metabolites can be determined by applying each of the measured levels of the metabolites against a database of metabolite control measured levels created by measuring metabolite levels of the one or more metabolite in control subjects with no history of bearing a child with ASD. The database can be stored on a computer system. It is noted that a significant difference in the level of the metabolite can be an increase or a decrease in the level of the metabolite in the sample when compared to the level of the metabolite in the control panel of metabolite levels. When the levels of a combination of two or more metabolites are measured, a multivariate analysis can further be combined with leave-one-out cross-validation to analyze the success of the model on classification.

In some aspects, the level of one metabolite is measured. When the level of one metabolite is measured, applying each of the measured levels of the metabolites can comprise comparing the measured level of the metabolite in the sample to the level of the metabolite in the control panel of metabolite levels using a statistical analysis method. Non-limiting examples of statistical analysis methods suitable for use when one metabolite is measured include analysis of variance (ANOVA), chi-squared test, correlation, factor analysis, Mann-Whitney U, Mean square weighted deviation (MSWD), Pearson product-moment correlation coefficient, regression analysis, Spearman's rank correlation coefficient, Student's t-test, Time series analysis, and Conjoint Analysis, among others, and combinations thereof. In some aspects, when the level of one metabolite is measured, applying each of the measured levels of the metabolites can comprise computing a receiver operating characteristic (ROC) curve for the metabolite, and calculating the area under the ROC curve (AUROC). In general, AUROC values range from about 0.5 to 1, wherein a higher number indicates a more significant result. An AUROC value of about 0.7 or more can be indicative of a diagnosis of ASD with GI disorder. In some aspects, an AUROC value of about 0.8, 0.9, or above is indicative of a diagnosis of ASD with GI disorder.

In other aspects, when the level of one metabolite is measured, p-values are calculated using nonparametric statistical tests with Mann-Whitney U-test, Wilcoxon signed-rank test, Spearman correlation test, and KW sum-rank test. In yet other aspects, when the level of one metabolite is measured, p values are adjusted by correcting for multiple hypotheses with Benjamini-Hochberg and Leave-One-Out methods. In some aspects, a p-value of less than or about 0.05 is indicative of a diagnosis of ASD with GI disorder.

In some aspects, when paired data (before and after MTT treatment in the same participants) is compared, the Wilcoxon signed-rank test and 1-tailed test is employed.

In some aspects, the level of a combination of two or more metabolites in a plasma sample is measured. When the levels of a combination of two or more metabolites are measured, applying each of the measured levels of the metabolites against a database of metabolite control measured levels created by measuring metabolite levels of the one or more metabolite in control TD subjects with no GI problems comprises calculating the Type I (FPR; false positive rate) and Type II (FNR; false negative rate) errors for the combination of metabolites using FDA or logistic regression. A Type I error of about or below 25, 20, 15, or about 10% and a Type II error of about or below 25, 20, 15, or 10% is indicative of a diagnosis of ASD with GI disorder.

The one or combination of metabolites can be measured in a fecal sample obtained from a subject. In some aspects, the metabolites in the fecal sample are selected from the metabolites in Table 5, 20, and 21. In one aspect, the one or more metabolites can be are imidazole propionate, indole, p-cresol sulfate, tyramine O-sulfate, 4-hydrophenylacetate, 2-hydroxy-3-methylvalerate, hydroxyproline, and theobromine.

Metabolites can also be measured in a plasma sample obtained from the subject. In some aspects, the level of one metabolite in a plasma sample is measured. When the level of one metabolite is measured in a plasma sample to diagnose ASD, the metabolite can be selected from the metabolites listed in Table 4, Table 12, and Table 18. Alternatively, when the level of one metabolite is measured in a plasma sample, the metabolite can be glutamate, tyramine O-sulfate, indolepropionate, biliverdin, nicotinamide riboside, caprylate (with 8 carbon atoms; C8), heptanoate (C7), inosine 5'-monophosphate (IMP), sarcosine, methylsuccinate, valylglycine, leucylglycine, galactonate, iminodiacetate, caprylate, heptanoate, or bilirubin. In some aspects, when the level of one metabolite is measured in a plasma sample, the metabolite is sarcosine, methylsuccinate, nicotinamide riboside, IMP, valylglycine, or iminodiacetate. In some aspects, the level of a combination of two metabolites are measured to diagnose ASD. The two metabolites can be tyramine O-sulfate and inosine 5'-monophosphate. In other aspects, the level of a combination of three metabolites are measured to diagnose ASD. The three metabolites can be sarcosine, tyramine O-sulfate, and inosine 5'-monophosphate.

In some aspects, the levels of a combination of four metabolites are measured in a plasma sample. The four metabolites can be sarcosine, tyramine O-sulfate, inosine 5'-monophosphate, and arachidonate (20:4n6). In other aspects, the levels of a combination of five metabolites are measured. The five metabolites can be sarcosine, tyramine O-sulfate, 1-arachidonoyl-GPI* (20:4)*, inosine 5'-mono-phosphate, and sphingomyelin (d18:2/23:0, d18:1/23:1, d17:1/24:1)*.

Further, more than one combination of metabolites can be used to further improve the accuracy of an ASD diagnosis, including improving specificity and sensitivity, and reducing misclassification errors. For instance, the diagnosis obtained from a measurement of a combination of two metabolites in a fecal sample can be combined with results from a combination of three metabolites measured in a blood plasma sample to improve accuracy of a diagnosis.

Further, each metabolite can represent a group of metabolites correlated with the metabolite. In the methods, the levels of metabolites correlated with each metabolite can also be measured.

The method can diagnose ASD with a surprisingly high level of sensitivity. For instance, the method can diagnose ASD in a subject with a sensitivity greater than or equal to 90%, greater than or equal to 91%, greater than or equal to 92%, greater than or equal to 93%, greater than or equal to 94%, greater than or equal to 95%, greater than or equal to 96%, greater than or equal to 97%, greater than or equal to 98%, greater than or equal to 99%, or even with a 100% sensitivity. The method can also diagnose ASD with a surprisingly high level of specificity. For instance, the method can diagnose ASD in a subject with a specificity greater than or equal to 90%, greater than or equal to 91%, greater than or equal to 92%, greater than or equal to 93%, greater than or equal to 94%, greater than or equal to 95%, greater than or equal to 96%, greater than or equal to 97%, greater than or equal to 98%, greater than or equal to 99%, or even with a 100% specificity. In some aspects, the method can diagnose ASD with a specificity of at least about 80% to 90%, a specificity of at least about 80% to 90%, or both. In one aspect, the method can diagnose ASD with a specificity and sensitivity of 100%.

The method can diagnose ASD with a low misclassification error, such as a misclassification error of about 10, 8, 9, 7, 6, 5, 4, 3, 2, or about 1% or even with no misclassification error. In some aspects, the method can diagnose ASD with a misclassification error of about 5% or less, or about 3% or less. Further, the method can diagnose ASD with an accuracy of about 75, 80, 85, 90, 95% or with about 100% accuracy. In some aspects, the method can diagnose ASD with an accuracy of about 95% or higher, such as with an accuracy of about 97% or with about 100% accuracy.

The method can further comprise assigning a medical, behavioral, and/or nutritional treatment protocol to the subject when the subject is diagnosed with ASD. Non-limiting examples of treatment protocols include behavioral management therapy, cognitive behavior therapy, early intervention, educational and school-based therapies, joint attention therapy, medication treatment, nutritional therapy, occupational therapy, parent-mediated therapy, physical therapy, social skills training, speech-language therapy, and combinations thereof. Non-limiting examples of medication treatment include antipsychotic drugs, such as risperidone and aripripazole, for treating irritability associated with ASD, selective serotonin re-uptake inhibitors (SSRIs), tricyclics, psychoactive or anti-psychotic medications, stimulants, anti-anxiety medications, anticonvulsants, nutritional supplementation, and Microbiota Transfer Therapy (MTT).

In one aspect, the treatment protocol is supplementation with the metabolite. The metabolite can be supplemented by nutritional means, or by oral or parenteral administration of compositions comprising the metabolite. In one aspect, the treatment protocol is MTT. As GI symptoms can be due to perturbed gut microbiome homeostasis in individuals with ASD, with the resulting metabolic abnormalities possibly contributing to altered GI and nervous system function, correcting its abnormalities could alleviate the symptoms of ASD and its co-occurring conditions. MTT comprises transfer of purified gut bacteria from a healthy person to the subject. Methods of performing MTT are known in the art and can be as described in, e.g., Kang, et al. "Microbiota Transfer Therapy alters gut ecosystem and improves gastrointestinal and autism symptoms: An open-label study." Microbiome 5(1): 10 (2017), the disclosure of which is incorporated herein in its entirety. (Hereinafter referred to as "Kang et al.").

Treatment protocols can comprise restoring the level of one or more metabolite identified as significantly different in the biological sample obtained from the subject to a level of the one or more metabolites in the control panel of metabolite levels obtained from TD individuals with no GI problems. Similarly, when a metabolite represents a group of metabolites correlated with the metabolite, the treatment protocol can comprise restoring the level of one or more of the group of metabolites associated with the identified metabolite. The level of a metabolite can be restored by about 20%, 30%, 40%, 50%, 60%, 70%, 80%, 90% or more.

In some aspects, a treatment protocol restores levels of sarcosine, indolepropionate, IMP, bilirubin, biliverdin, methylsuccinate, nicotinamide riboside, IMP, valylglycine, iminodiacetate, or combinations thereof, or one or more metabolite correlated with sarcosine and IMP by supplementing with the one or more metabolite. In other aspects, a treatment protocol reduces levels of glutamate, heptanoate, p-cresol sulfate, dopamine, or combinations thereof, or one or more metabolite correlated with the one or more metabolite.

In other aspects, the one or more of sarcosine, glutamate, indolepropionate, IMP, methylsuccinate, nicotinamide riboside, caprylate, heptanoate, IMP, valylglycine, iminodiacetate, p-cresol sulfate, dopamine, and metabolites correlated with sarcosine and IMP are restored by MTT. In some aspects, MTT treatment increases the levels of *Desulfovibrio*. Metabolites correlated with sarcosine and IMP can be as listed in Table 14.

A treatment protocol can be personalized to the subject. For instance, a treatment protocol can be personalized based on the metabolites found to be significantly different in a sample obtained from the subject when compared to a control and identified using the method described herein. Such a personalized treatment protocol can include adjusting in the subject the level of the one or combination of metabolites found to be identified as being significantly different in the biological sample obtained from the subject to a level of the one or more metabolites in the control panel of metabolite levels obtained from TD individuals. The treatment protocol can also include adjusting the levels of one or more metabolite associated with the one or combination of two or more metabolites identified as having a level in the biological sample significantly different from the level of the one or combination of metabolites in the control sample.

Another aspect of the present disclosure encompasses a method for diagnosing ASD in a subject diagnosed with a GI problem. The method comprises obtaining or having obtained a biological sample from the subject, and preparing a sample extract. T method further comprises measuring the level of one or a combination of two or more metabolites selected from the metabolites listed in Tables 2, 3, 12, 18, 19, and 20 in the sample extract using Ultrahigh Performance Liquid Chromatography-Tandem Mass Spectroscopy (UHPLC-MS/MS). Each of the measured levels of the metabolites is applied against a database of metabolite control measured levels created by measuring metabolite levels of the one or more metabolite in control subjects with no history of bearing a child with ASD. The database is stored on a computer system.

When the level of one metabolite is measured, applying the measured levels of the metabolites comprises computing a receiver operating characteristic (ROC) curve for each metabolite, and calculating the area under the ROC curve (AUROC). When the level of one metabolite is measured, an AUROC value of 0.7 or more is indicative of a diagnosis of ASD with GI disorder.

When the levels of a combination of two or more metabolites are measured, calculating the Type I (FPR; false positive rate) and Type II (FNR; false negative rate) errors for the combination of metabolites using FDA or logistic regression. When the levels of a combination of two or more metabolites are measured, a Type I error of about or below 10% and a Type II error of about or below 10% is indicative of a diagnosis of ASD with GI disorder.

Yet another aspect of the present disclosure encompasses a method of restoring the level of one or more metabolite identified as significantly different in a biological sample obtained from a subject with a GI problem having or at risk of having ASD to a level of the one or more metabolite in a the control panel of metabolite levels obtained from TD individuals. The method comprises administering to the subject an amount of a pharmaceutical composition comprising a fecal microbiota preparation. The one or more metabolite is sarcosine, IMP, or combinations thereof, or one or more metabolite correlated with sarcosine and IMP, wherein the one or more metabolite correlated with sarcosine and IMP are listed in as listed in Table 14.

Another aspect of the present disclosure encompasses a method of determining a personalized treatment protocol for a subject with a GI problem having or at risk of having ASD. The method comprises measuring in a biological sample obtained from the subject the level of one or combination of two or more metabolites selected from the metabolites listed in Tables 2, 3, 12, 18, 19, and 20 and any combination thereof, identifying one or a combination of metabolites having a level in the biological sample significantly different from the level of the one or combination of metabolites in a control sample obtained from a typically developing subject with no GI problem, and assigning a personalized medical, behavioral, or nutritional treatment protocol to the subject, wherein a level of the one or combination of metabolites in the biological sample significantly different from the level of the one or combination of metabolites in the control sample is indicative of a diagnosis of ASD with GI disorder. The treatment protocol can be fecal matter transplant.

An additional aspect of the present disclosure encompasses a method of monitoring the therapeutic effect of an ASD treatment protocol in a subject with a GI problem having or at risk of having ASD. The method comprises measuring in a first biological sample obtained from the subject the level of one or a combination of metabolites selected from the metabolites listed in Tables 2, 3, 12, 18, 19, and 20 and any combination thereof, measuring in a second biological sample obtained from the subject the level of the one or combination of metabolites, and comparing the level of the one or combination of metabolites in the first sample and the second sample. Maintenance of the level of the one or combination of metabolites or a change of the level of the one or combination of metabolites to a level of the one or combination of metabolites in a control sample is indicative that the treatment protocol is therapeutically effective in the subject. The treatment protocol can be fecal matter transplant.

The methods provided herein result in, or are aimed at achieving a detectable improvement in one or more indicators or symptoms of ASD in a subject at risk of having ASD. The one or more indicators or symptoms of ASD include, without limitation, changes in eye tracking, skin conductance and/or EEG measurements in response to visual stimuli, difficulties engaging in and responding to social interaction, verbal and nonverbal communication problems, repetitive behaviors, intellectual disability, difficulties in motor coordination, attention issues, sleep disturbances, and physical health issues such as gastrointestinal disturbances.

Several screening instruments are known in the art for evaluating a subject's social and communicative development and thus can be used as aids in screening for and detecting changes in the severity of impairment in communication skills, social interactions, and restricted, repetitive, and stereotyped patterns of behavior characteristic of autism spectrum disorder. Evaluation can include neurologic and genetic assessment, along with in-depth cognitive and language testing. Additional measures developed specifically for diagnosing and assessing autism include the Autism Diagnosis Interview-Revised (ADI-R), the Autism Diagnostic Observation Schedule (ADOS-G) and the Childhood Autism Rating Scale (CARS).

According to CARS, evaluators rate the subject on a scale from 1 to 4 in each of 15 areas: Relating to People; Imitation; Emotional Response; Body Use; Object Use; Adaptation to Change; Visual Response; Listening Response; Taste, Smell, and Touch Response and Use; Fear; Verbal Communication; Nonverbal Communication; Activity; Level an Consistency of Intellectual Response; and General Impressions. A second edition of CARS, known as the Childhood Autism Rating Scale-2 or CARS-2, was developed by Schopler et al. (Childhood Autism Rating Scale Second edition (CARS2): Manual. The original CARS was developed primarily with individuals with co-morbid intellectual functioning and was criticized for not accurately identifying higher functioning individuals with ASD. CARS-2 retained the original CARS form for use with younger or lower functioning individuals (now renamed the CARS2-ST for "Standard Form"), but also includes a separate rating scale for use with higher functioning individuals (named the CARS2-HF for "High Functioning") and an unscored information-gathering scale ("Questionnaire for Parents or Caregivers" or CARS2-QPC) that has utility for making CARS2ST and CARS2-HF ratings.

Another symptom-rating instrument useful for assessing changes in symptom severity before, during, or following treatment according to a method provided herein is the Aberrant Behavior Checklist (ABC). The ABC is a symptom rating checklist used to assess and classify problem behaviors of children and adults in a variety of settings. The ABC includes 58 items that resolve onto five subscales: (1) irritability/agitation, (2) lethargy/social withdrawal, (3) stereotypic behavior, (4) hyperactivity/noncompliance, and (5) inappropriate speech.

II. Kits

An additional aspect of the present disclosure encompasses a kit for performing the method of any one of the methods described above. The kit comprises: (a) a container for collecting the biological sample from the subject; (b)

solutions and solvents for preparing an extract from a biological sample obtained from the subject; and (c) instructions for (i) preparing the extract, (ii) measuring the level of one or more metabolites selected from the metabolites listed in Tables 2, 3, 12, 18, 19, and 20 using Ultrahigh Performance Liquid Chromatography-Tandem Mass Spectroscopy (UPLC-MS/MS); and (iii) applying the measured metabolite levels against a database of metabolite control values created by measuring metabolite levels in TD individuals with no GI problems.

As used herein, "kits" refer to a collection of elements including at least one non-standard laboratory reagent for use in the disclosed methods, in appropriate packaging, optionally containing instructions for use. A kit may further include any other components required to practice the methods, such as dry powders, concentrated solutions, or ready-to-use solutions. In some aspects, a kit comprises one or more containers that contain reagents for use in the methods. Containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

A kit may include instructions for testing a biological sample of a subject with a GI problem having or at risk of having ASD. The instructions will generally include information about the use of the kit in the disclosed methods. In other aspects, the instructions may include at least one of the following: description of possible therapies including therapeutic agents; clinical studies; and/or references. The instructions may be printed directly on the container (when present), or as a label applied to the container, or as a separate sheet, pamphlet, card, or folder supplied in or with the container.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

As used herein, a "fecal microbe" refers to a microbe that can be found in fecal matter. A "fecal microbe preparation" refers to a collection of fecal microbes.

As used herein, a "microbiota" and "flora" refer to a community of microbes that live in or on a subject's body, both sustainably and transiently, including eukaryotes, archaea, bacteria, and viruses (including bacterial viruses (i.e., phage)).

A "fecal microbiota" or "fecal microbiota preparation" refers to a community of microbes present in or prepared from a subject's feces. A non-selected fecal microbiota refers to a community or mixture of fecal microbes derived from a donor's fecal sample without selection and substantially resembling microbial constituents and population structure found in such fecal sample.

As various changes could be made in the above-described metabolites and methods without departing from the scope of the invention, it is intended that all matter contained in the above description and in the examples given below, shall be interpreted as illustrative and not in a limiting sense.

EXAMPLES

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The publications discussed throughout are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1: Identification and Characterization of Metabolites Associated with ASD Plasma and fecal metabolites from 18 children with ASD and 20 control plasma and fecal samples neurotypical children that underwent fecal microbiota transplant (FMT) treatment. The levels of 621 plasma and 669 fecal metabolites were measured. First, it was demonstrated that 75 individual metabolites measured in plasma had two-tailed Mann-Whitney U test p values lower than 0.05, and a set of 10 plasma metabolites were significantly different (q<0.10) after using False Discovery Methods to eliminate false positives.

Combinations of up to 5 plasma or fecal metabolites were then analyzed to identify the combinations with the highest sensitivity and specificity. For plasma measurements, the most promising diagnostic test involved four metabolites: inosine 5'-monophosphate (IMP), valylglycine, 1-(1-enyl-oleoyl)-GPE (P-18:1)*, and gamma-glutamylglutamate.

For the results of the top 4 combinations of plasma metabolites, the ASD cohort was further evaluated during FMT treatment (3-weeks and 10-weeks). The treatment resulted in significant improvements in gastrointestinal and autism symptoms. Before treatment the groups could be easily distinguished with the FDA tests, but after treatment the groups were much more similar, and the test was much less able to distinguish the two groups. This suggests that the Fisher discriminant analysis FDA test as described herein for autism is also a potential biomarker to monitor the effectiveness of treatment interventions.

For fecal metabolites, it was demonstrated that 5 fecal metabolites (imidazole propionate, indole, 2-hydroxy-3-methylvalerate, hydroxyproline, and theobromine) could differentiate the two groups with >90% sensitivity and specificity. The ASD cohort was further evaluated at each time point (3-weeks, 10-weeks, and 18-weeks). The FDA test was much less able to distinguish the ASD and neurotypical groups after treatment, suggesting the combination of those 5 fecal metabolites as a potential biomarker to monitor the effectiveness of treatment interventions.

More detailed results are included in Examples 2-4 below. Methods used are as detailed in Example 5.

Leave-one-out cross-validation was used to determine the best combination to ensure that the results are not just fitted well, but that they are statistically independent. In short, cross-validation leaves out a sample, then determines the best combination of the remaining samples, and finally tests this best combination on the sample that was left out. After this the sample is put back into the dataset and a different sample is removed, whereupon the entire procedure is repeated. This process continues until each sample has been left out one time. This cross-validation procedure ensures that the best combination is chosen, not just from fitting the results but from predicting results for the samples which were left out.

In short, a small set of 4-5 metabolites can be used to differentiate between young children with ASD and young TD children, with a high sensitivity and specificity. These results are novel because they are the first metabolomics-based comparisons of children with ASD and TD. These metabolites are also useful to monitor the effectiveness of treatment interventions.

Example 2: Sample Collection

Plasma and fecal samples were collected from children with ASD and neurotypical children. For children with ASD, multiple samples were collected in the course of fecal microbiota treatment (FMT) therapy. After collection, samples were frozen in a −80° C. freezer. Once all samples were collected from all patients, they were sent together to Metabolon on dry ice. All samples were tested together in one batch, because the test is only semi-quantitative, i.e., the test measures relative, not absolute, differences between the samples. Also, all the samples were collected during the same time period, so the difference in storage times between the two groups was small, which also helps to minimize differences since even at −80° C. there is a small degradation of sample quality (estimated at 2%/year).

To ensure high-quality plasma samples, all plasma samples were collected in the morning after an overnight fast, and were processed rapidly and then frozen in dry ice, and then placed in a −80° C. freezer within 24 hours.

To ensure high-quality stool samples, all samples were collected at the participant's home and placed in their home freezer within 15 minutes of collection. Samples were then collected from participants' homes within 3 days, transported on dry ice, and stored at −80° C. until processed.

Example 3: Search for the Most Significant Individual Metabolites

The measurements of the levels of individual metabolites were evaluated using a rich statistical approach. Two data sets describing changes in plasma and fecal metabolites over the course of MTT treatment were obtained. These treatment data are for 18 children with ASD who have GI issues. A control group consisted of 20 typically developing (TD) children who did not have GI issues (and who did not undergo treatment).

Four primary time points were measured in the study. Blood and fecal samples were collected from ASD participants at baseline (Week 0), after the initial major dose of MTT (Week 3), after the end of maintenance MTT treatment (Week 10), and after an eight-week observation period (Week 18). Samples were not collected for all participants at all time points (Table 1). TD controls were only evaluated at Week 0 and Week 18.

TABLE 1

| Sample Type | Cohort | Week 0 | Week 3 | Week 10 | Week 18 |
|---|---|---|---|---|---|
| Fecal | ASD | 18 | 17 | 18 | 18 |
| | TD | 20 | 0 | 0 | 14 |
| Plasma | ASD | 18 | 18 | 18 | 0 |
| | TD | 20 | 0 | 0 | 0 |

First, the appropriate approach to use for individual metabolites was determined: Univariate analysis was performed using hypothesis testing to test for differences between the population median of each group of children (18 children with autism spectrum disorder and 20 neurotypical children). Because of a small sample size that does not have normal distribution, the Mann-Whitney U test was performed. Then, False Discovery Rate (FDR) methods were used to correct for multiple-hypothesis testing. Out of 621 identified plasma metabolites, this resulted in 75 plasma metabolites that had two-tailed Mann-Whitney U test p values lower than 0.05, and a set of 10 plasma metabolites had two-tailed $p<0.05$ and FDR<0.1. (Table 2). For fecal metabolites, 669 fecal metabolites were identified, and two-tailed Mann-Whitney U test resulted in 26 metabolites with two-tailed p values lower than 0.05 (Table 3). All 26 metabolites, however, were FDR>0.1.

TABLE 2

| Most Significant Plasma Metabolites. | | | | | |
|---|---|---|---|---|---|
| BIOCHEMICAL | SUPER_PATHWAY | SUB_PATHWAY | P-value | FDR | Fold Change |
| nicotinamide_riboside | Cofactors and Vitamins | Nicotinate and Nicotinamide Metabolism | <0.001 | 0.022 | −2.60 |
| HEPES | Xenobiotics | Chemical | <0.001 | 0.022 | −3.76 |
| inosine_5'Smonophosphate_(IMP) | Nucleotide | Purine Metabolism, (Hypo)Xanthine/Inosine containing | <0.001 | 0.022 | −3.75 |
| iminodiacetate_(IDA) | Xenobiotics | Chemical | <0.001 | 0.030 | −4.02 |
| methylsuccinate | Amino Acid | Leucine, Isoleucine and Valine Metabolism | <0.001 | 0.030 | −13.72 |

TABLE 2-continued

Most Significant Plasma Metabolites.

| BIOCHEMICAL | SUPER_PATHWAY | SUB_PATHWAY | P-value | FDR | Fold Change |
|---|---|---|---|---|---|
| galactonate | Carbohydrate | Fructose, Mannose and Galactose Metabolism | <0.001 | 0.031 | −2.95 |
| valylglycine | Peptide | Dipeptide | <0.001 | 0.041 | −3.25 |
| sarcosine | Amino Acid | Glycine, Serine and Threonine Metabolism | 0.001 | 0.041 | −3.75 |
| leucylglycine | Peptide | Dipeptide | 0.001 | 0.041 | −3.64 |
| caprylate_(8:0) | Lipid | Medium Chain Fatty Acid | 0.001 | 0.045 | −3.10 |
| heptanoate_(7:0) | Lipid | Medium Chain Fatty Acid | 0.001 | 0.053 | −4.07 |
| 1-palmitoyl-GPI*_(16:0)* | Lipid | Lysolipid | 0.002 | 0.105 | −1.28 |
| 3-phosphoglycerate | Carbohydrate | Glycolysis, Gluconeogenesis, and Pyruvate Metabolism | 0.002 | 0.107 | −3.79 |
| azelate_(nonanedioate;_C9) | Lipid | Fatty Acid, Dicarboxylate | 0.003 | 0.132 | −3.70 |
| N6-acetyllysine | Amino Acid | Lysine Metabolism | 0.004 | 0.132 | −3.43 |
| 1-stearoyl-GPS_(18:0)* | Lipid | Lysolipid | 0.004 | 0.132 | −1.53 |
| EDTA | Xenobiotics | Chemical | 0.004 | 0.132 | −2.61 |
| caproate_(6:0) | Lipid | Medium Chain Fatty Acid | | 0.142 | −4.07 |
| 1-arachidonoyl-GPI*_(20:4)* | Lipid | Lysolipid | | 0.142 | −1.99 |
| 1-(1-enyl-oleoyl)-GPE_(P-18:1)* | Lipid | Lysoplasmalogen | 0.005 | 0.162 | −1.57 |
| 2-aminophenol_sulfate | Xenobiotics | Chemical | 0.006 | 0.163 | −5.21 |
| 1-methylimidazoleacetate | Amino Acid | Histidine Metabolism | 0.006 | 0.163 | −2.12 |
| glycerophosphoethanolamine | Lipid | Phospholipid Metabolism | 0.006 | 0.163 | −1.21 |
| 2-methylserine | Amino Acid | Glycine, Serine and Threonine Metabolism | 0.007 | 0.163 | −5.54 |
| 10-undecenoate_(11:1n1) | Lipid | Medium Chain Fatty Acid | 0.007 | 0.163 | −1.19 |
| biliverdin | Cofactors and Vitamins | Hemoglobin and Porphyrin Metabolism | 0.007 | 0.163 | −2.94 |
| indolepropionate | Amino Acid | Tryptophan Metabolism | 0.007 | 0.172 | 2.19 |
| citrate | Energy | TCA Cycle | 0.010 | 0.207 | −1.35 |
| 1-oleoyl-GPS_(18:1) | Lipid | Lysolipid | 0.010 | 0.207 | −1.18 |
| bilirubin | Cofactors and Vitamins | Hemoglobin and Porphyrin Metabolism | 0.011 | 0.218 | −4.43 |
| tiglyl_carnitine_(C5) | Amino Acid | Leucine, Isoleucine and Valine Metabolism | 0.011 | 0.220 | −1.80 |
| propionylglycine_(C3) | Lipid | Fatty Acid Metabolism (also BCAA Metabolism) | 0.011 | 0.220 | −7.03 |
| tyramine_O-sulfate | Amino Acid | Phenylalanine and Tyrosine Metabolism | 0.012 | 0.220 | 0.55 |
| picolinate | Amino Acid | Tryptophan Metabolism | 0.012 | 0.220 | −4.61 |
| 5,6-dihydrothymine | Nucleotide | Pyrimidine Metabolism, Thymine containing | 0.012 | 0.220 | −2.02 |
| 1-stearoyl-GPI_(18:0) | Lipid | Lysolipid | 0.013 | 0.226 | −1.21 |
| 21-hydroxypregnenolone_disulfate | Lipid | Steroid | 0.013 | 0.226 | −1.51 |
| cysteinylglycine | Amino Acid | Glutathione Metabolism | 0.016 | 0.252 | −1.18 |
| 2-hydroxystearate | Lipid | Fatty Acid, Monohydroxy | 0.016 | 0.252 | −5.23 |

TABLE 2-continued

Most Significant Plasma Metabolites.

| BIOCHEMICAL | SUPER_PATHWAY | SUB_PATHWAY | P-value | FDR | Fold Change |
|---|---|---|---|---|---|
| 1-arachidonylglycerol_(20:4) | Lipid | Monoacylglycerol | 0.017 | 0.260 | −1.56 |
| 3-methoxycatechol_sulfate_(1) | Xenobiotics | Benzoate Metabolism | 0.017 | 0.260 | 1.65 |
| sphingomyelin_(d18:2/23:0,_d18:1/ 23:1,_d17:1/Lipid | Sphingolipid Metabolism | 0.018 | 0.261 | −3.29 | |
| creatine | Amino Acid | Creatine Metabolism | 0.020 | 0.265 | −1.89 |
| cys-gly,_oxidized | Amino Acid | Glutathione Metabolism | 0.020 | 0.265 | −2.43 |
| gamma-glutamylhistidine | Peptide | Gamma-glutamyl Amino Acid | 0.020 | 0.265 | −3.40 |
| maltotetraose | Carbohydrate | Glycogen Metabolism | 0.020 | 0.265 | −1.25 |
| 9,10-DiHOME | Lipid | Fatty Acid, Dihydroxy | 0.020 | 0.265 | −3.00 |
| S-1-pyrroline-5-carboxylate | Amino Acid | Glutamate Metabolism | 0.022 | 0.275 | −3.81 |
| fructose | Carbohydrate | Fructose, Mannose and Galactose Metabolism | 0.022 | 0.275 | −1.31 |
| cinnamoylglycine | Xenobiotics | Food Component/Plant | 0.023 | 0.280 | −1.64 |
| hippurate | Xenobiotics | Benzoate Metabolism | 0.023 | 0.285 | −3.42 |
| glutamate | Amino Acid | Glutamate Metabolism | 0.025 | 0.302 | −1.41 |
| maleate | Lipid | Fatty Acid, Dicarboxylate | 0.027 | 0.319 | −2.79 |
| 2-oxindole-3-acetate | Xenobiotics | Food Component/Plant | 0.029 | 0.326 | −4.93 |
| glycerophosphorylcholine_(GPC) | Lipid | Phospholipid Metabolism | 0.029 | 0.326 | −1.14 |
| sphingomyelin_(d18:1/14:0,_d16:1/ 16:0)* Lipid | Sphingolipid Metabolism | 0.029 | 0.326 | −2.00 | |
| N6-methyladenosine | Nucleotide | Purine Metabolism, Adenine containing | 0.031 | 0.333 | −1.09 |
| arachidonate_(20:4n6) | Lipid | Polyunsaturated Fatty Acid (n3 and n6) | 0.032 | 0.333 | −3.78 |
| 1-linoleoy1-2-arachidonoyl-GPC_(18:2/20:4n6)* Lipid | Phospholipid Metabolism | 0.032 | 0.333 | −3.63 | |
| tartarate | Xenobiotics | Food Component/Plant | 0.033 | 0.338 | −3.07 |
| laurate_(12:0) | Lipid | Medium Chain Fatty Acid | 0.034 | 0.346 | −2.44 |
| cytidine | Nucleotide | Pyrimidine Metabolism, Cytidine containing | 0.035 | 0.349 | −2.15 |
| hydantoin-5-propionic_acid | Amino Acid | Histidine Metabolism | 0.037 | 0.360 | −1.75 |
| cystathionine | Amino Acid | Methionine, Cysteine, SAM and Taurine Metabolism | 0.038 | 0.369 | −0.78 |
| ectoine | Xenobiotics | Chemical | 0.039 | 0.373 | 0.41 |
| glycochenodeoxycholate_glucuronide_(1) Lipid | Primary Bile Acid Metabolism | 0.041 | 0.373 | −0.60 | |
| sebacate_(decanedioate) | Lipid | Fatty Acid, Dicarboxylate | 0.042 | 0.373 | −1.61 |
| sphingosine_1-phosphate | Lipid | Sphingolipid Metabolism | 0.042 | 0.373 | −1.03 |
| 7-HOCA | Lipid | Sterol | 0.042 | 0.373 | −2.81 |
| bilirubin_(E, E)* | Cofactors and Vitamins | Hemoglobin and Porphyrin Metabolism | 0.042 | 0.373 | −1.97 |
| N-acetylproline | Amino Acid | Urea cycle; Arginine and Proline Metabolism | 0.048 | 0.401 | −2.97 |

TABLE 2-continued

Most Significant Plasma Metabolites.

| BIOCHEMICAL | SUPER_PATHWAY | SUB_PATHWAY | P-value | FDR | Fold Change |
|---|---|---|---|---|---|
| arabitol/xylitol | Carbohydrate | Pentose Metabolism | 0.048 | 0.401 | −8.82 |
| 3-hydroxybutyrylcarnitine_(2) | Lipid | Fatty Acid Metabolism(Acyl Carnitine) | 0.048 | 0.401 | −3.15 |
| allantoin | Nucleotide | Purine Metabolism, (Hypo)Xanthine/Inosine containing | 0.048 | 0.401 | −2.86 |

TABLE 3

Most significant fecal metabolites.

| BIOCHEMICAL | SUPER_PATHWAY | SUB_PATHWAY | p-value | Fold change |
|---|---|---|---|---|
| carnitine | Lipid | Carnitine Metabolism | 0.005 | −0.34 |
| sphingosine | Lipid | Sphingolipid Metabolism | 0.008 | −0.41 |
| 2'-deoxyadenosine | Nucleotide | Purine Metabolism, Adenine containing | 0.010 | 3.79 |
| indole | Amino Acid | Tryptophan Metabolism | 0.010 | −1.26 |
| adenine | Nucleotide | Purine Metabolism, Adenine containing | 0.013 | −2.15 |
| N-stearoyl-sphingosine (d18:1/18:0)* | Lipid | Sphingolipid Metabolism | 0.014 | −0.83 |
| 5alpha-androstan-3beta,17alpha-diol monosulfate (1) | Lipid | Steroid | 0.018 | 0.64 |
| cystathionine | Amino Acid | Methionine, Cysteine, SAM and Taurine Metabolism | 0.022 | −0.65 |
| 10-nonadecenoate (19:1n9) | Lipid | Long Chain Fatty Acid | 0.025 | −0.62 |
| imidazole propionate | Amino Acid | Histidine Metabolism | 0.025 | −0.20 |
| gulonate* | Cofactors and Vitamins | Ascorbate and Aldarate Metabolism | 0.025 | −0.11 |
| p-cresol sulfate | Amino Acid | Phenylalanine and Tyrosine Metabolism | 0.027 | −0.75 |
| N-acetylsphingosine | Lipid | Sphingolipid Metabolism | 0.028 | −0.33 |
| 1-(1-enyl-oleoyl)-GPE (P-18:1)* | Lipid | Lysoplasmalogen | 0.029 | −1.91 |
| 3-(3-hydroxyphenyl)propionate | Amino Acid | Phenylalanine and Tyrosine Metabolism | 0.029 | −0.06 |
| gamma-glutamylhistidine | Peptide | Gamma-glutamyl Amino Acid | 0.031 | −0.46 |
| deoxycarnitine | Lipid | Carnitine Metabolism | 0.032 | −0.22 |
| diaminopimelate | Xenobiotics | Food Component/Plant | 0.034 | −0.61 |
| tyramine O-sulfate | Amino Acid | Phenylalanine and Tyrosine Metabolism | 0.035 | 1.62 |
| gamma-tocotrienol | Cofactors and Vitamins | Tocopherol Metabolism | 0.037 | −2.62 |
| propionylglycine (C3) | Lipid | Fatty Acid Metabolism (also BCAA Metabolism) | 0.039 | −0.38 |
| 4-hydroxyphenylacetate | Amino Acid | Phenylalanine and Tyrosine Metabolism | 0.039 | −0.34 |
| delta-tocopherol | Cofactors and Vitamins | Tocopherol Metabolism | 0.039 | 21.67 |
| phenethylamine | Amino Acid | Phenylalanine and Tyrosine Metabolism | 0.042 | −0.31 |
| alpha-CEHC sulfate | Cofactors and Vitamins | Tocopherol Metabolism | 0.045 | 0.00 |
| betaine | Amino Acid | Glycine, Serine and Threonine Metabolism | 0.048 | −0.19 |

Example 4: Search for Combinations of
Metabolites to Best Differentiate the Two Groups
of Children Fisher Discriminant Analysis (FDA) methods were used to search for combinations of metabolites that best differentiated the two groups of children. To facilitate the analysis, a list of measurements was determined through an initial screening by excluding any metabolite with less than 15 non-minimum measurements (i.e., 39% of samples) from the full list of 621 plasma and 669 fecal metabolites. Then, a univariate analysis was conducted to calculate the area under the receiver operating characteristic curve (AUROC) for each metabolite individually. In each plasma and fecal metabolite data set, the one hundred measurements with the highest AUROC were accepted for multivariate analysis with FDA. The ten variables with the highest AUROC in each data set are listed in Table 4 (Plasma) and Table 5 (Fecal).

TABLE 4

| Top 10 plasma metabolites with the highest AUROC values | |
| --- | --- |
| Measurement | AUROC |
| nicotinamide riboside | 0.888 |
| inosine 5'-monophosphate (IMP) | 0.869 |
| HEPES | 0.865 |
| iminodiacetate (IDA) | 0.853 |
| methylsuccinate | 0.850 |
| galactonate | 0.842 |
| sarcosine | 0.828 |
| caprylate (8:0) | 0.822 |
| leucylglycine | 0.819 |
| heptanoate (7:0) | 0.815 |

TABLE 5

| Top 10 fecal metabolites with the highest AUROC values | |
| --- | --- |
| Measurement | AUROC |
| carnitine | 0.769 |
| sphingosine | 0.753 |
| 2'-deoxyadenosine | 0.747 |
| indole | 0.744 |
| adenine | 0.736 |
| N-stearoyl-spingosine (d18:1/18:0)* | 0.735 |
| imidazole propionate | 0.714 |
| 10-nonadecenoate (19:1n9) | 0.714 |

TABLE 5-continued

| Top 10 fecal metabolites with the highest AUROC values | |
| --- | --- |
| Measurement | AUROC |
| p-cresol sulfate | 0.711 |
| cystathionine | 0.711 |

Figure 2:
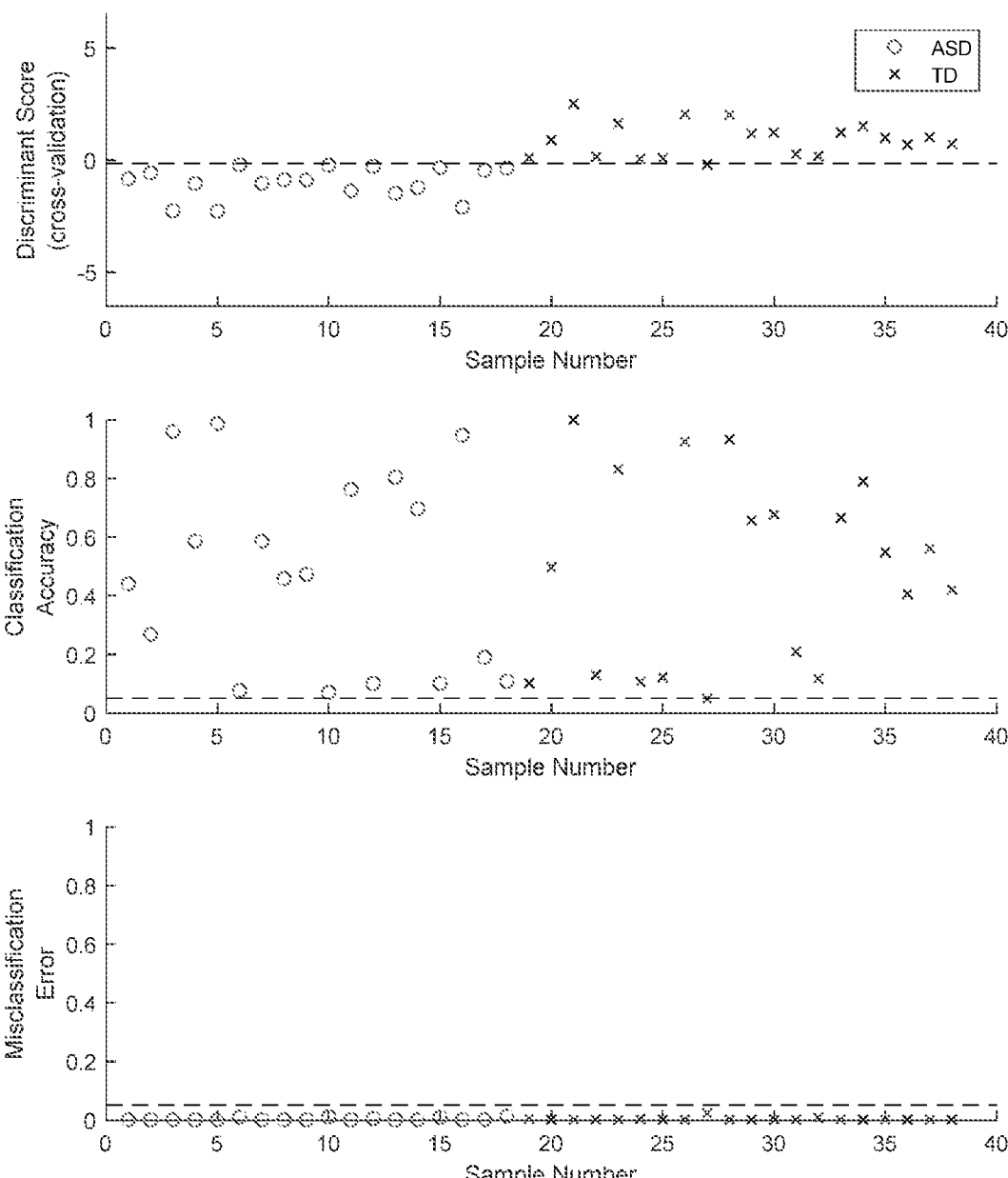
FIG. 2. Cross-validation of results of FIG. 1.
Figure 3:
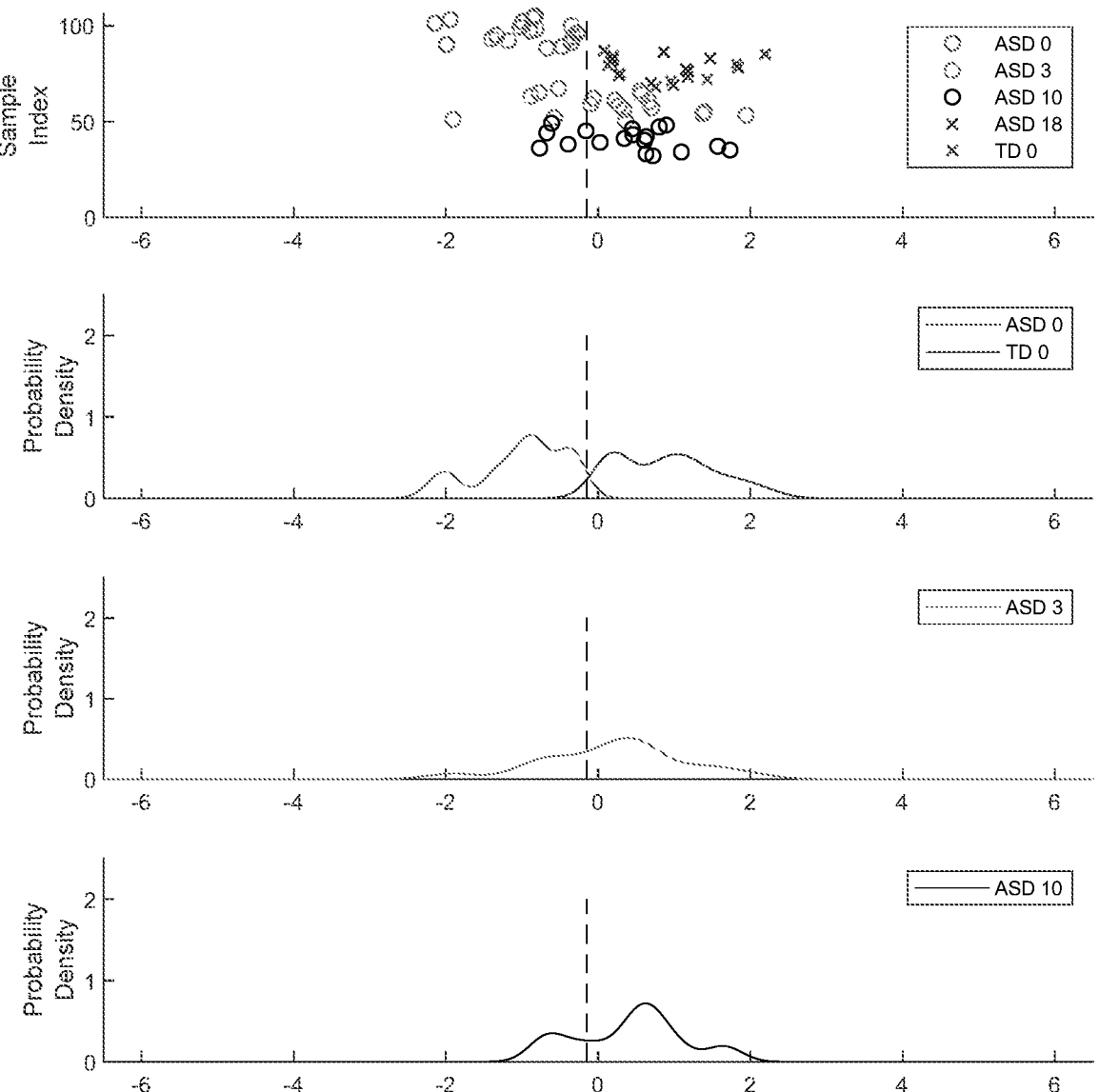
FIG. 3. Treatment effects.
Figure 4:
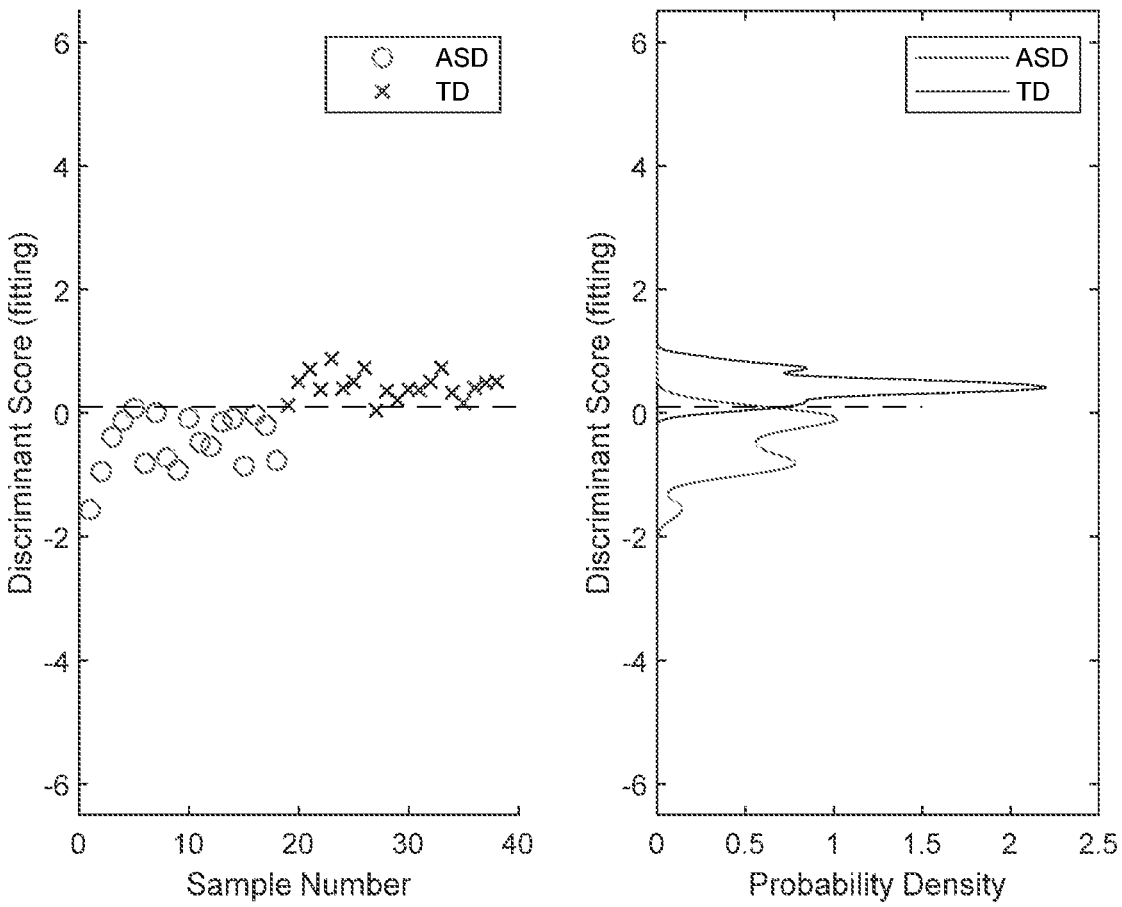
FIG. 4. Fitting results of plasma metabolites imidazole propionate, indole, 2-hydroxy-3-methylvalerate, hydroxyproline, and theobromine. Type I error of 7.5% and a Type II error of 7.0%.
Figure 5:
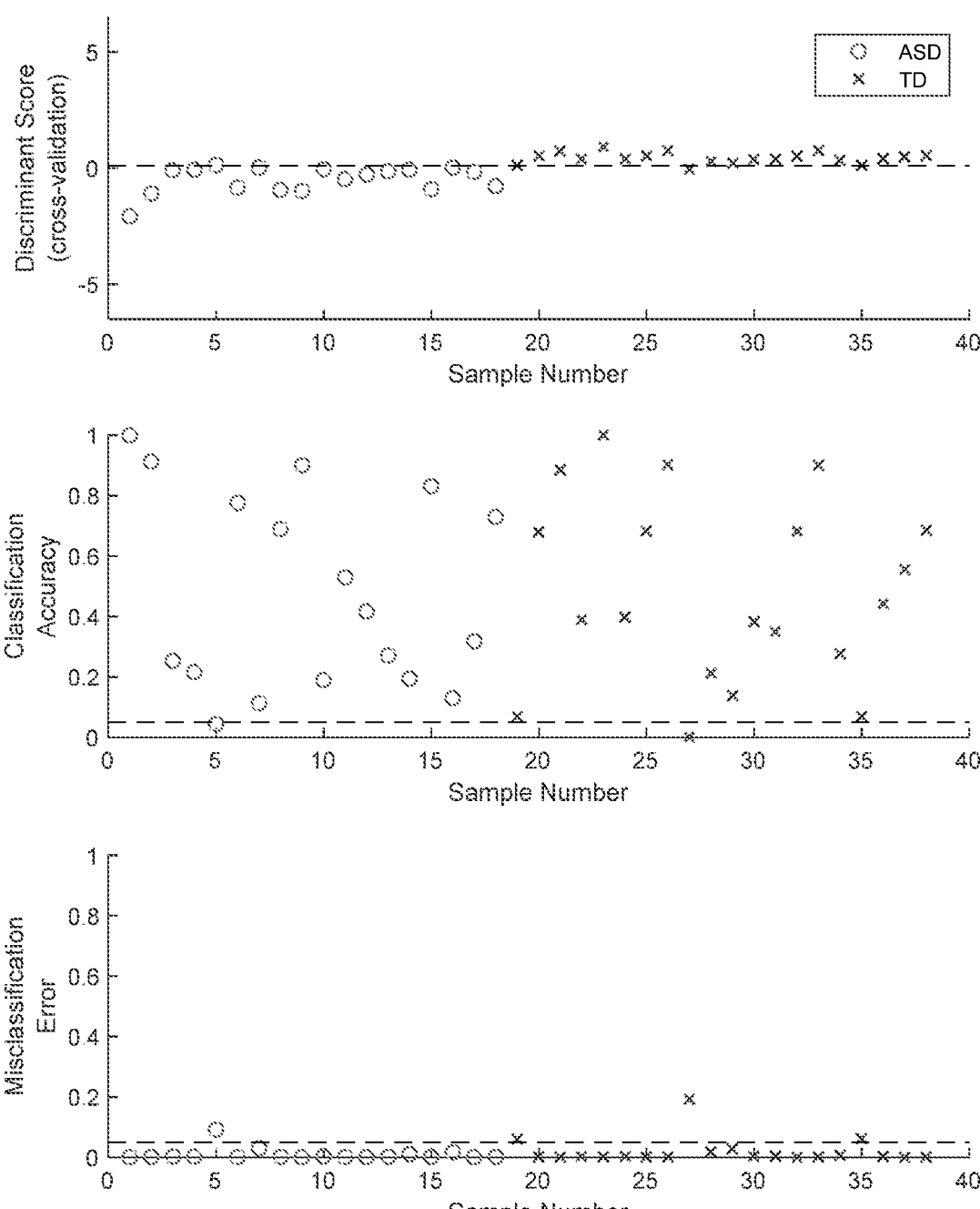
FIG. 5. Cross-validation of results of FIG. 4.
Figure 6:
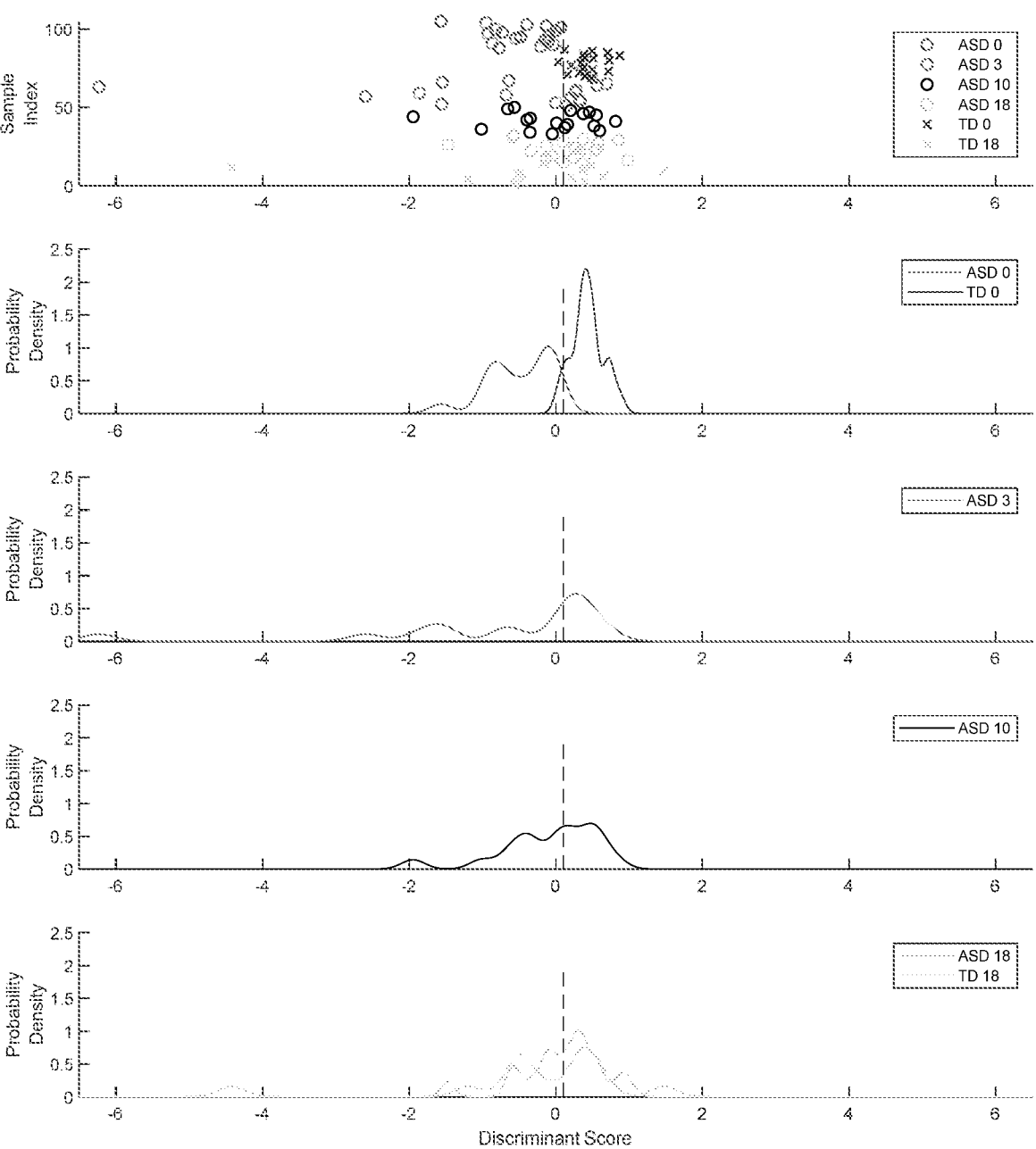
FIG. 6. Treatment results. Note: one sample at Week 3, with score=36.4, not shown.

For the classification with FDA, first the top 100 metabolites were used for each data set to exhaustively evaluate all combinations of up to four variables. For each number of variables, the 1000 combinations (or fewer if less than 1000 combinations in all) producing the highest AUROC from the fitted discriminant scores were retained. Then, a greedy algorithm was implemented to optimally add a fifth variable onto each of the 1000 best combinations of four variables. The top combinations from this greedy addition were then evaluated with cross-validation. The most promising candidates were the following combinations of metabolites: (Plasma; FIGS. 1-3 and Tables 6 and 7: 4 metabolites) inosine 5'-monophosphate (IMP), valylglycine, 1-(1-enyl-oleoyl)-GPE (P-18:1)*, gamma-glutamylglutamate, (Fecal; FIGS. 4-6 and 9 and Tables 8 and 9: 5 metabolites) imidazole propionate, indole, 2-hydroxy-3-methylvalerate, hydroxyproline, and theobromine.

TABLE 6

| Confusion matrix from cross-validation in FIG. 2 | | | | |
| --- | --- | --- | --- | --- |
| | | Predicted | | |
| | | ASD (n = 19) | TD (n = 19) | |
| Actual | ASD (n = 18) | TP = 18 | FN = 0 | TPR = 1.0 |
| | TD (n = 20) | FP = 1 | TN = 19 | TNR = 0.950 |
| | | PPV = 0.947 | NPV = 1.0 | |

TABLE 7

| Time Point | Type II Error (based on shown threshold) |
| --- | --- |
| Week 0 | 4.0% |
| Week 3 | 66.7% |
| Week 10 | 74.5% |

NOTE:
an increase in Type II error is desired as the goal is to make the ASD cohort more closely resemble the TD cohort

TABLE 8

| Confusion matrix from cross-validation | | | | |
| --- | --- | --- | --- | --- |
| | | Predicted | | |
| | | ASD (n = 18) | TD (n = 20) | |
| Actual | ASD (n = 18) | TP = 17 | FN = 1 | TPR = 0.944 |
| | TD (n = 20) | FP = 1 | TN = 19 | TNR = 0.950 |
| | | PPV = 0.944 | NPV = 0.950 | |

TABLE 9

| Time Point | Type II Error (based on shown threshold) |
| --- | --- |
| Week 0 | 7.0% |
| Week 3 | 46.7% |
| Week 10 | 46.3% |
| Week 18 | 55.3% |

Example 5: Methodology of Measuring Metabolites Using the Metabolon System

Sample acquisition. Following receipt, samples were inventoried and immediately stored at −80° C. Each sample received was accessioned into the Metabolon LIMS system and was assigned by the LIMS a unique identifier that was associated with the original source identifier only. This identifier was used to track all sample handling, tasks, results, etc. The samples (and all derived aliquots) were tracked by the LIMS system. All portions of any sample were automatically assigned their own unique identifiers by the LIMS when a new task was created; the relationship of these samples was also tracked. All samples were maintained at −80° C. until processed.

Sample Preparation: Samples were prepared using the automated MicroLab STAR® system from Hamilton Company. Several recovery standards were added prior to the first step in the extraction process for QC purposes. To remove protein, dissociate small molecules bound to protein or trapped in the precipitated protein matrix, and to recover chemically diverse metabolites, proteins were precipitated with methanol under vigorous shaking for 2 min (Glen Mills GenoGrinder 2000) followed by centrifugation. The resulting extract was divided into five fractions: two for analysis by two separate reverse phase (RP)/UPLC-MS/MS methods with positive ion mode electrospray ionization (ESI); one for analysis by RP/UPLC-MS/MS with negative ion mode ESI; one for analysis by HILIC/UPLC-MS/MS with negative ion mode ESI; and one sample was reserved for backup. Samples were placed briefly on a TurboVap® (Zymark) to remove the organic solvent. The sample extracts were stored overnight under nitrogen before preparation for analysis.

Figure 7:
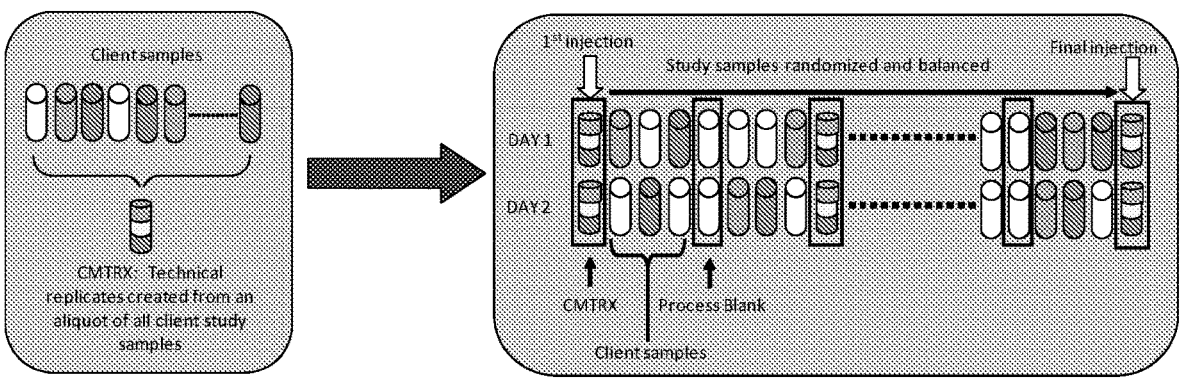
FIG. 7. Preparation of client-specific technical replicates. A small aliquot of each client sample (colored cylinders) is pooled to create a CMTRX technical replicate sample (multi-colored cylinder), which is then injected periodically throughout the platform run. Variability among consistently detected biochemicals can be used to calculate an estimate of overall process and platform variability.

QA/QC: Several types of controls were analyzed in concert with the experimental samples: a pooled matrix sample generated by taking a small volume of each experimental sample (or alternatively, use of a pool of well-characterized human plasma) served as a technical replicate throughout the data set; extracted water samples served as process blanks; and a cocktail of QC standards that were carefully chosen not to interfere with the measurement of endogenous compounds were spiked into every analyzed sample, allowed instrument performance monitoring, and aided chromatographic alignment. Tables 10 and 11 describe these QC samples and standards. Instrument variability was determined by calculating the median relative standard deviation (RSD) for the standards that were added to each sample prior to injection into the mass spectrometers. Overall process variability was determined by calculating the median RSD for all endogenous metabolites (i.e., non-instrument standards) present in 100% of the pooled matrix samples. Experimental samples were randomized across the platform run with QC samples spaced evenly among the injections, as outlined in FIG. 7.

TABLE 10

| Description of Metabolon QC Samples | | |
| --- | --- | --- |
| Type | Description | Purpose |
| MTRX | Large pool of human plasma maintained by Metabolon that has been characterized extensively. | Assure that all aspects of the Metabolon process are operating within specifications. |
| CMTRX | Pool created by taking a small aliquot from every customer sample. | Assess the effect of a non-plasma matrix on the Metabolon process and distinguish biological variability from process variability. |
| PROS | Aliquot of ultra-pure water | Process Blank used to assess the contribution to compound signals from the process. |
| SOLV | Aliquot of solvents used in extraction. | Solvent Blank used to segregate contamination sources in the extraction. |

TABLE 11

| Metabolon QC Standards | | |
| --- | --- | --- |
| Type | Description | Purpose |
| RS | Recovery Standard | Assess variability and verify performance of extraction and instrumentation. |
| IS | Internal Standard | Assess variability and performance of instrument. |

Ultrahigh Performance Liquid Chromatography-Tandem Mass Spectroscopy (UPLC-MS/MS): All methods utilized a Waters ACQUITY ultra-performance liquid chromatography (UPLC) and a Thermo Scientific Q-Exactive high resolution/accurate mass spectrometer interfaced with a heated electrospray ionization (HESI-II) source and Orbitrap mass analyzer operated at 35,000 mass resolution. The sample extract was dried then reconstituted in solvents compatible to each of the four methods. Each reconstitution solvent contained a series of standards at fixed concentrations to ensure injection and chromatographic consistency. One aliquot was analyzed using acidic positive ion conditions, chromatographically optimized for more hydrophilic compounds. In this method, the extract was gradient eluted from a C18 column (Waters UPLC BEH C18-2.1×100 mm, 1.7 μm) using water and methanol, containing 0.05% perfluoropentanoic acid (PFPA) and 0.1% formic acid (FA). Another aliquot was also analyzed using acidic positive ion conditions; however it was chromatographically optimized for more hydrophobic compounds. In this method, the extract was gradient eluted from the same aforementioned C18 column using methanol, acetonitrile, water, 0.05% PFPA and 0.01% FA, and was operated at an overall higher organic content. Another aliquot was analyzed using basic negative ion optimized conditions using a separate dedicated C18 column. The basic extracts were gradient eluted from the column using methanol and water, however with 6.5 mM Ammonium Bicarbonate at pH 8. The fourth aliquot was analyzed via negative ionization following elution from a HILIC column (Waters UPLC BEH Amide 2.1×150 mm, 1.7 μm) using a gradient consisting of water and acetonitrile with 10 mM Ammonium Formate, pH 10.8. The MS analysis alternated between MS and data-dependent MSn scans using dynamic exclusion. The scan range varied slighted between methods but covered 70-1000 m/z. Raw data files are archived and extracted as described below.

Bioinformatics: The informatics system consisted of four major components, the Laboratory Information Management System (LIMS), the data extraction and peak-identification software, data processing tools for QC and compound identification, and a collection of information interpretation and visualization tools for use by data analysts. The hardware and software foundations for these informatics components were the LAN backbone and a database server running Oracle 10.2.0.1 Enterprise Edition.

LIMS: The purpose of the Metabolon LIMS system was to enable fully auditable laboratory automation through a secure, easy to use, and highly specialized system. The scope of the Metabolon LIMS system encompasses sample accessioning, sample preparation and instrumental analysis, and reporting and advanced data analysis. All of the subsequent software systems are grounded in the LIMS data structures. It has been modified to leverage and interface with the in-house information extraction and data visualization systems, as well as third party instrumentation and data analysis software.

Data Extraction and Compound Identification: Raw data was extracted, peak-identified and QC processed using Metabolon's hardware and software. These systems are built on a web-service platform utilizing Microsoft's .NET technologies, which run on high-performance application servers and fiber-channel storage arrays in clusters to provide active failover and load-balancing. Compounds were identified by comparison to library entries of purified standards or recurrent unknown entities. Metabolon maintains a library based on authenticated standards that contains the retention time/index (RI), mass to charge ratio (m/z), and chromatographic data (including MS/MS spectral data) on all molecules present in the library. Furthermore, biochemical identifications are based on three criteria: retention index within a narrow RI window of the proposed identification, accurate mass match to the library+/-10 ppm, and the MS/MS forward and reverse scores between the experimental data and authentic standards. The MS/MS scores are based on a comparison of the ions present in the experimental spectrum to the ions present in the library spectrum. While there may be similarities between these molecules based on one of these factors, the use of all three data points can be utilized to distinguish and differentiate biochemicals. More than 3300 commercially available purified standard compounds have been acquired and registered into LIMS for analysis on all platforms for determination of their analytical characteristics. Additional mass spectral entries have been created for structurally unnamed biochemicals, which have been identified by virtue of their recurrent nature (both chromatographic and mass spectral). These compounds have the potential to be identified by future acquisition of a matching purified standard or by classical structural analysis.

Curation: A variety of curation procedures were carried out to ensure that a high quality data set was made available for statistical analysis and data interpretation. The QC and curation processes were designed to ensure accurate and consistent identification of true chemical entities, and to remove those representing system artifacts, mis-assignments, and background noise. Metabolon data analysts used proprietary visualization and interpretation software to confirm the consistency of peak identification among the various samples. Library matches for each compound were checked for each sample and corrected if necessary.

Figure 8:
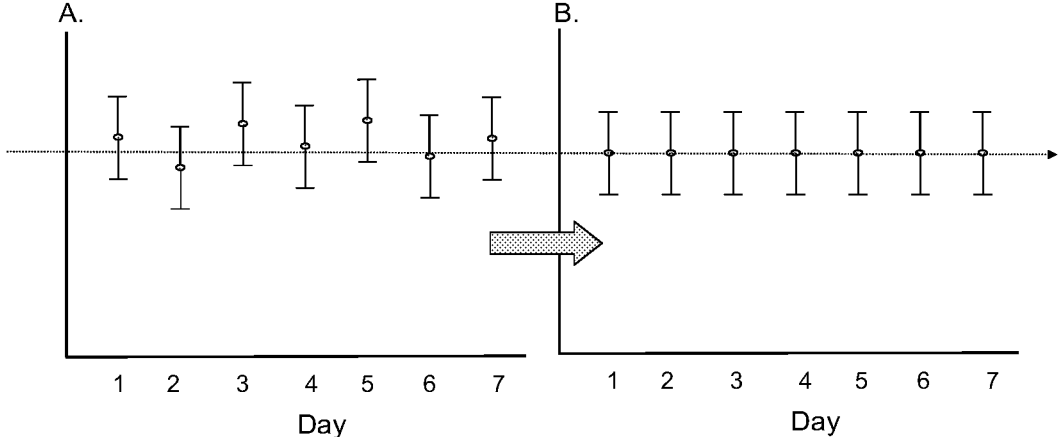
FIG. 8. Visualization of data normalization steps for a multiday platform run.

Metabolite Quantification and Data Normalization: Peaks were quantified using area-under-the-curve. For studies spanning multiple days, a data normalization step was performed to correct variation resulting from instrument inter-day tuning differences. Essentially, each compound was corrected in run-day blocks by registering the medians to equal one (1.00) and normalizing each data point proportionately (termed the "block correction"; FIG. 8). For studies that did not require more than one day of analysis, no normalization is necessary, other than for purposes of data visualization. In certain instances, biochemical data may have been normalized to an additional factor (e.g., cell counts, total protein as determined by Bradford assay, osmolality, etc.) to account for differences in metabolite levels due to differences in the amount of material present in each sample.

Example 6: Plasma Metabolites in Children with Autism Spectrum Disorder and Gastrointestinal Symptoms: Results from Baseline and after Microbiota Transfer Therapy Current diagnosis of autism spectrum disorder (ASD) is based on an assessment of behavioral symptoms. However, there is strong evidence that ASD affects multiple organ systems including, but not limited to, the gastrointestinal tract. Multivariate statistical analysis of plasma metabolites from a set of 18 children with ASD and chronic gastrointestinal problems and 20 typically developing children without gastrointestinal problems was performed. Using Fischer discriminant analysis and leave-one-out cross-validation, results at baseline were used to distinguish the two groups of children, and the analysis was applied to the ASD group during and after Microbiota Transfer Therapy (MTT). Using only three of the plasma metabolites, it was possible to distinguish the children with ASD and gastrointestinal disorders from their typically developing peers with sensitivity and specificity of 94% and 100%, respectively. After MTT, there was a significant improvement in gastrointestinal and ASD-related symptoms, which is also reflected in the metabolites, as the participants' metabolic profiles shifted significantly to become more similar to the typically developing group. These results indicate that this combination of plasma metabolites may also be a useful biomarker for treatment efficacy. Each of the three plasma metabolites was correlated with several or many other metabolites, so the three metabolites represent three general areas of metabolic abnormalities in ASD. Two of the metabolites, sarcosine and inosine 5'-monophosphate, improved substantially during and after MTT, but one of them (tyramine O-sulfate) did not change notably, and hence it (and correlated metabolites) may be a target for future therapies.

Methods

Study Population and MTT Treatment

The details of the study population and MTT protocol are outlined in a previous study. Briefly, the study involved 18 children with ASD and chronic GI problems (ASD+GI cohort) and 20 TD children without GI problems (TD–GI cohort), all aged 7-16 years old. ASD+GI participants' medical records from the previous two years were extensively reviewed by the study physician to determine eligibility for the study. Diagnoses of ASD were then verified using the Autism Diagnostic Interview-Revised through a phone interview with the parents by an evaluator. This was followed by a general physical health examination by the study physician to verify that the children had chronic GI symptoms of moderate to severe severity. Exclusion criteria included antibiotic use in the previous six months or probiotic use in the previous three months, dependence on tube feeding, the presence of life-threatening GI problems, having recent or scheduled surgeries, being severely malnourished or underweight, and being diagnosed with a single-gene disorder, major brain malformation, ulcerative colitis, Crohn's disease, celiac disease, or eosinophilic esophagitis. TD children were identified as those not having a diagnosed mental disorder including ASD, attention-deficit hyperactivity disorder, depression, or anxiety, in addition, none of the TD children had parents or siblings with ASD.

MTT included two weeks of oral vancomycin (an antibiotic to reduce pathogenic bacteria), one day of fasting and MoviPrep (a bowel cleanse to remove the vancomycin and further reduce levels of intestinal bacteria), one or two days of a high-dose of fecal microbiota (FM), and seven or eight weeks of low-dose FM. The FM consisted of a full spectrum of highly-purified microbiota extracted from stool samples of healthy, carefully-screened donors and prepared as previously described. Prilosec, a stomach acid suppressant, was also administered during eight weeks of treatment to increase the survival of orally administered FM through the stomach.

Improvement of GI symptoms through MTT was primarily assessed by the Gastrointestinal Symptom Rating Scale (GSRS) as completed by parents/guardians. The GSRS contains fifteen questions scored in five domains (abdominal pain, reflux, indigestion, diarrhea, and constipation) for evaluating GI symptoms during the previous week on a seven-point Likert scale. From the beginning to the end of MTT, the average GSRS score decreased 82% compared to baseline; eight weeks after treatment stopped, the average score was still 77% lower than at baseline. Changes in ASD-related symptoms were evaluated by the Childhood Autism Rating Scale (CARS), Social Responsiveness Scale, Aberrant Behavior Checklist, and Parental Global Impressions-Ill (PGI-Ill). Compared to baseline, the average CARS score decreased by 22% after MTT and by 24% after the eight weeks of follow-up. A significant negative correlation was also detected between the change in GSRS and PGI-Ill (Spearman rank correlation coefficient of −0.59).

Metabolite Measurements

Plasma samples were collected by phlebotomists in the morning from fasting participants. The samples were frozen immediately and stored in a −80° C. freezer. When all samples for the study were collected, they were shipped on dry ice to Metabolon (Durham, NC, USA), where sample preparation and data acquisition were processed to obtain metabolite profiling. Samples were extracted and analyzed by the Metabolon platform with the ultrahigh performance liquid chromatography-tandem mass spectroscopy (UPLC-MS/MS) instruments. The Metabolon platform consists of sample accessioning, sample preparation, quality assurance/quality control, and UPLC-MS/MS measurements, and the detailed information is described by Long et al. Measurements for a total of 621 plasma metabolites were available for this study.

Plasma samples were collected from all ASD+GI participants at baseline (Week 0), after the administration of oral vancomycin prior to microbiota transfusion (Week 3), and after the end of MTT treatment (Week 10). Plasma samples from TD−GI controls were only collected at Week 0 as these participants did not undergo treatment.

Statistical Methods

Multivariate analysis was performed with Fisher discriminant analysis (FDA). The objective of FDA is to determine a linear combination of metabolites that best separates the ASD+GI and TD−GI study cohorts at baseline (pre-treatment). Prior to FDA, each metabolite measurement was rescaled so that the mean value in the combined ASD+GI and TD−GI groups was 0 with a standard deviation of 1. A discriminant score was calculated by FDA for each study participant by multiplying each input metabolite measurement by a calculated parameter value and then summing these products together. The parameters for each metabolite were estimated such that the difference in mean discriminant score between the ASD+GI cohort and TD−GI cohort was maximized, and the variance of scores within each cohort was simultaneously minimized. Further mathematical details of the algorithm are provided in a previous paper by the inventors. Although other methods can be used, FDA has been found to be well-suited for this type of research.

Performing FDA with all available metabolite measurements would lead to model overfitting and minimize generalizability of any findings, thus, it was necessary to identify an optimal subset of measurements to use for FDA. To facilitate this analysis, a list of the most significant metabolites for classification was determined through a two-step process. First, any metabolites having fewer than 15 measurements (i.e., 40% of samples) above the detection limit were excluded. The rationale with this step was to focus only on metabolites that had continuous distributions of values across participants, while still allowing for the possibility that a measurement could be almost entirely below the detection limit in one cohort and above the limit in the other cohort. A univariate analysis was then conducted to compute a receiver operating characteristic (ROC) curve for each individual metabolite by plotting the false positive rate against the false negative rate at different ASD/TD classification thresholds. The area under the ROC curve (AUROC) was then calculated to quantify the separation between ASD and TD cohorts offered by the metabolite. Values of the AUROC typically range between 0.5 and 1.0, with a value of 0.5 indicating uninformative classification and a value of 1.0 denoting perfect separation. Metabolites yielding an AUROC of at least 0.70 were accepted as candidates for multivariate analysis with FDA.

Classification with FDA first involved using the top candidate metabolites to exhaustively evaluate all combinations of up to five metabolites. For each number of metabolites used (two, three, four, or five), the 1000 combinations producing the highest AUROC from the fitted discriminant scores were retained. The distributions of fitted discriminant scores for each cohort (ASD or TD) yielded by each retained combination in FDA were then estimated with kernel density estimation, this method uses Gaussian kernels to provide an approximation of the probability density functions (PDFs) of the discriminant scores. Defining the classification threshold for separating these distributions to be the null hypothesis H0, which states that a given sample belongs to the TD cohort, the Type I error is then taken to be the probability of incorrectly diagnosing a TD participant as having ASD (i.e., the false positive rate). Similarly, the Type II error ($\beta$) is defined as the probability of incorrectly diagnosing a participant with ASD as being TD (i.e., the false negative rate). The Type I and Type II errors were calculated based on H0 with respect to the PDFs obtained from model fitting.

The 1000 best combinations for each number of metabolites were evaluated with leave-one-out cross-validation, in which the classification of each participant is predicted using an FDA model fitted to the remaining (n minus 1) participants' samples. This is an important step, as it means that rather than merely fitting to the data, an estimate of the model's ability to predict new data is obtained. It generally results in lower sensitivity and specificity than fitting procedures, but the results are more likely to indicate generalizability to larger data sets. To evaluate each candidate model, the cross-validated sensitivity (or true positive rate, TPR) and specificity (or true negative rate, TNR) were calculated at the values of the classification threshold H0 for which β=0.01, 0.05, 0.10, and 0.20; modulating H0 in such a manner allowed characterization of the cross-validated performance of each model when the classification threshold was placed at different points along the ASD distribution.

To further evaluate individual FDA models, sample-level classification accuracies (CAs) and misclassification errors (MEs) resulting from leave-one-out cross-validation were also assessed. While holding out each participant in cross-validation, the PDFs of the discriminant scores for the remaining n minus 1 participants were estimated. The percent membership of a held-out sample in its own cohort's PDF (i.e., the probability of being classified in the correct cohort) was taken to be that sample's CA, while the percent membership in the incorrect cohort's PDF (i.e., the probability of being classified in the incorrect cohort) was defined to be the sample's ME. High-confidence models are those having many samples with CA greater than 0.05 and ME less than 0.05.

The FDA model developed at baseline was used to assess changes in the plasma metabolite data for participants with ASD at Week 3 and Week 10 of MTT treatment. Data from these time points were normalized according to the mean and standard deviation parameters used to normalize the Week 0 metabolites. Changes resulting from MTT were quantified by the Type II error (probability of incorrectly classifying someone with ASD as TD), with respect to the classification threshold H0, that was associated with the PDF of the ASD cohort's discriminant scores at each time point. While the goal is typically to minimize the Type II error, a larger Type II error is desired in this analysis since it is expected that successful treatment will make the ASD cohort's distribution less distinguishable from that of the TD cohort. An additional metric of MTT effect was the effect size, calculated at each time point as the median difference in discriminant score from baseline (where each participant's sample was paired with their baseline sample); the 95% confidence interval (CI) for the effect size was calculated by non-parametric bootstrap resampling with 10000 resamples. Significance level α=0.05 was used for all hypothesis testing.

Results

Univariate Analysis

From 621 total metabolites, 45 metabolites were excluded for not having at least 15 values above the detection limit. Two others were excluded for being artifacts of sample processing (HEPES and EDTA) and thus not having biological relevance to the current analysis, leaving 574 metabolites for univariate ROC analysis. Of those 574 metabolites, there were 61 with an AUROC of at least 0.70 (Table 12). No single metabolite perfectly separated the ASD and TD cohorts, but 11 metabolites did have an AUROC greater than 0.80, suggesting modest potential for univariate classification with these measurements.

TABLE 12

The 61 plasma metabolites with at least 15 values above the detection limit and yielding at least 0.70 AUROC on a univariate basis. These metabolites were retained for multivariate analysis with FDA.

| Metabolite Rank | Metabolite | AUROC |
|---|---|---|
| 1 | nicotinamide riboside | 0.89 |
| 2 | inosine 5'-monophosphate (IMP) | 0.87 |
| 3 | iminodiacetate (IDA) | 0.85 |
| 4 | methylsuccinate | 0.85 |
| 5 | galactonate | 0.84 |
| 6 | sarcosine | 0.83 |
| 7 | caprylate (8:0) | 0.82 |
| 8 | leucylglycine | 0.82 |
| 9 | heptanoate (7:0) | 0.82 |
| 10 | valylglycine | 0.81 |
| 11 | 1-palmitoyl-GPI* (16:0)* | 0.79 |
| 12 | 3-phosphoglycerate | 0.79 |
| 13 | N6-acetyllysine | 0.78 |
| 14 | 1-stearoyl-GPS (18:0)* | 0.78 |
| 15 | caproate (6:0) | 0.77 |
| 16 | 1-arachidonoyl-GPI* (20:4)* | 0.77 |
| 17 | 1-(1-enyl-oleoyl)-GPE (P-18:1)* | 0.77 |
| 18 | azelate (nonanedioate, C9) | 0.76 |
| 19 | 2-aminophenol sulfate | 0.76 |
| 20 | glycerophosphoethanolamine | 0.76 |
| 21 | 1-methylimidazoleacetate | 0.76 |
| 22 | 2-methylserine | 0.76 |
| 23 | 10-undecenoate (11:1n1) | 0.76 |
| 24 | biliverdin | 0.76 |
| 25 | indolepropionate | 0.76 |
| 26 | citrate | 0.75 |
| 27 | 1-oleoyl-GPS (18:1) | 0.75 |
| 28 | bilirubin | 0.74 |
| 29 | tiglyl carnitine (C5) | 0.74 |
| 30 | picolinate | 0.74 |
| 31 | 5,6-dihydrothymine | 0.74 |
| 32 | 21-hydroxypregnenolone disulfate | 0.74 |
| 33 | 1-stearoyl-GPI (18:0) | 0.74 |
| 34 | propionylglycine (C3) | 0.73 |
| 35 | 2-hydroxystearate | 0.73 |
| 36 | cysteinylglycine | 0.73 |
| 37 | 3-methoxycatechol sulfate (1) | 0.73 |
| 38 | creatine | 0.72 |
| 39 | maltotetraose | 0.72 |
| 40 | 9,10-DiHOME | 0.72 |
| 41 | sphingomyelin (d18:2/23:0, d18:1/23:1, d17:1/24:1)* | 0.72 |
| 42 | cys-gly, oxidized | 0.72 |
| 43 | gamma-glutamylhistidine | 0.72 |
| 44 | S-1-pyrroline-5-carboxylate | 0.72 |
| 45 | fructose | 0.72 |
| 46 | 1-arachidonylglycerol (20:4) | 0.72 |
| 47 | hippurate | 0.72 |
| 48 | cinnamoylglycine | 0.72 |
| 49 | glutamate | 0.71 |
| 50 | tyramine O-sulfate | 0.71 |
| 51 | maleate | 0.71 |
| 52 | glycerophosphorylcholine (GPC) | 0.71 |
| 53 | sphingomyelin (d18:1/14:0, d16:1/16:0)* | 0.71 |
| 54 | arachidonate (20:4n6) | 0.71 |
| 55 | 1-linoleoyl-2-arachidonoyl-GPC (18:2/20:4n6)* | 0.71 |
| 56 | N6-methyladenosine | 0.70 |
| 57 | tartarate | 0.70 |
| 58 | laurate (12:0) | 0.70 |
| 59 | 2-oxindole-3-acetate | 0.70 |
| 60 | cytidine | 0.70 |
| 61 | hydantoin-5-propionic acid | 0.70 |

Classification with FDA—Model development and selection. The most promising combinations of two, three, four, and five metabolites for FDA are listed in Table 13. These combinations yielded the highest sensitivity and specificity after cross-validation, which also coincided with high AUROC from the fitted models. Perfect separation from fitting was observed with as few as three metabolites, and perfect prediction from cross-validation with as few as four metabolites; the term "separation" was used for indicating the difference between cohorts yielded by model fitting, and "prediction" when presenting cross-validated results. In the interest of balancing high model accuracy and low model complexity, the best three-metabolite model using sarcosine, tyramine O-sulfate, and inosine 5-monophosphate (IMP) as inputs (hereafter referred to as the PM3, or plasma model with three metabolites) was considered for further analysis. Assessing model accuracy at different classification thresholds of p provided an indication of the optimal cut-off between the ASD and TD distributions.

TABLE 13

Fitting and cross-validation results for the best combination of two, three, four, and five metabolites used in FDA. The cross-validated sensitivity (or true positive rate, TPR) and the specificity (or true negative rate, TNR) are shown for classification thresholds associated with different values of $\beta$ calculated from the fitted PDFs.

| Number of Metabolites | Metabolite Combination | Fitted AUROC | Cross-Validated Results | | |
|---|---|---|---|---|---|
| | | | $\beta$ | TPR | TNR |
| 2 | tyramine O-sulfate | 0.97 | 0.01 | 1.00 | 0.70 |
| | inosine 5'-monophosphate | | 0.05 | 0.94 | 0.80 |
| | | | 0.10 | 0.94 | 0.90 |
| | | | 0.20 | 0.83 | 0.95 |
| 3 | sarcosine | 1.00 | 0.01 | 1.00 | 0.95 |
| | tyramine O-sulfate | | 0.05 | 0.94 | 1.00 |
| | inosine 5'-monophosphate | | 0.10 | 0.94 | 1.00 |
| | | | 0.20 | 0.83 | 1.00 |
| 4 | sarcosine | 1.00 | 0.01 | 1.00 | 0.95 |
| | tyramine O-sulfate | | 0.05 | 0.94 | 1.00 |
| | arachidonate (20:4n6) | | 0.10 | 0.89 | 1.00 |
| | inosine 5'-monophosphate | | 0.20 | 0.83 | 1.00 |
| 5 | sarcosine | 1.00 | 0.01 | 1.00 | 1.00 |
| | tyramine O-sulfate | | 0.05 | 0.94 | 1.00 |
| | 1-arachidonoyl-GPI* (20:4)* | | 0.10 | 0.89 | 1.00 |
| | sphingomyelin (d18:2/23:0, d18:1/23:1, d17:1/24:1)* | | 0.20 | 0.78 | 1.00 |
| | inosine 5'-monophosphate | | | | |

Figure 9A:
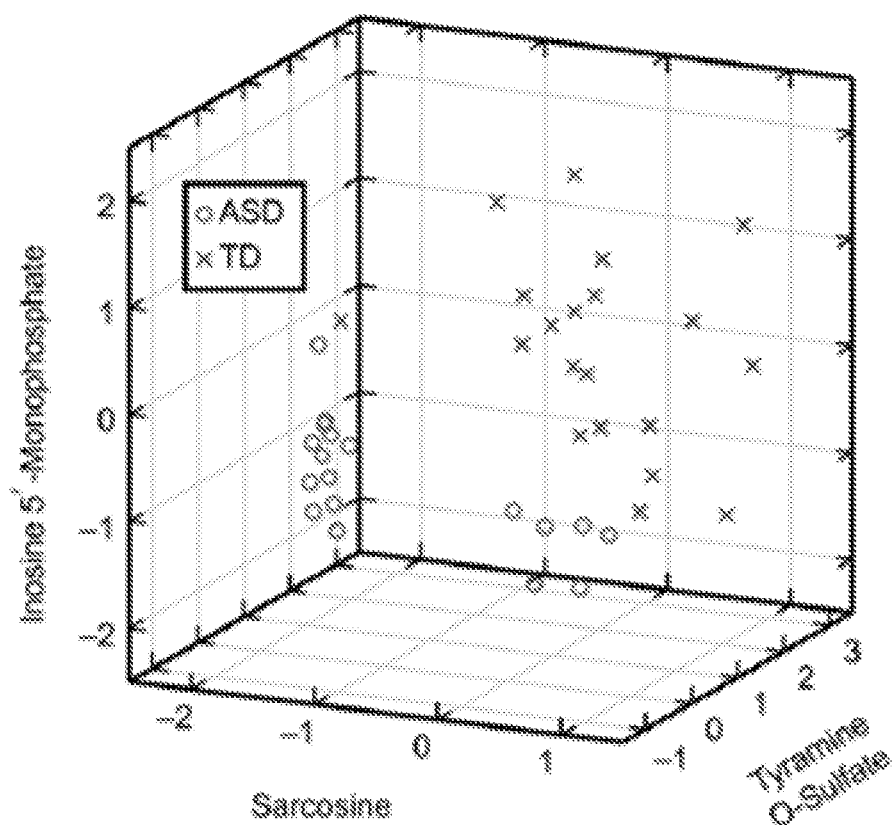
FIG. 9A. Univariate characteristics of the PM3. Three-dimensional plot for visualizing separation between the ASD and TD cohorts at baseline provided by the three (normalized) metabolites of the PM3.
Figure 9B:
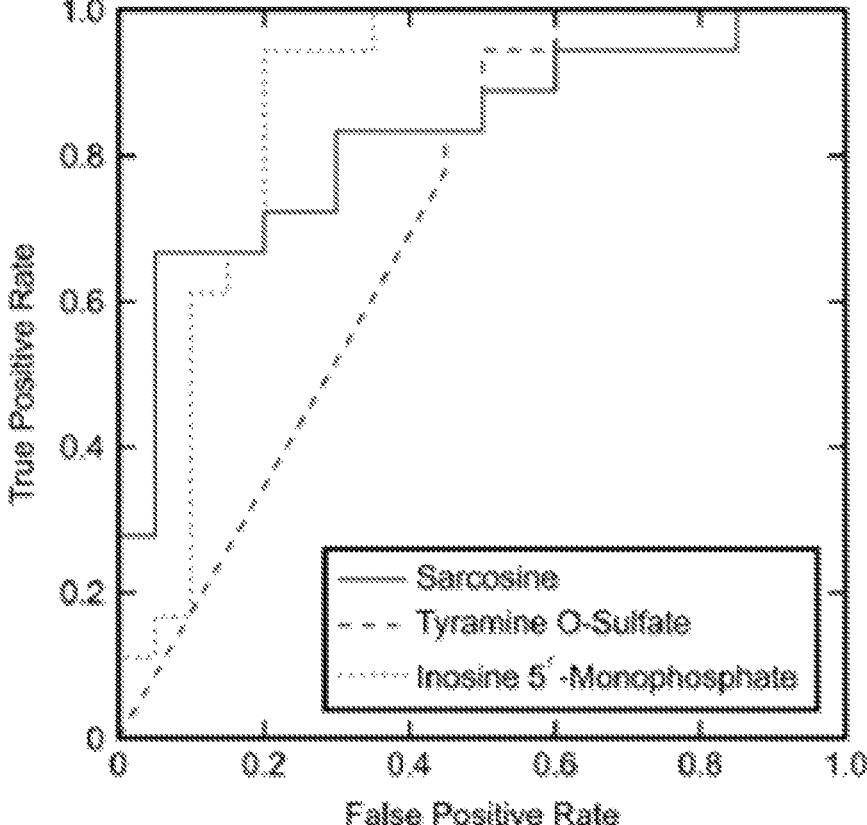
FIG. 9B. Univariate characteristics of the PM3. ROC curves for the three PM3 metabolites.

Univariate separation between the ASD and TD cohorts provided by each of the PM3 metabolites is visualized in FIG. 9A. This plot shows that the two cohorts separate well when accounting for the three metabolites together. The ROC curves for each of the three PM3 metabolites (FIG. 9B) also indicate an ability to classify the two cohorts with reasonable accuracy, albeit not as accurately as with the multivariate model.

Figure 10:
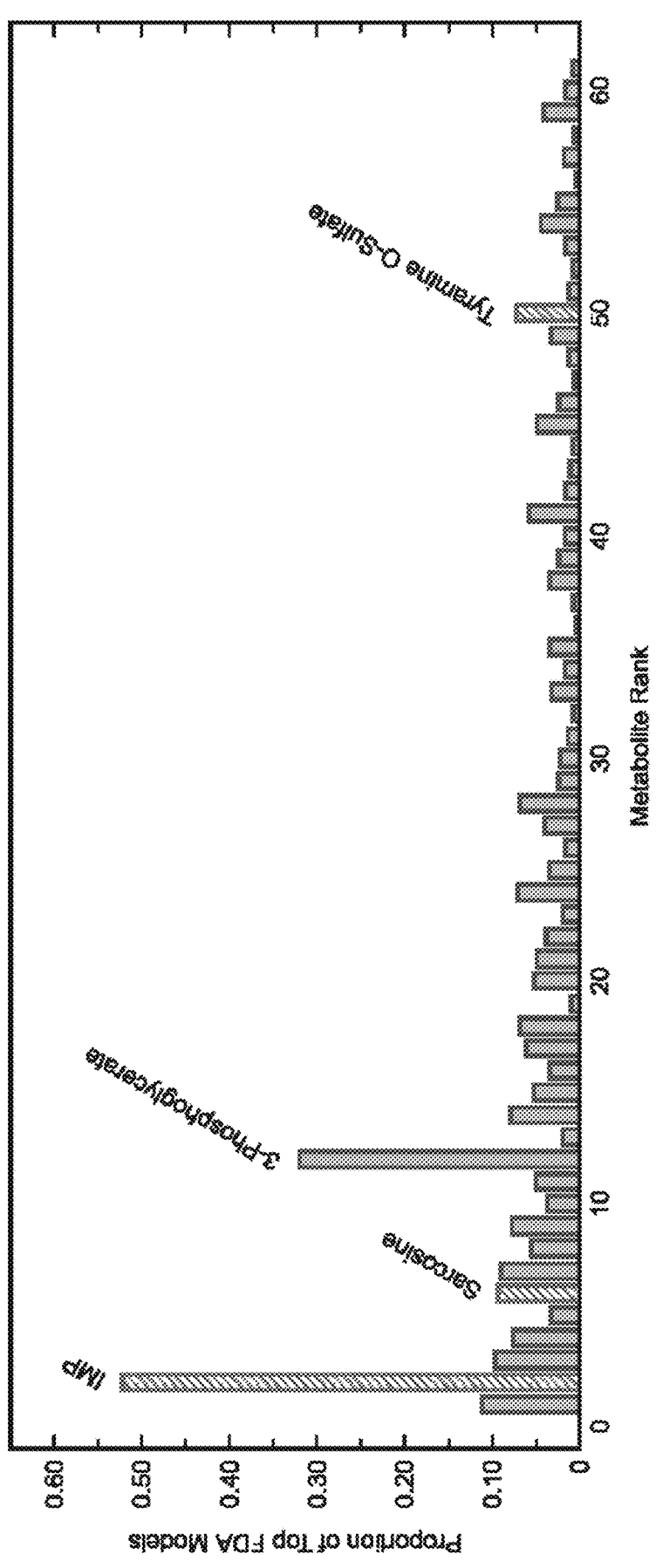
FIG. 10. The frequency of appearance of each of the top plasma metabolites in the top 1000 three-metabolite FDA models. The two metabolites most commonly appearing in the top combinations were inosine 5'-monophosphate (52%) and 3-phosphoglycerate (32%).

It is worth highlighting that many other combinations of metabolites had results comparable to those presented, with the lowest fitted AUROC being 0.97 among the top 1000 combinations of three metabolites. All top 61 metabolites appeared in at least five of the top combinations (FIG. 10), with cysteinylglycine being used the least frequently in only five combinations (0.5%) total. However, 19 metabolites appeared in at least 5% of combinations. The most frequently-used metabolites were IMP (52% of combinations) and 3-phosphoglycerate (32%). Besides IMP, the remaining metabolites comprising the PM3, sarcosine and tyramine O-sulfate, appeared in only 9.3% and 7.2% of combinations, respectively.

The large number of combinations providing good separation between ASD and TD cohorts was likely due to many of the metabolites within the top 61 being highly correlated with one another (Table 14). Sarcosine had the most significant correlations with other metabolites, with the magnitude of the correlation coefficient being as high as 0.96. Tyramine O-sulfate and IMP (maximum correlation coefficients of 0.54 and 0.81, respectively) also had significant correlations with other metabolites. As expected, the three metabolites used in the PM3 were not significantly correlated with each other (i.e., each one likely represents a different set of metabolic differences in ASD).

TABLE 14

The ten metabolites most correlated with each of the three metabolites comprising the PM3, and the correlations between the PM3 metabolites.

| Metabolite | Correlation Coefficient | p-value |
|---|---|---|
| sarcosine | | |
| iminodiacetate (IDA) | 0.96 | <0.001 |
| azelate (nonanedioate, C9) | −0.92 | <0.001 |
| 2-methylserine | 0.91 | <0.001 |
| caproate (6:0) | −0.89 | <0.001 |
| heptanoate (7:0) | −0.88 | <0.001 |
| caprylate (8:0) | −0.86 | <0.001 |
| methylsuccinate | 0.81 | <0.001 |
| nicotinamide riboside | 0.69 | <0.001 |
| N6-acetyllysine | −0.61 | <0.001 |
| N6-methyladenosine | −0.59 | <0.001 |
| tyramine O-sulfate | | |
| valylglycine | 0.54 | <0.001 |
| 1-(1-enyl-oleoyl)-GPE (P-18:1)* | −0.45 | 0.005 |
| 2-oxindole-3-acetate | 0.44 | 0.006 |
| leucylglycine | 0.43 | 0.007 |
| glutamate | −0.37 | 0.023 |
| fructose | −0.36 | 0.026 |
| 2-methylserine | 0.32 | 0.050 |
| caprylate (8:0) | −0.32 | 0.052 |
| 1-stearoyl-GPS (18:0)* | −0.31 | 0.062 |
| azelate (nonanedioate, C9) | −0.30 | 0.070 |
| inosine 5'-monophosphate | | |
| 3-phosphoglycerate | 0.81 | <0.001 |
| indolepropionate | 0.49 | 0.002 |
| nicotinamide riboside | 0.46 | 0.004 |
| leucylglycine | 0.44 | 0.005 |
| 10-undecenoate (11:1n1) | 0.43 | 0.007 |
| 1-linoleoyl-2-arachidonoyl-GPC (18:2/20:4n6)* | 0.41 | 0.010 |
| galactonate | 0.41 | 0.012 |
| 21-hydroxypregnenolone disulfate | −0.38 | 0.017 |
| S-1-pyrroline-5-carboxylate | 0.37 | 0.022 |
| sphingomyelin (d18:1/14:0, d16:1/16:0)* | 0.37 | 0.023 |
| PM3 metabolites | | |
| sarcosine × tyramine O-sulfate | 0.27 | 0.095 |
| sarcosine × inosine 5'-monophosphate | 0.24 | 0.146 |
| tyramine O-sulfate × inosine 5'-monophosphate | −0.00 | 0.985 |

Figure 11A:
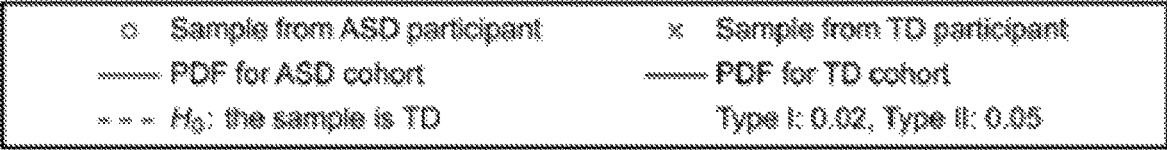
FIG. 11A. FDA using the best combination of three metabolites
Figure 11A:
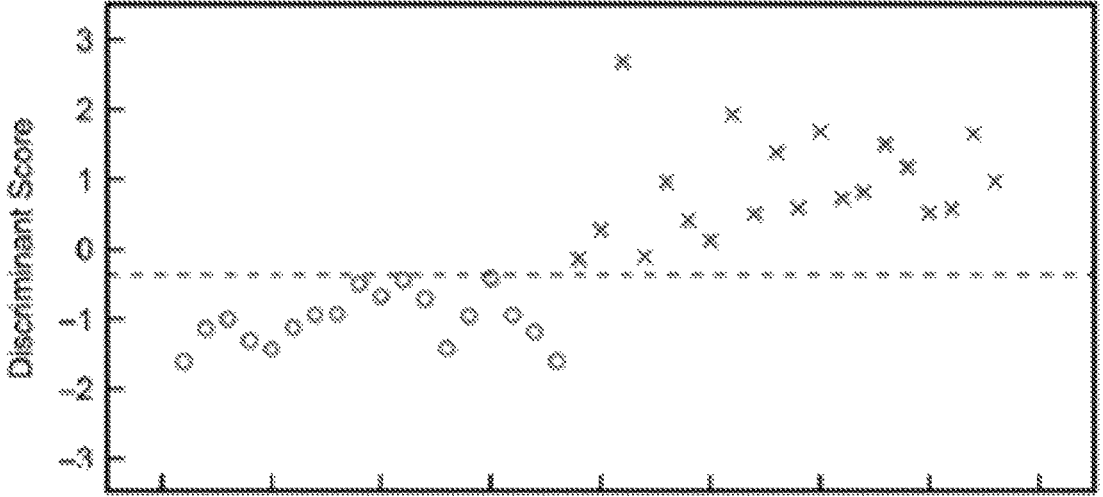
Figure 11B:
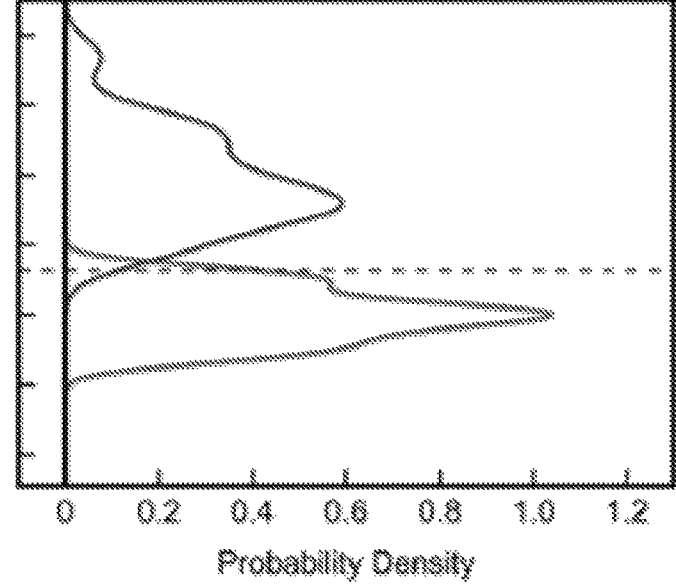
FIG. 11B. FDA using the best combination of three metabolites. PDFs of the fitted scores.
Figure 12A:
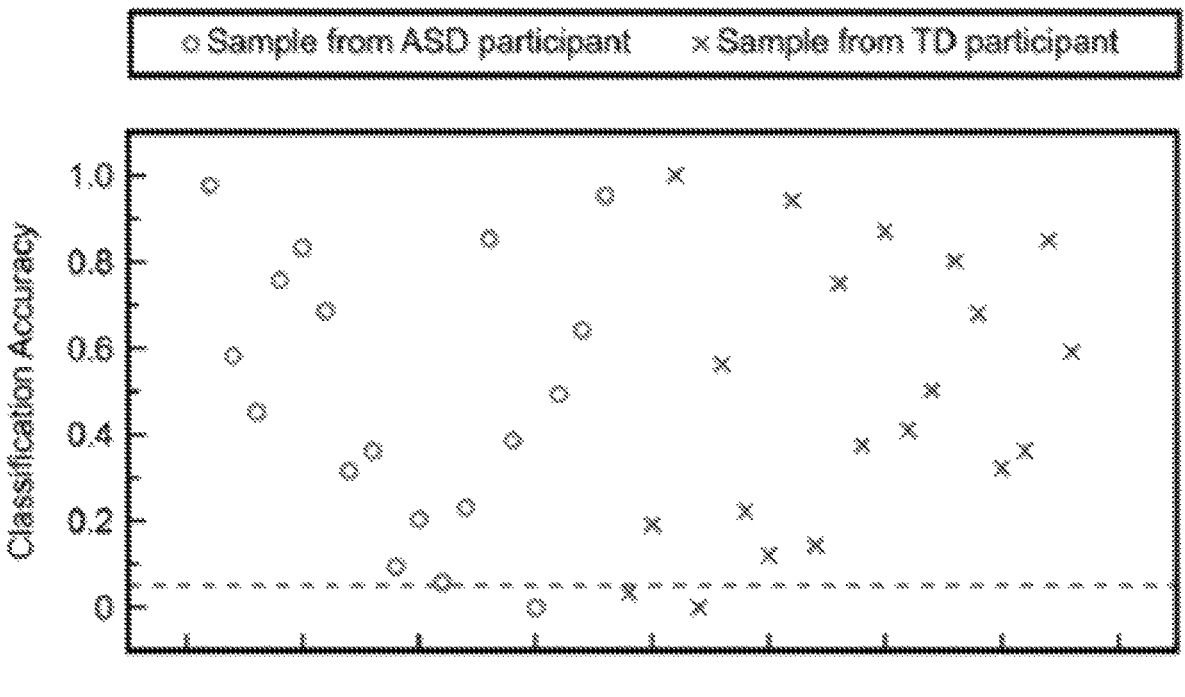
FIG. 12. Classification accuracy (CA) and misclassification error (ME) resulting from cross-validation with the three-metabolite FDA model.
Figure 12B:
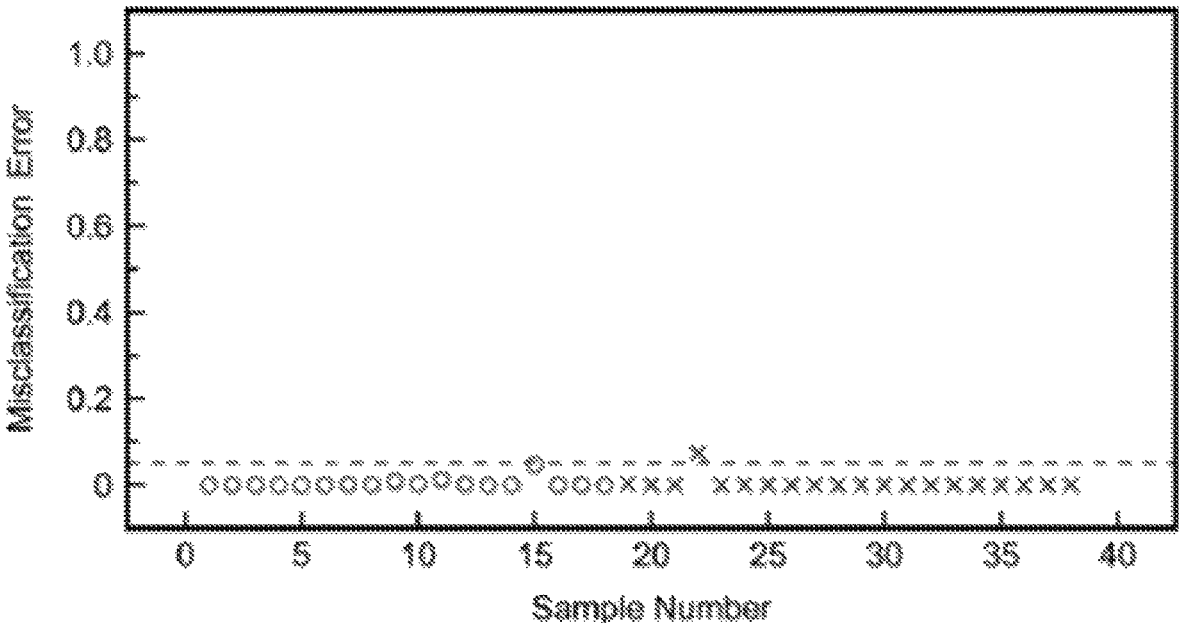

Model fitting and cross-validation. Model fitting with the PM3 metabolites provided good separation between the discriminant scores of the ASD and TD cohorts (FIG. 11A). Setting the classification threshold at $\beta$=0.05 (i.e., Type II error=5%) based on the estimated PDFs yielded a Type I error of 2.0% (FIG. 11B). After leave-one-out cross-validation, there was still good separation in the predicted discriminant scores (FIG. 11C). By classifying samples according to the shown threshold H0, the PM3 achieved a sensitivity of 94% and specificity of 100% after cross-validation (FIG. 11D). Positive and negative predictive values were also high for this classification task. In total, only one participant with ASD was incorrectly predicted by the PM3, and all TD participants were correctly predicted. The majority of samples also had high sample-level CA and low sample-level ME after cross-validation (FIG. 12), indicating overall high confidence for model predictions.

US 12,669,511 B2

37 38

Model Application on MTT Time Points

Figure 13A:
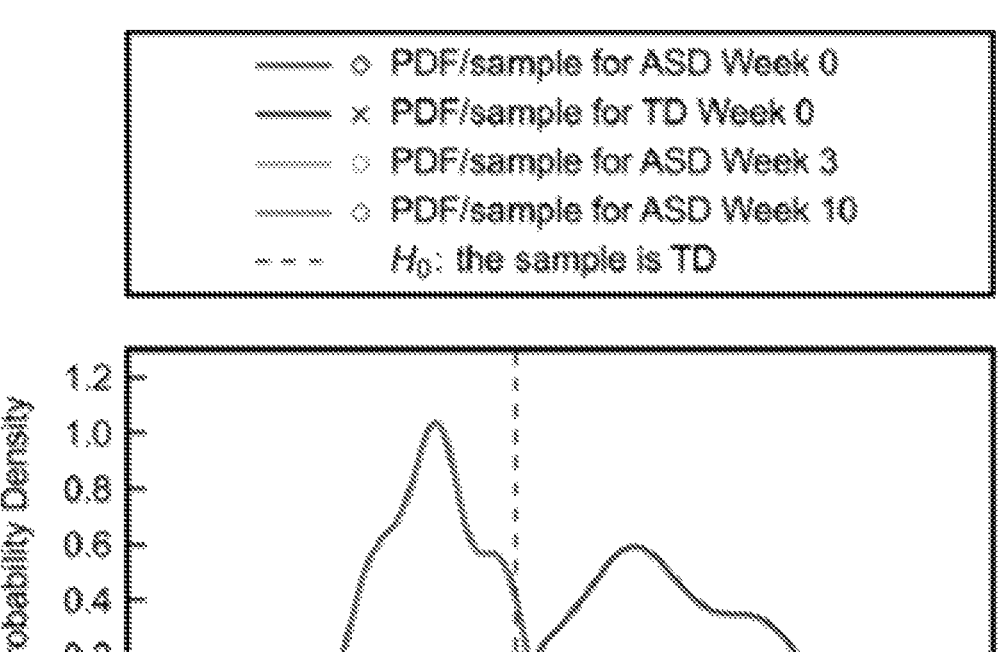
FIG. 13A. Discriminant scores and their PDFs for the baseline Week 0 ASD and TD cohorts.
Figure 13B:
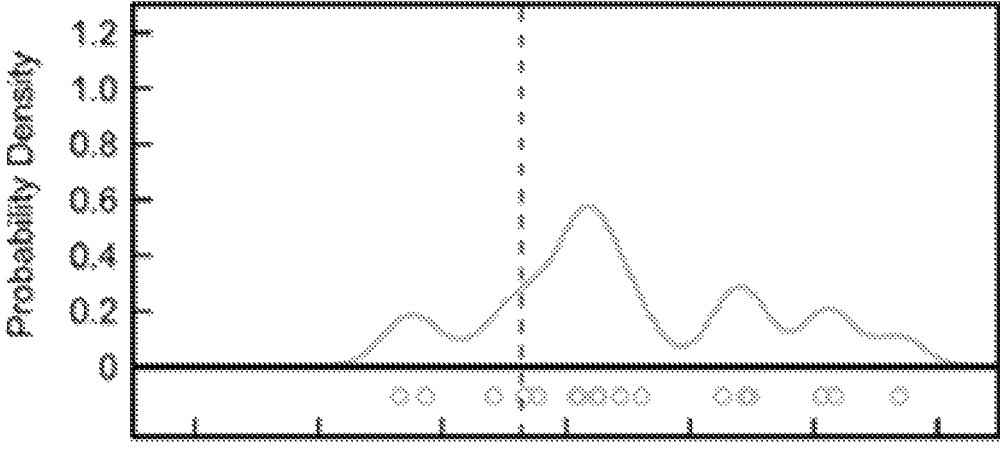
FIG. 13B. Discriminant scores and their PDFs the Week 3 ASD cohort.
Figure 13C:
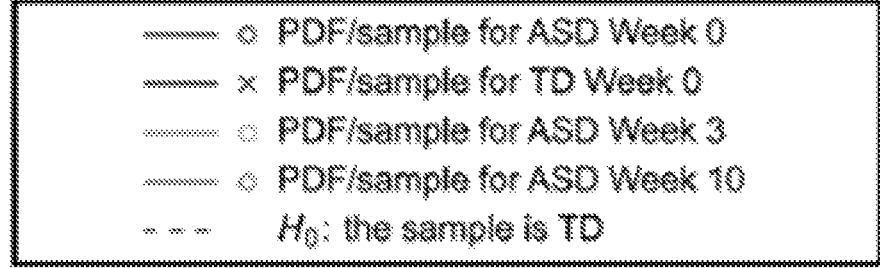
FIG. 13C. Discriminant scores and their PDFs for the Week 10 ASD cohort. It should be noted that one ASD sample at Week 10 had a score of 17.9 and is not plotted since it is off the scale (strongly in the TD range).
Figure 13C:
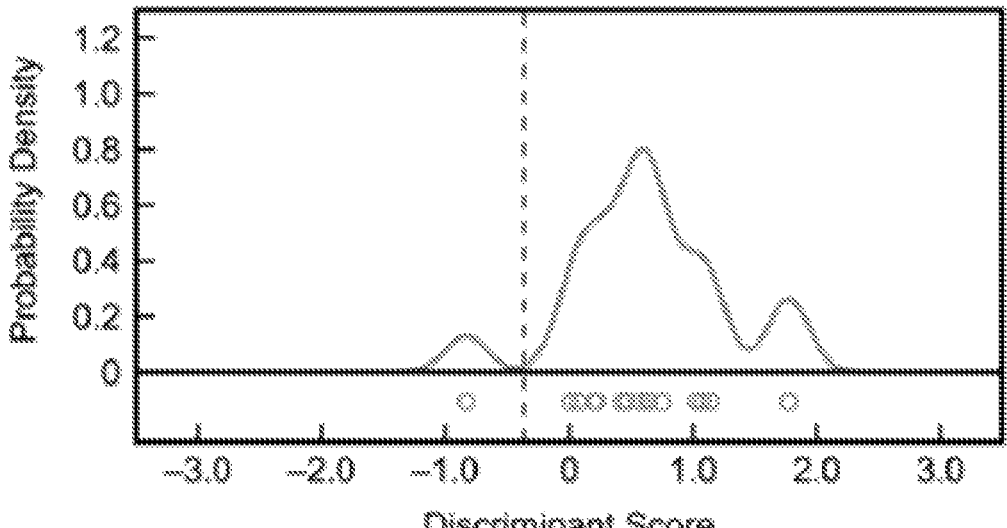
Figure 14A:
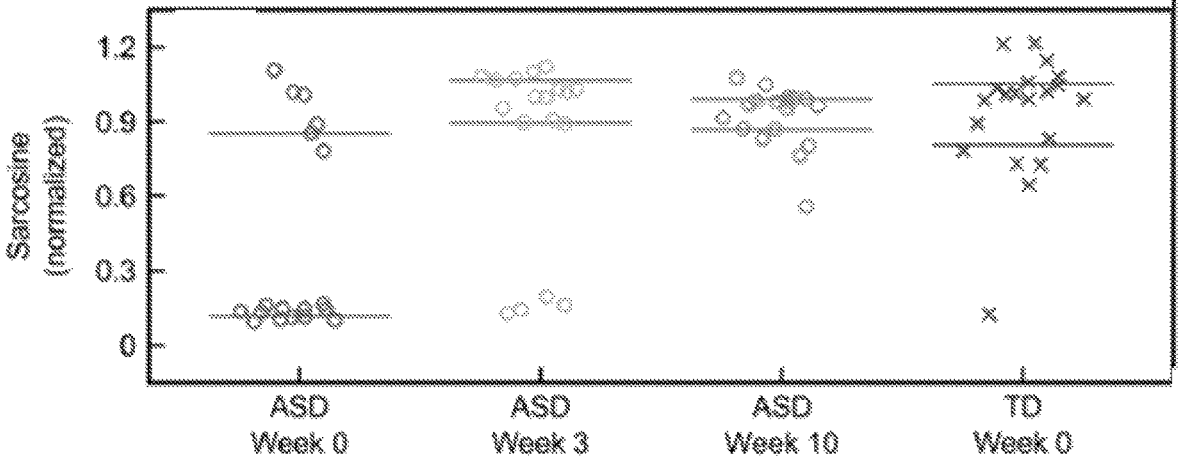
FIG. 14A. Normalized values of the three PM3 metabolites in the TD cohort at baseline and the ASD cohort before and after MTT for sarcosine. The metabolite was normalized such that the median value was one in the TD cohort. The 25th and 75th percentiles for each group's metabolite values are indicated by the grey bars.
Figure 14B:
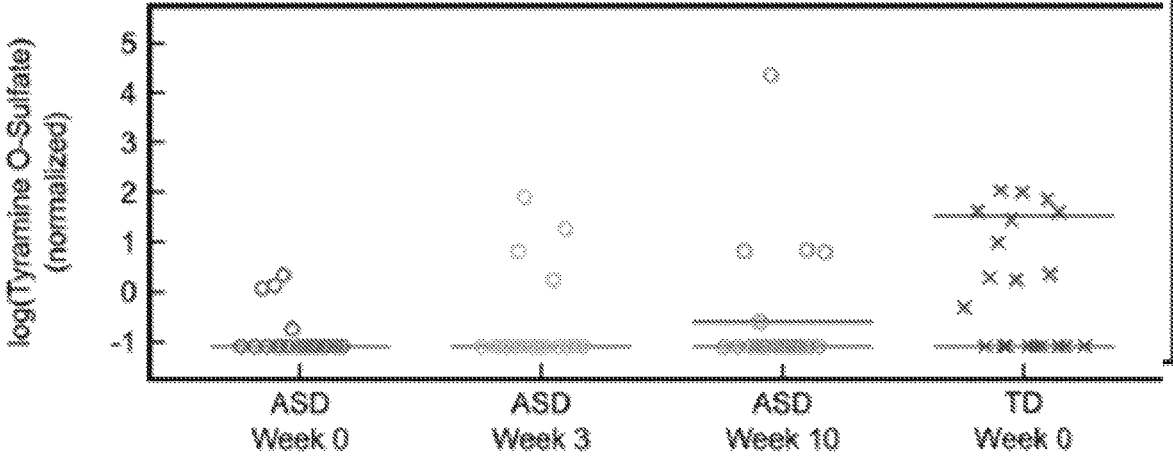
FIG. 14B. Normalized values of the three PM3 metabolites in the TD cohort at baseline and the ASD cohort before and after MTT for tyramine O-sulfate. The metabolite was normalized such that the median value was one in the TD cohort. The 25th and 75th percentiles for each group's metabolite values are indicated by the grey bars. Note that values for tyramine O-sulfate are plotted on a logarithmic scale.
Figure 14A:
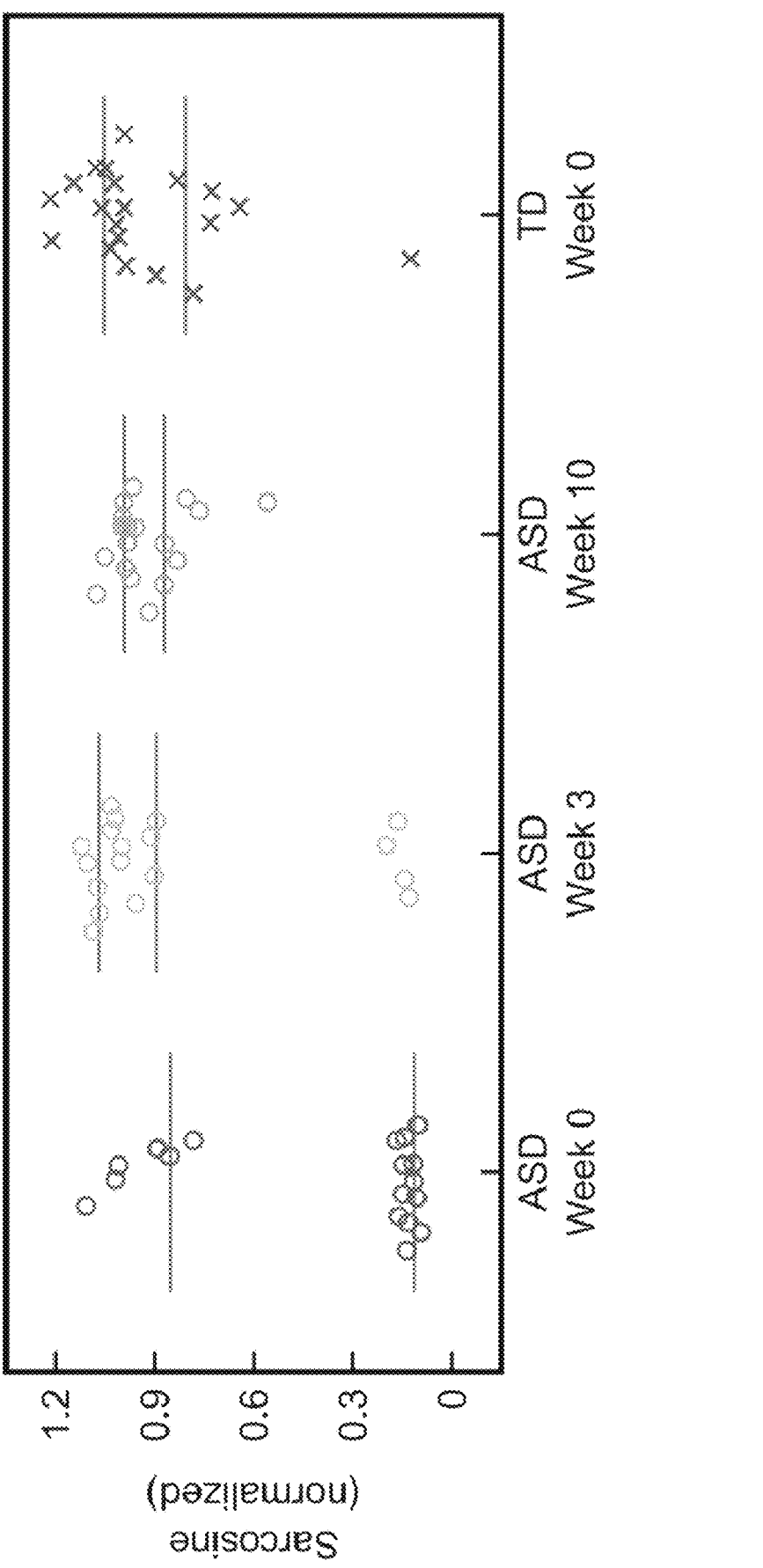
Figure 14B:
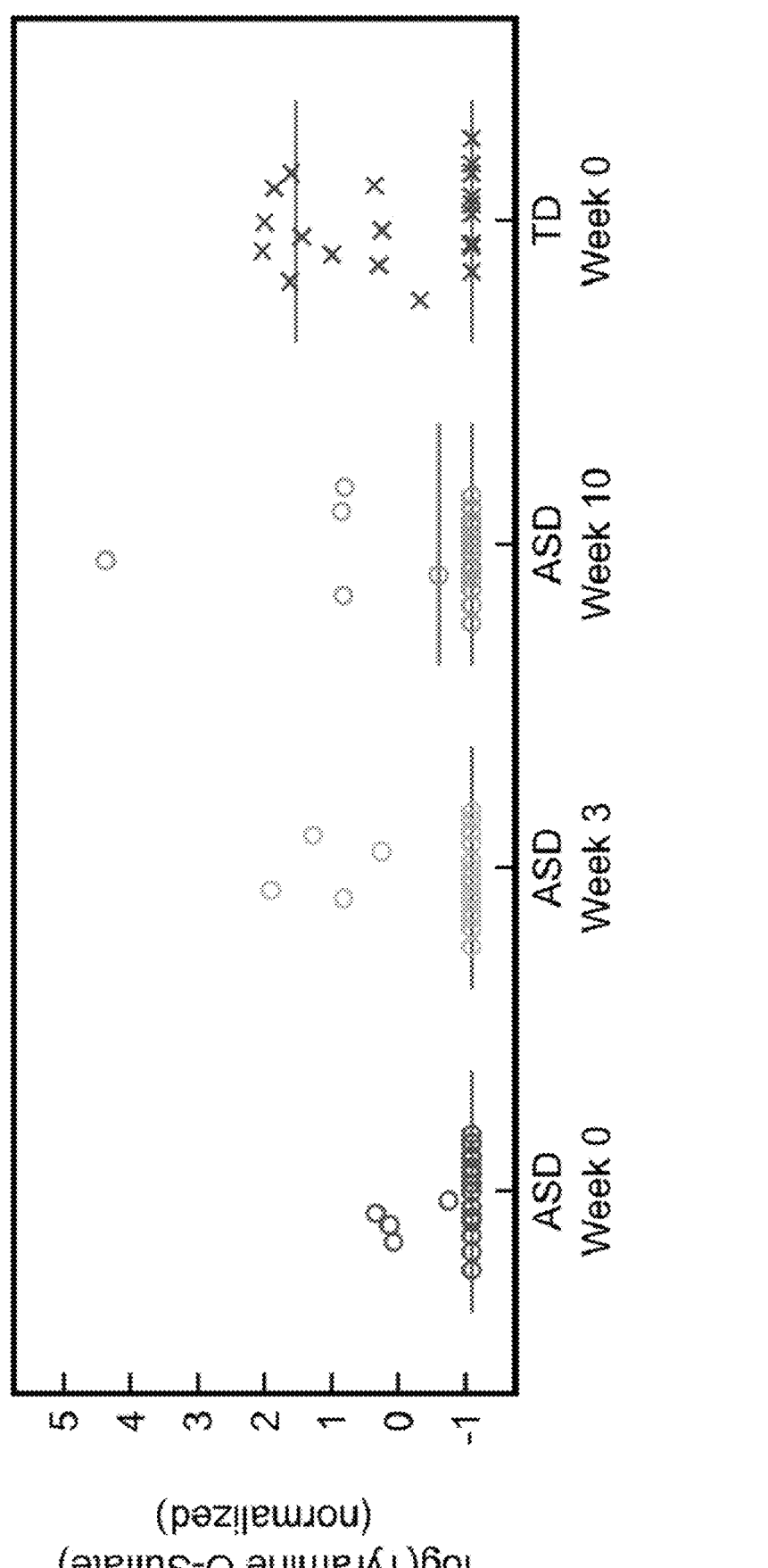
Figure 14C:
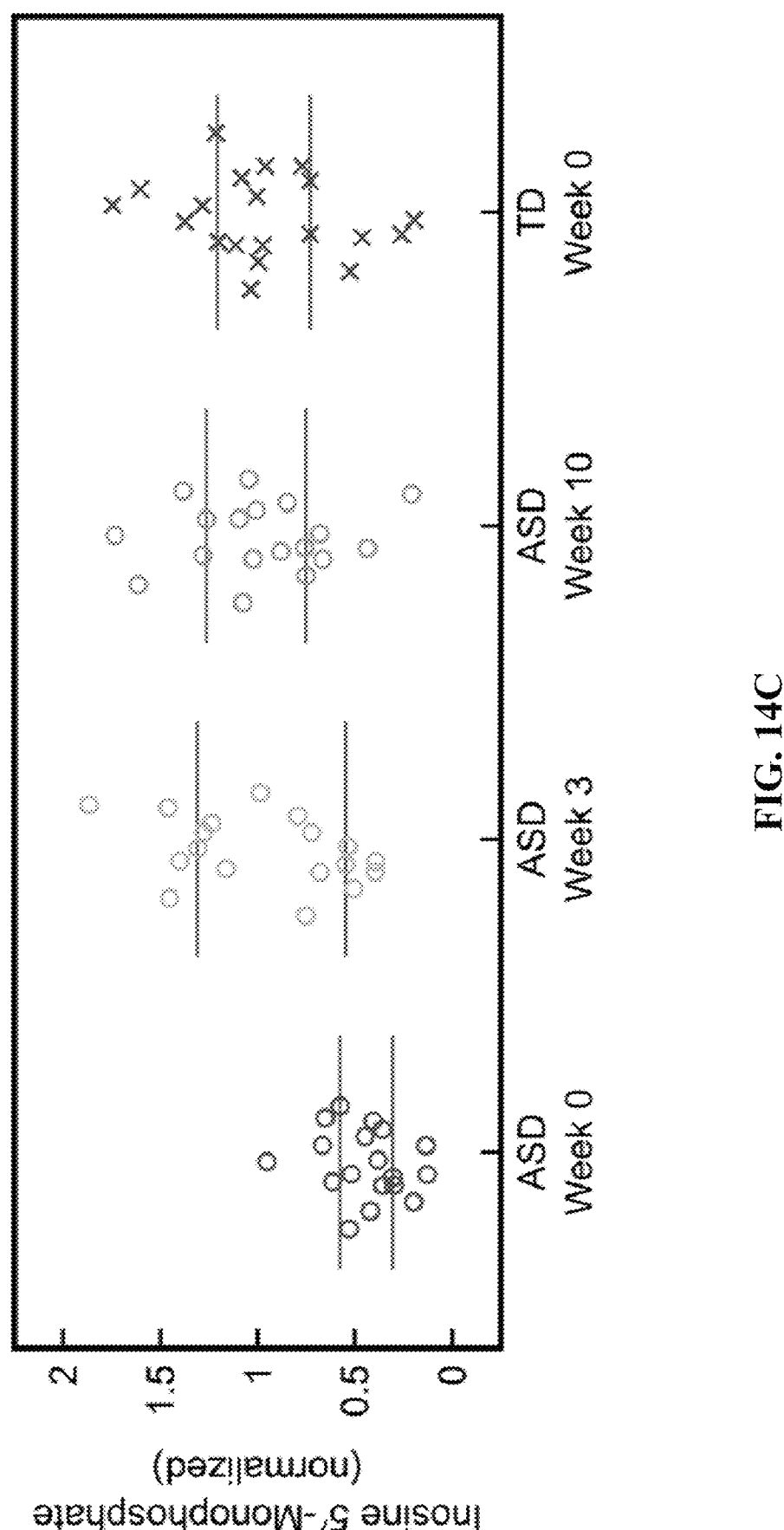
FIG. 14C. Normalized values of the three PM3 metabolites in the TD cohort at baseline and the ASD cohort before and after MTT for inosine 5'-monophosphate. The metabolite was normalized such that the median value was one in the TD cohort. The 25th and 75th percentiles for each group's metabolite values are indicated by the grey bars.

Application of the PM3 on the plasma metabolite data at Week 3 and Week 10 of MTT revealed an overall shift of the treated ASD participants towards the TD distribution (FIG. 13A-C). After three weeks of treatment, median concentrations of two of the PM3 metabolites (sarcosine and IMP) changed from 15% and 41%, respectively, of the median TD values to 100% and 89% of the median TD values; after ten weeks of treatment, the medians were at 97% and 102% of the median TD values. In other words, MTT therapy rapidly improved those two plasma metabolites, and they remained improved at ten weeks of therapy (Table 15, FIG. 14A-C). In contrast, the other PM3 metabolite (tyramine O-sulfate) started at 34% of the median TD value and overall remained unchanged at Week 3 and Week 10 (with the majority of values being below the detection limit), although a small number of samples shifted further into the TD range at later time points. From a classification standpoint, the Type II error (percent of the ASD distribution being classified as TD) at Week 3 increased to 80% after being just 5% at baseline, but the effect size for this shift was not significant (Table 15). At Week 10, the Type error increased further to 94% and the effect size became statistically significant. These increases in Type error can be interpreted as the ASD cohort after treatment becoming much more metabolically similar to the TD cohort. It should be noted that one participant from the ASD cohort at Week 10 had an exceptionally large discriminant score (17.9) and is not shown in the plot since it is off the scale, but was still factored into the numerical calculations.

individuals with ASD from TD individuals. One of the most promising combinations of metabolites, the PM3, was able to classify ASD with 94% sensitivity and 100% specificity after cross-validation. This multivariate approach achieved a level of separation between the ASD and TD cohorts that could not be attained by using the individual metabolites by themselves.

Many of the top metabolites were found to be significantly correlated with each other, possibly due to these metabolites coming from the same or closely connected metabolic pathways. Multivariate approaches such as FDA are appropriate for addressing correlations in biological networks (Vargason, Howsmon, McGuinness, & Hahn, 2017) and do not require that the relationships between measurements be specified or well-defined. By identifying metabolites for use in the PM3 that were largely uncorrelated, it is possible to maximize the amount of useful information with a minimal number of metabolites. Further investigation of the biological significance of these metabolites and the metabolites they are correlated with may be warranted.

Classification performance of the PM3 was evaluated with leave-one-out cross-validation, which supported the classifier's ability to generalize to independent data sets. Although implementing other methods of cross-validation such as k-fold cross-validation may help to further support these conclusions (especially given the large panel of metabolites involved), the small sample size introduces limitations with respect to how much the data set can be partitioned without approaching very small sample sizes in

TABLE 15

Changes in key metabolite concentrations, discriminant scores, Type II errors, and effect sizes at different MTT time points. Metabolite concentrations presented here are normalized such that the median value is 1 in the TD group at Week 0. Discriminant scores are from the PM3 model fitted to Week 0 data and then applied to Week 3 or Week 10 data. Type II error was calculated based on the determined threshold for $H_0$. The effect size was the median change in discriminant score at each MTT time point with respect to baseline, where each individual's score after treatment was paired with their baseline score.

| Statistic | ASD Week 0 | ASD Week 3 | ASD Week 10 | TD Week 0 |
|---|---|---|---|---|
| Sarcosine ($25^{th}/75^{th}$ percentile) | 0.15 (0.12, 0.85) | 1.00 (0.89, 1.07) | 0.97 (0.87, 0.99) | 1.00 (0.81, 1.05) |
| Tyramine O-sulfate ($25^{th}/75^{th}$ percentile) | 0.34 (0.34, 0.34) | 0.34 (0.34, 0.34) | 0.34 (0.34, 0.55) | 1.00 (0.34, 4.59) |
| Inosine 5'-monophosphate ($25^{th}/75^{th}$ percentile) | 0.41 (0.30, 0.57) | 0.89 (0.55, 1.31) | 1.02 (0.75, 1.26) | 1.00 (0.73, 1.21) |
| Median discriminant score ($25^{th}/75^{th}$ percentile) | −0.97 (−130, −0.70) | 0.25 (−0.23, 1.45) | 0.64 (0.22, 1.07) | 0.78 (0.46, 1.44) |
| Type II error | 5% | 80% | 94% | — |
| Effect size (95% confidence interval) | — | 1.40 (0.79, 2.05) | 1.85 (1.45, 2.06) | — |

Univariate analysis of plasma metabolites revealed that many individual metabolites could modestly differentiate between the ASD and TD cohorts, with 61 metabolites yielding an AUROC of at least 0.7 and the highest AUROC of 0.89 associated with nicotinamide riboside. However, none of these showed sufficient individual separation to be used as biomarkers for accurately distinguishing the two groups. This is in contrast to multivariate modeling with FDA, which was able to identify many combinations of metabolites that could be used to accurately distinguish those partitions. A true validation set containing new ASD and TD participants (without any treatment) would help to further evaluate the performance of the PM3 and alleviate potential concerns of overfitting, which is still not completely ruled out here given the small number of samples and large initial number of metabolites to choose from. The application of the model to the MTT Week 3 and Week 10 data for participants with ASD suggests that it may be a useful biomarker of treatment efficacy, and that major changes in metabolites associated with ASD and/or GI symptoms did occur, consistent with reported improvements in ASD and GI symptoms after treatment.

For the three PM3 metabolites, it is interesting to note that sarcosine at baseline had a strongly bimodal distribution, with most children with ASD having very low levels (15% of the median of the TD group), but with several in the normal range. After MTT they were all in the normal range. Conversely, the distribution of IMP was unimodal and broadly low in the ASD group, and clearly improved after treatment. The majority of values for tyramine O-sulfate (78%) were below the detection limit in the ASD cohort at baseline, and at Week 3 and Week 10 there were still 78% and 72% of samples below the detection limit, respectively. In contrast, less than half of the values for tyramine O-sulfate (45%) were below the detection limit at baseline in the TD cohort. The lack of improvement in this metabolite after MTT may indicate it (and/or correlated metabolites) as a target for future interventions to further improve the metabolic profiles of children with ASD.

Previous work by the inventors revealed that plasma markers of DNA methylation and oxidative stress from the folate-dependent one-carbon metabolism (FOCM) and transsulfuration (TS) pathways could be used to predict ASD status with 98% sensitivity and 96% specificity. Multivariate analysis of FOCM/TS markers has also been found to provide an indication of metabolic and behavioral improvement resulting from clinical interventions. The current panel of metabolites is not directed specifically at these pathways, but was used to achieve (preliminary) results comparable to those obtained using targeted FOCM/TS measurements. That being said, several metabolites appearing in the list of top 61 metabolites, such as sarcosine, cysteinylglycine, and glutamate, do have roles in FOCM and/or TS, and sarcosine was further included as one of the three measurements in the PM3. Plasma metabolomics studies may further target additional markers from FOCM/TS to further explore the validity of these quantities for accurately classifying ASD.

In studies such as this where the prevalence of ASD in the study sample does not match the prevalence of ASD in the overall population, the classifier's positive and negative predictive values may be incorrectly represented with respect to its true clinical values. To gain an indication of the classifier's true clinical utility, the Bayes' adjusted positive and negative predictive values is calculated by incorporating the true population prevalence. Without adjusting for prevalence, the positive and negative predictive values of the PM3 were 100% and 95%, respectively. After adjusting for ASD population prevalence, assuming the current U.S. prevalence estimate of 1.7%, the positive predictive value remains 100% and the negative predictive value increases to 99%. There is thus minimal mismatch between the predictive values of the PM3 in the study population and the adjusted estimates for the general population.

This study demonstrates metabolic markers for distinguishing ASD children with GI symptoms from TD children without GI symptoms. In particular, the combination of the three metabolites sarcosine, tyramine O-sulfate, and IMP are notable for ability to distinguish ASD children with GI symptoms from TD children without GI symptoms. The model developed from these three metabolites was applied to the ASD group after three and ten weeks of Microbiota Transfer Therapy, and it was found that during and after treatment there was much less difference between the PM3 discriminant scores of the two groups, consistent with significant improvements in ASD and GI symptoms in the ASD treatment group. Two of the PM3 metabolites, sarcosine and IMP, improved substantially during and after MTT, but one of them (tyramine O-sulfate) did not change notably, and hence it (and the metabolites it is correlated with) may be a target for future therapies.

Example 7: Further Study: Distinct Fecal and Plasma Metabolites in Children with Autism Spectrum Disorders and their Modulation after Microbiota Transfer Therapy This study reports further comprehensive metabolite measurements from children who participated in a prior MTT study. Specifically, fecal and plasma samples were measured at baseline in children with ASD with chronic GI problems (chronic constipation and/or diarrhea) vs. TD children without GI issues to determine which metabolites were different in the ASD group before treatment. In addition, similar measurements of fecal and plasma metabolites were made at multiple time points during and at the end of MTT in the ASD group, and compared with the TD group to record changes in metabolites as a consequence of the microbiome-based treatment.

Methods

Study design and protocol was as approved described in detail in: Kang, et al. as referenced herein above. In summary, 18 children with ASD and 20 typically developing children participated in the study. All 18 children with ASD were 7-16 years old and completed the 18 weeks of the open-label trial, consisting of antibiotic (vancomycin) treatment for 2 weeks, a bowel cleanse for one day (MoviPrep), a proton pump inhibitor (Prilosec) throughout the trial, and Standardized Human Gut Microbiota of high-dose for one or two days followed by maintenance-dose for 7-8 weeks. We monitored participants during the 10 weeks of treatment as well as 8 weeks after MTT stopped. There were no major adverse effects. Substantial improvement was observed in their GI and ASD symptoms and an increase in microbiome diversity. Further information on the clinical and microbial observations are available in Kang et al. referenced above. Sample Collection for Metabolomic Analysis For metabolomic analysis, plasma samples were collected at baseline, week 3 (after the vancomycin and bowel cleanse, and just before the first dose of microbiota), and week 10 (the end of MTT treatment). Phlebotomists collected plasma samples in the morning from fasting participants and froze samples immediately in dry ice. Frozen samples were stored in a −80° C. freezer until all samples were collected. Plasma samples were collected from all 18 children with ASD at three time points except for one missing sample at week 3. Plasma samples were collected from all 20 TD participants at baseline only, since they did not receive MTT. To be consistent with microbial analysis, we used the same fecal samples collected at baseline, week 3-4 (approximately 6 days after the initial high dose of microbiota), week 10, and week 18 (8 weeks after the end of MTT) for children with ASD and baseline for typically developing children. Once the clinical trial concluded, aliquots of all the frozen samples were sent overnight with dry-ice to Metabolon (Durham, North Carolina, USA) for metabolomic analysis. In order to avoid any bias in metabolomics measurement, we randomized and blinded all autism and control samples in a random order before shipping out to Metabolon.

Metabolomic Analysis and Sample Normalization

At Metabolon, a platform with the ultrahigh performance liquid chromatography-tandem mass spectroscopy (UHPLC-MS/MS) instruments was employed. Metabolomic measurements consisted of sample extraction/preparation, quality assurance/quality control, and UHPLC-MS/MS. A detailed description can be found in Long et al., *Whole-genome sequencing identifies common-to-rare variants associated with human blood metabolites*, Nature Genetics 49(4): 568 (2017). Metabolite quantitation was performed by peak area integration using area-under-the-curve, and the intensity measurements yielded relative abundance of each metabolite. Missing values were imputed with the lowest value of each compound measurement divided by the square root of 2. With the metabolomics datasets after imputation, we normalized those relative abundances into Z-scores which is a dimensionless quantity to obtain a mean value of 0 and standard deviation of 1 for each individual metabolite. The Z-score indicates how many standard deviations the observation is above or below the mean and is useful to compare observations coming from different distributions of individual metabolites. Throughout the following disclosure these values are referred to as normalized relative abundance and all data is reported comparing the two groups as normalized relative abundance. To calculate the ratio of the ASD group at different sampling points to TD groups at baseline (ASD/TDbaseline), each metabolite value was normalized such that the median value was set to a value of 1.0 in the TD cohorts.

Bioinformatics and Statistical Analysis

In order to elucidate metabolite profiles as a group, heatmap analysis and principal component analysis (PCA) were performed using the MetaboAnalyst 4.0, as described for example in Chong, J., et al., *MetaboAnalyst 4.0: towards more transparent and integrative metabolomics analysis*, Nucleic Acids Research, 46(W1): W486-W494 (2018). In order to investigate how metabolites were potentially inter-related with the improvement of GI- and behavioral symptoms, co-occurrence network analysis was performed by calculating Spearman correlation tests for all plasma metabolites and clinical measurements. Only correlations with adjusted p value less than 0.1, after correcting for multiple hypotheses in the co-occurrence network were considered. Cytoscape was used to visualize the co-occurrence network (Lopes, C. T., et al., *Cytoscape Web: an interactive web-based network browser*. Bioinformatics 26(18): 2347-48 (2010)).

Using 16S rRNA gene amplicon sequencing data from the original study (Kang et al.), microbial functions were predicted using PICRUSt v.1.1.3, HUMAnN v0.99, and LEfSe analyses available in the online Galaxy version of the Huttenhower Lab (v1.0.0). Through PICRUSt, predicted metagenome files containing gene counts were obtained, and then PICRUSt output to HUMAnN employed to obtain gene and pathway summaries based on Kyoto Encyclopedia of Genes and Genomes (KEGG) modules. In order to investigate which bacterial functional module is associate with ASD phenotype, a linear discriminant analysis with effect size (LEfSe) was performed, where the non-parametric factorial Kruskal-Wallis (KW) sum-rank test was used to detect significantly different genomic features with respect to the class of interest—ASD, and then Linear Discriminant Analysis (LDA) was used to estimate the effect size of each individually abundant feature.

Assumed was that the metabolomic and 16S rRNA gene sequencing data was non-normally distributed because of a relatively small sample size and the following were employed: nonparametric statistical tests with Mann-Whitney U-test, Wilcoxon signed-rank test, Spearman correlation test, and KW sum-rank test. For metabolomic and genomic features with hypotheses, un-adjusted p values lower than 0.05 were accepted as significant. For exploratory metabolites, p values were adjusted by correcting for multiple hypotheses with Benjamini-Hochberg and Leave-One-Out methods and adjusted p values less than 0.05 were considered statistically significant. For paired data (before and after MTT treatment in the same participants), the Wilcoxon signed-rank test and 1-tailed test were employed, since the hypothesis was that the direction of either increase or decrease of normalized relative abundance based on the measurements at baseline.

Results

Plasma Metabolite Profiles in ASD Vs. TD Changed after MTT

Figure 15A:
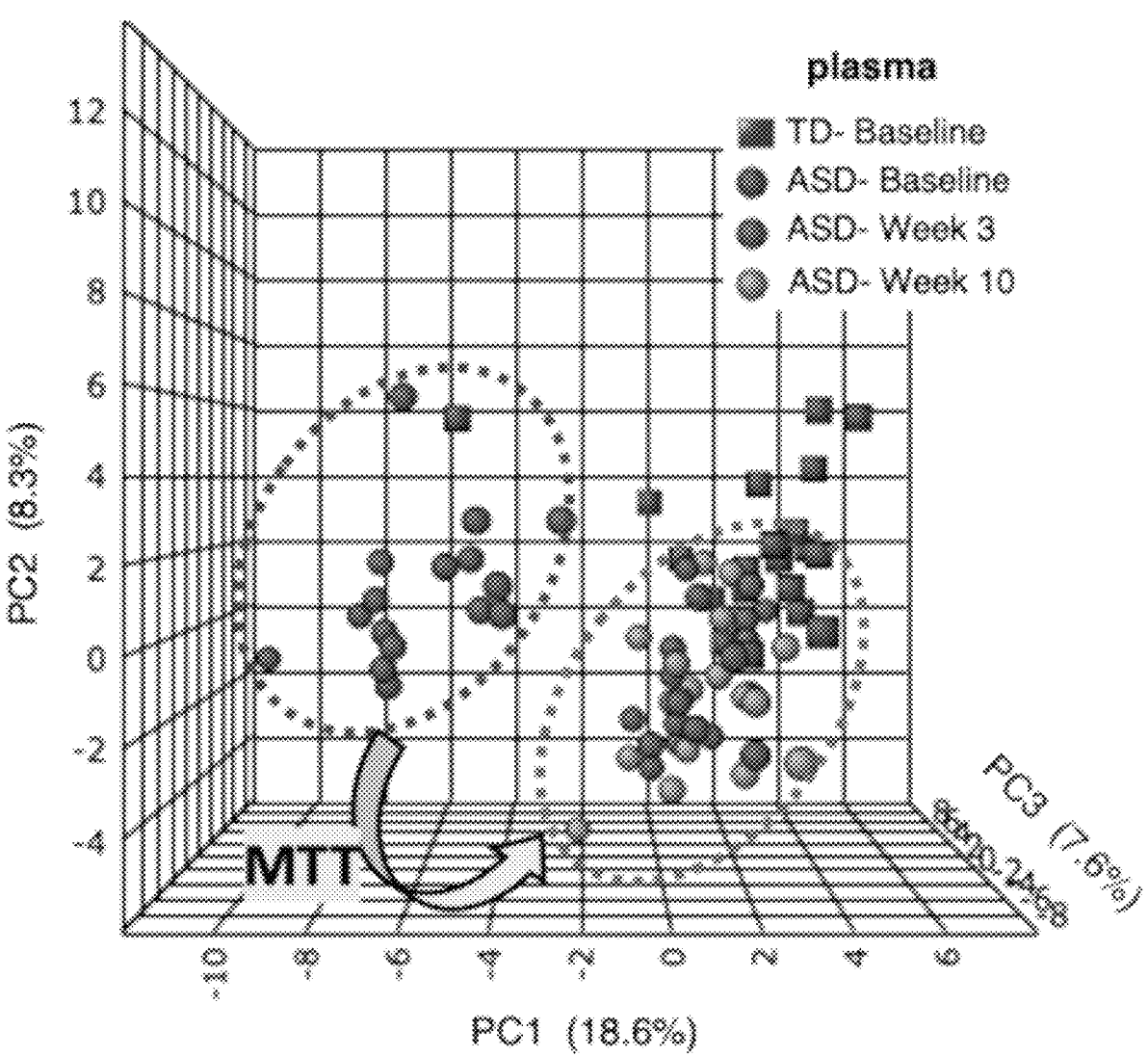
FIG. 15A. Principal component analysis (PCA) with plasma samples at different time points.

LC-MS assay identified a total of 619 metabolites in plasma sample. To evaluate differences in metabolite profiles as a group, a heatmap was generated and a PCA performed using the 73 plasma metabolites whose levels were relatively different at baseline between two groups (un-adjusted $p<0.05$). FIG. 15A displays the results of PCA for each participant in the ASD group at 3 time points, and for the TD group. The plot shows that the ASD group cluster was largely separated from the TD group cluster at baseline (12 of 18 ASD samples in leftmost cluster, whereas the TD group is in the rightmost cluster). After vancomycin (at 3 weeks), the ASD group shifted towards the TD group (only 4 of 18 in leftmost cluster) and further shifted towards the TD group after MTT at week 10 (0 of 18 in leftmost cluster) (FIG. 15A).

Figure 15B:
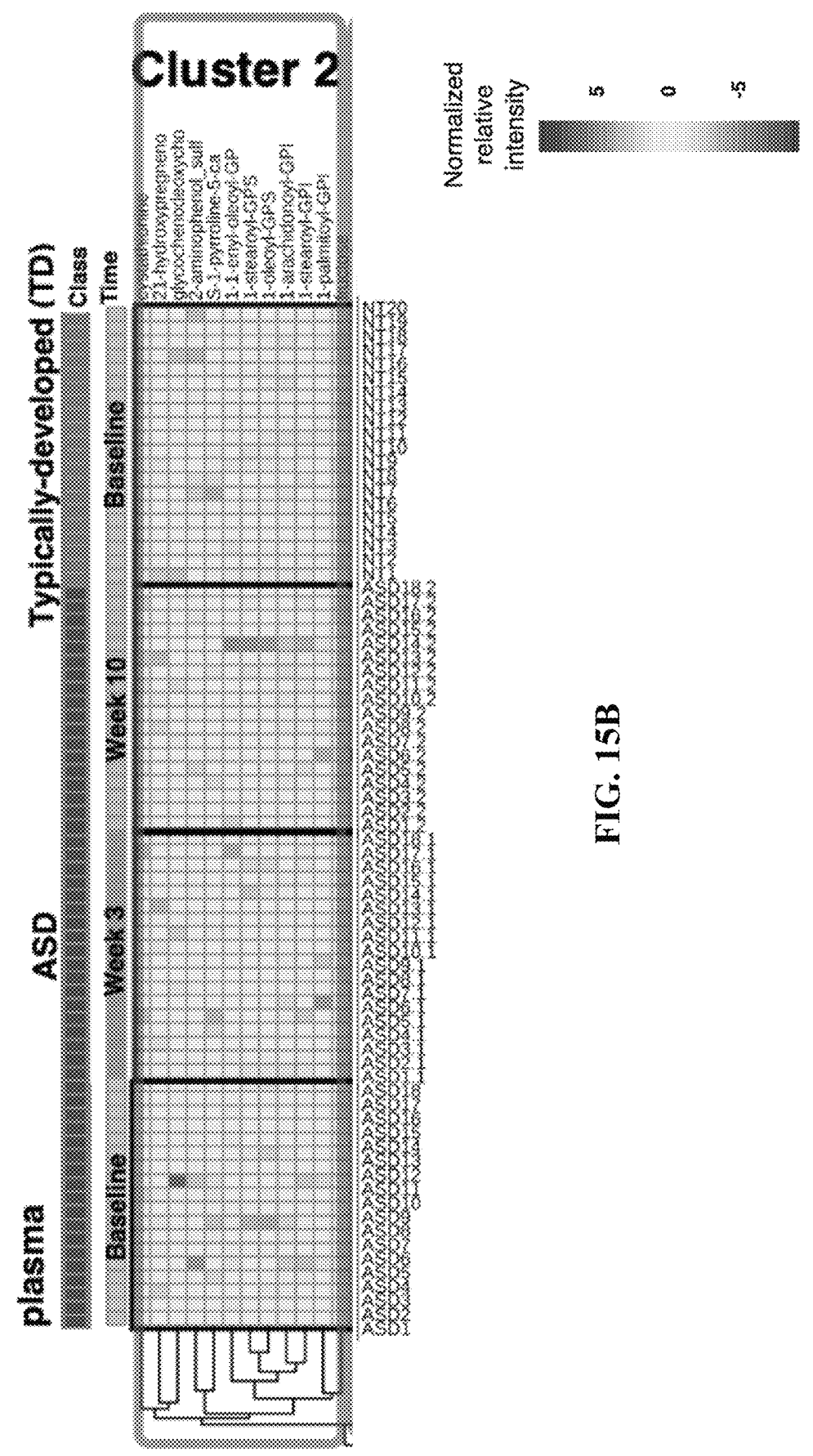
FIG. 15B. Heatmap profile with dendrogram with plasma samples at different time points.

To further evaluate changes in metabolite profiles, a heatmap and was generated and a PCA performed using the 73 plasma metabolites whose levels were relatively different at baseline between the two groups (un-adjusted $p<0.05$). The heatmap presented in FIG. 15B shows the metabolites' normalized relative abundance for the ASD group at three different time points, and the normalized relative abundance of the TD group at baseline. As shown in the heatmap with dendrogram in FIG. 15B, the 73 plasma metabolites were clustered into two groups, based on whether they were initially higher (clusters 1 and 2) or lower (clusters 3, 4, and 5) in ASD at baseline. Cluster 1 (FIG. 15B) included 23 metabolites which displayed higher levels of normalized relative abundance in ASD samples at baseline and became more similar to levels in TD samples after MTT at week 10. Cluster 2 included 12 metabolites that were initially higher in the ASD samples but did not change significantly after treatment. Clusters 3 and 4 (defined identical but placed separate in FIG. 1*b*) consisted of 25 metabolites which were lower in the ASD samples at baseline and increased after MTT. Metabolites in Cluster 5 were lower at baseline but unchanged after MTT.

Individual Metabolite Levels in ASD Plasma Samples were Significantly Different at Baseline Among a total of 619 metabolites in our plasma samples, hypothesis-driven analysis was performed on metabolites that have previously reported as abnormal in either human or animal model studies of ASD. Hypothesized was that the relative abundance of these metabolites was going to be either higher or lower when compared to TD. Those metabolites are shown in Table 16 (baseline) and Table 17 (baseline, after vancomycin at week 3, and after MTT at week 10) and include neurotransmitters (such as glutamate, GABA, dopamine, and serotonin), tyrosine/tryptophan derivatives (such as p-cresol, 4-ethylphenyl sulfate (4-EPS), and indole), and antioxidants (such as glutathione, biliverdin and bilirubin). For these metabolites, multiple hypotheses correction was not employed, but un-adjusted Mann-Whitney U tests relied upon to determine their significance, i.e., results were accepted as significant if un-adjusted $p < 0.05$. Among the list, the level of normalized relative abundance was significantly higher for glutamate and significantly lower for tyramine O-sulfate, indolepropionate, biliverdin, and bilirubin in the ASD group at baseline (two-tailed un-adjusted $p < 0.05$), which were consistent with what was expected, except tyramine O-sulfate (Table 16). The other metabolites listed in Table 16 were not significantly different between the two groups. After MTT at week 10, glutamate and indoleproprionate shifted to closer to the levels in the TD group, but the other metabolites (tyramine O-sulfate, bilirubin, and biliverdin) did not change significantly after treatment (one-tailed Wilcoxon signed-rank test $p < 0.03$, Table 17). Note that bilirubin and biliverdin are highly correlated with one another (r=0.93)

TABLE 16

Normalized plasma metabolites (hypothesized at the beginning of the study) and their median values of ASD and typically-developing (TD) samples at baseline. p values are written in bold when they are less than 0.05 by two-tailed Mann-Whitney U test (no correction for multiple hypotheses).

| SUPER PATHWAY | SUB PATHWAY | BIOCHEMICAL | un-adj. p value | Median ASD | Median TD |
|---|---|---|---|---|---|
| Amino Acid | Glutamate Metabolism | glutamate | 0.03 | 0.13 | −0.32 |
| | | glutathione,_oxidized_(GSSG) | 0.88 | 0.05 | −0.34 |
| | Phenylalanine and Tyrosine Metabolism | 4-ethylphenyl_sulfate | 0.09 | −0.32 | −0.28 |
| | | dopamine_sulfate_(2) | 0.84 | −0.53 | −0.43 |
| | | p-cresol_sulfate | 0.71 | −0.05 | 0.04 |
| | | tyramine_O-sulfate | 0.01 | −0.20 | −0.13 |
| | Tryptophan Metabolism | indolepropionate | 0.01 | −0.69 | −0.21 |
| | | serotonin | 0.63 | 0.02 | −0.19 |
| Cofactors and Vitamins | Hemoglobin and Porphyrin Metabolism | bilirubin | 0.01 | −0.32 | 0.09 |
| | | bilirubin_(E, E) | 0.04 | −0.42 | 0.43 |
| | | bilirubin_(E, Z_or_Z, E) | 0.10 | −0.23 | 0.01 |
| | | biliverdin | 0.01 | −0.44 | 0.23 |

TABLE 17

Plasma metabolites (hypothesized at the beginning of the study) and their ratios (median) between ASD samples at baseline, week 3, and week 10 compared with TD samples at baseline. p values are written in bold when they are less than 0.05 by one-tailed Wilcoxon signed-rank test before correcting for multiple hypotheses. To obtain the ratios, each metabolite was normalized such that the median value was one in the TD group at baseline.

| SUPER PATHWAY | SUB PATHWAY | BIOCHEMICAL | Median Ratio (ASD/TDbaseline) Baseline | Week 3 | Week 10 | p value Baseline vs. Week 3 | Week 10 |
|---|---|---|---|---|---|---|---|
| Amino Acid | Glutamate Metabolism | glutamate | 1.12 | 1.03 | 1.06 | 0.13 | 0.03 |
| | | glutathione,_oxidized_(GSSG)* | 1.33 | 1.12 | 1.33 | 0.10 | 0.01 |
| | Phenylalanine and Tyrosine Metabolism | 4-ethylphenyl_sulfate | 0.42 | 0.37 | 0.21 | 0.46 | 0.10 |
| | | dopamine_sulfate_(2) | 0.91 | 1.48 | 1.30 | 0.10 | 0.14 |
| | | p-cresol_sulfate | 0.95 | 0.86 | 1.05 | 0.47 | 0.37 |
| | | tyramine_O-sulfate | 0.34 | 0.34 | 0.34 | 0.09 | 0.08 |
| | Tryptophan Metabolism | indolepropionate | 0.57 | 1.39 | 0.97 | <0.01 | 0.01 |
| | | serotonin** | 1.09 | 1.00 | 1.06 | 0.21 | 0.04 |
| Cofactors and Vitamins | Hemoglobin and Porphyrin Metabolism | bilirubin | 0.76 | 0.81 | 0.77 | 0.20 | 0.17 |
| | | bilirubin_(E,E) | 0.59 | 0.63 | 0.58 | 0.37 | 0.12 |
| | | bilirubin_(E,Z_or_Z,E) | 0.85 | 0.84 | 0.90 | 0.43 | 0.17 |
| | | biliverdin | 0.61 | 0.73 | 0.70 | 0.39 | 0.36 |

*Average oxidized glutathione (GSSG) ratios between ASD and TD samples (ASD/TDbaseline) were 1.12 at baseline, 1.35 at week 3, and 1.53 at week 10.

**Average serotonin ratios between ASD and TD samples (ASD/TDbaseline) were 1.05 at baseline, 1.10 at week 3, and 1.18 at week 10.

In addition to the hypothesis-driven metabolites presented in Tables 1 and 2, search was performed for potentially important metabolites not previously recognized by evaluating all 619 metabolites and correcting for multiple hypotheses. Employed were two separate multiple hypotheses correction tests (Benjamini-Hochberg and Leave-One-Out methods) which yielded similar results. Out of 619 metabolites, 10 plasma metabolites were significantly different at baseline between the ASD and TD groups by both correction tests (Table 18, adjusted p<0.05). Nicotinamide riboside and inosine 5'-monophosphate (IMP) were the two most significantly different metabolites at baseline based on both Benjamini-Hochberg and Leave-One-Out correction, and both were significantly lower in the ASD group compared to the TD group. Two medium chain fatty acids, caprylate (with 8 carbon atoms, C8) and heptanoate (C7), were significantly higher in ASD samples, whereas amino acid products (sarcosine and methylsuccinate), dipeptides (valylglycine and leucylglycine), galactonate, and iminodiacetate were significantly lower in ASD samples (Table 18, adjusted p<0.05).

Table 19 shows how the metabolites listed in Table 3 changed after treatment. Sarcosine, methylsuccinate, nicotinamide riboside, IMP, valylglycine, and iminodiacetate were significantly lower in ASD samples at baseline and increased significantly after vancomycin at week 3 and remained increased after MTT at week 10 compared to baseline (Table 19, one-tailed Wilcoxon rank-test p<0.05; Clusters 3 and 4 in FIG. 1b). In contrast, caprylate and heptanoate were significantly higher in ASD samples at baseline, and significantly decreased after MTT at week 10 (p=0.03; Cluster 1 in FIG. 1b). Only two metabolites (galactonate and leucylglycine) in Table 19 did not change significantly. Galactonate was significantly low in the ASD group at baseline, and increased substantially after MTT, but the increase was not statistically significant (median ratio of ASD/TD of 0.05 at baseline, and 0.64 and 0.68 at week 3 and week 10 of MTT). Leucylglycine was significantly low in the ASD group at baseline, increased somewhat at week 3, but returned to its original level at week 10 (median ratio of ASD/TD of 0.24 at baseline, and 0.76 and 0.22 at week 3 and week 10). Overall, 8 of 10 abnormal metabolites shifted significantly after MTT so that they became closer to the levels in the TD group, and the other two partially shifted.

TABLE 18

Normalized Plasma metabolites that were significantly different at baseline after correcting for multiple hypotheses (adjusted p <0.05). Note that all p values presented here are smaller than 0.05 by two-tailed Mann-Whitney U test after correcting for multiple hypotheses.

| SUPER PATHWAY | SUB PATHWAY | BIOCHEMICAL | BH* | Leave-one-out | Median ASD | TD |
|---|---|---|---|---|---|---|
| Amino Acid | Glycine, Serine and Threonine Metabolism | sarcosine | 0.04 | 0.02 | −1.70 | 0.62 |
| | Leucine, Isoleucine and Valine Metabolism | methylsuccinate | 0.02 | 0.01 | −1.16 | 0.09 |
| Carbohydrate | Fructose, Mannose and Galactose Metabolism | galactonate | 0.03 | 0.01 | −0.90 | 0.46 |
| Cofactors and Vitamins | Nicotinate and Nicotinamide Metabolism | nicotinamide riboside | 0.02 | <0.01 | −1.03 | 0.65 |
| Lipid | Medium Chain Fatty Acid | caprylate_(8:0) | 0.04 | 0.05 | 1.13 | −0.54 |
| | | heptanoate_(7:0) | 0.05 | 0.03 | 1.66 | −0.54 |
| Nucleotide | Purine Metabolism, (Hypo)Xanthine/Inosine containing | inosine_5'-monophosphate_(IMP) | 0.02 | <0.01 | −1.00 | 0.36 |
| Peptide | Dipeptide | valylglycine | 0.04 | 0.05 | −0.70 | 0.31 |
| | | leucylglycine | 0.04 | 0.02 | −1.01 | 0.38 |
| Xenobiotics | Chemical | iminodiacetate_(IDA) | 0.03 | 0.01 | −1.54 | 0.51 |

*BH: Benjamini and Hochberg (a multiple hypothesis correction test)

TABLE 19

Ratios of normalized ASD Plasma metabolites to TD samples at baseline that were significantly different when comparing baseline to week 3, and week 10. p values are written in bold when they are less than 0.05 by one-tailed Wilcoxon signed-rank test after correcting for multiple hypotheses. To obtain the ratios, each metabolite was normalized such that the median value was one in the TD group at baseline.

| SUPER PATHWAY | SUB PATHWAY | BIOCHEMICAL | Median Ratio (ASD/TDbaseline) | | | Adjusted p value Baseline vs. | |
|---|---|---|---|---|---|---|---|
| | | | Baseline | Week 3 | Week 10 | Week 3 | Week 10 |
| Amino Acid | Glycine, Serine and Threonine Metabolism | sarcosine | 0.15 | 1.00 | 0.97 | 0.04 | 0.03 |
| | Leucine, Isoleucine and Valine Metabolism | methylsuccinate | 0.58 | 1.07 | 1.23 | 0.03 | <0.01 |
| Carbohydrate | Fructose, Mannose and Galactose Metabolism | galactonate | 0.05 | 0.68 | 0.64 | 0.12 | 0.25 |
| Cofactors and Vitamins | Nicotinate and Nicotinamide Metabolism | nicotinamide_riboside | 0.42 | 0.89 | 0.95 | 0.03 | 0.03 |
| Lipid | Medium Chain Fatty Acid | caprylate_(8:0) | 2.91 | 1.28 | 0.90 | 0.10 | 0.03 |
| | | heptanoate_(7:0) | 6.67 | 1.15 | 0.94 | 0.13 | 0.03 |
| Nucleotide | Purine Metabolism, (Hypo)Xanthine/Inosine | inosine_5'-monophosphate_(IMP) | 0.41 | 0.89 | 1.02 | <0.01 | <0.01 |
| Peptide | Dipeptide | valylglycine | 0.22 | 0.77 | 0.74 | 0.03 | 0.03 |
| | | leucylglycine | 0.24 | 0.76 | 0.22 | 0.06 | 0.09 |
| Xenobiotics | Chemical | iminodiacetate_(IDA) | 0.54 | 0.98 | 0.98 | 0.03 | 0.04 |

Figure 15C:
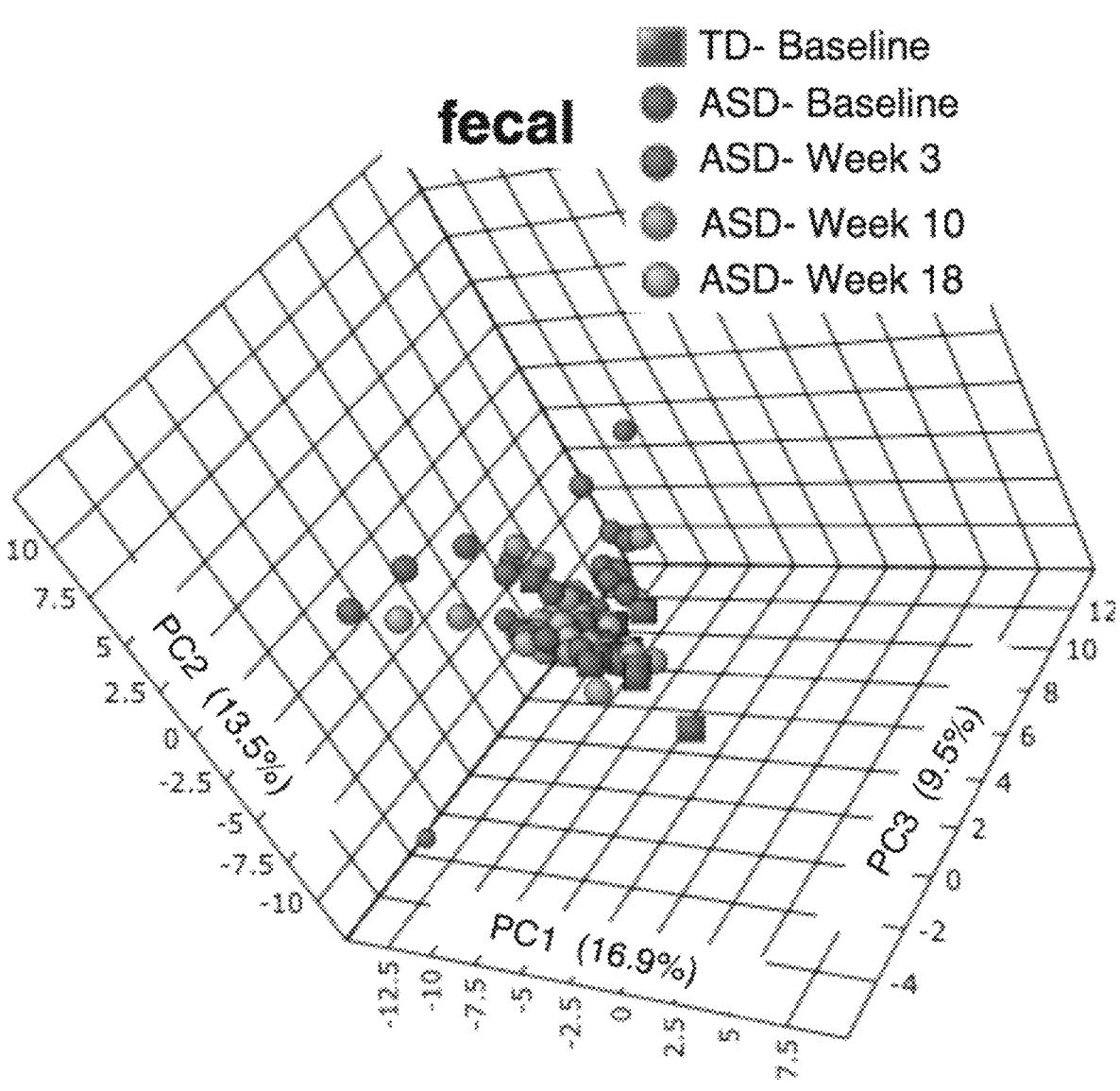
FIG. 15C. Principal component analysis (PCA) with fecal samples at different time points.
Figure 15D:
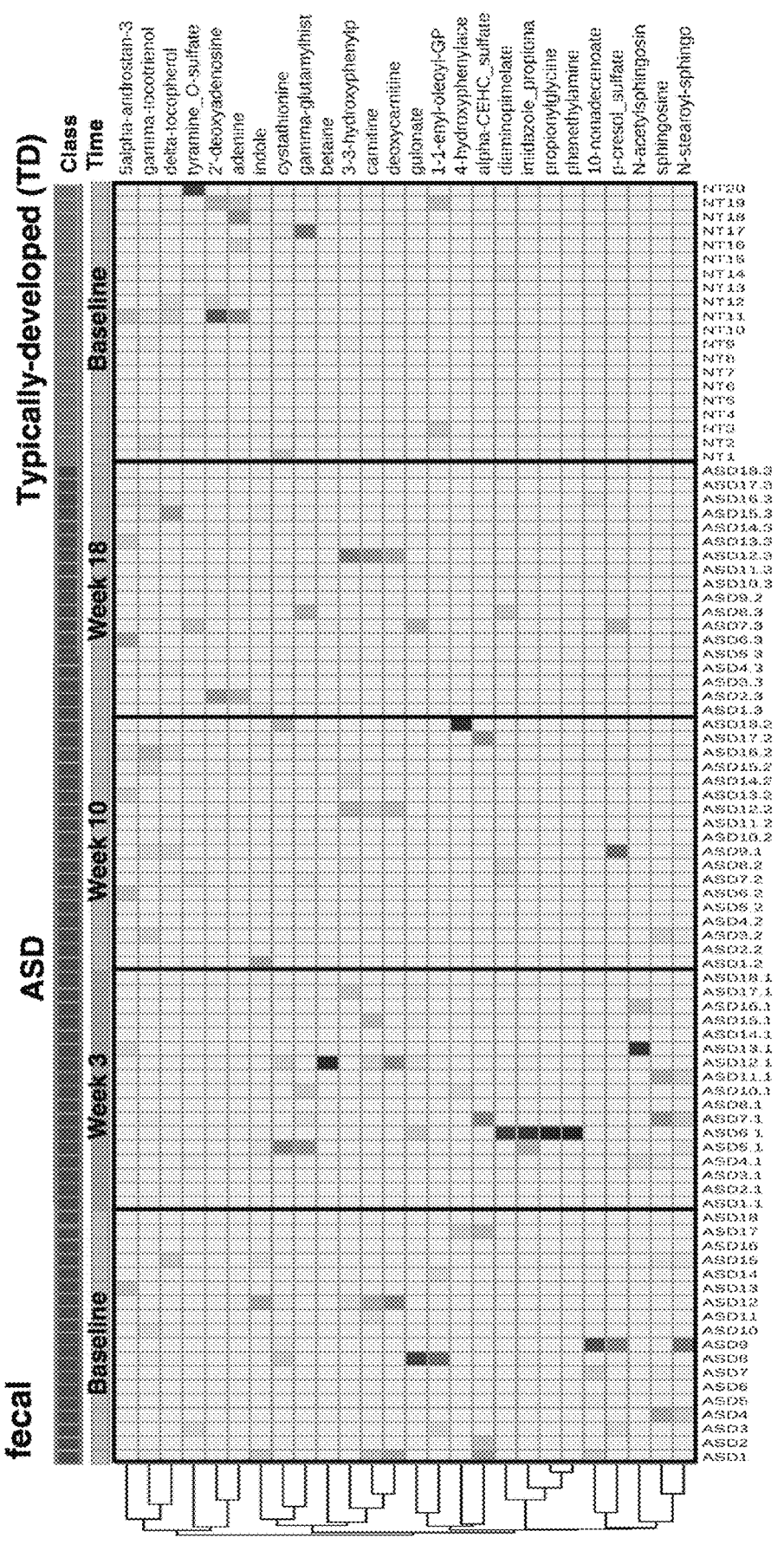
FIG. 15D. Heatmap profile with dendrogram with fecal samples at different time points.

Fecal Metabolites: Tyrosine/Tryptophan Derivatives were Significantly Different at Baseline In fecal samples, 669 metabolites in total were identified. In order to evaluate differences in metabolite profiles as a group, first performed was PCA and heatmap analysis for the 26 metabolites whose levels were most different at baseline between two groups (un-adjusted p<0.05). As shown in FIG. 15C, PCA results showed that the fecal metabolites of the ASD and TD groups were similar at baseline, and remained similar after MTT. FIG. 15D shows that there were no significant differences between ASD and TD groups at baseline, and no significant change was observed between baseline and after MTT.

Individual levels of fecal metabolites were also investigated. Among these metabolites including neurotransmitters, tyrosine/tryptophan derivatives, and antioxidants, three tyrosine derivatives (p-cresol sulfate, tyramine O-sulfate, and 4-hydrophenylacetate) were significantly different at baseline (un-adjusted p<0.05, Table 20). p-cresol sulfate and 4-hydrophenylacetate levels were significantly higher in feces of the ASD group at baseline, whereas tyramine 0-sulfate, a metabolite that has similar chemical structure to 4-EPS and p-cresol sulfate, was significantly lower in feces of the ASD group. Indole, a serotonin precursor, was significantly higher at baseline in the ASD samples (Table 20). Three fecal metabolites changed after MTT. For the "hypotheses-based" metabolites listed above (Table 20), three metabolites changed significantly after MTT. P-cresol sulfate levels were significantly higher in ASD samples at baseline and were reduced to levels similar to the TD group after MTT (Tables 5 and 6, 1-tailed Wilcoxon rank test p=0.05). Dopamine and biliverdin in fecal samples significantly changed after MTT compared with their levels at baseline (Table 6, Wilcoxon signed-rank test p<0.05). For dopamine levels in individual ASD subjects, 7 out of 18 ASD samples were high at baseline, but they subsequently decreased and became similar to the TD group by week 18. Biliverdin levels were non-significantly increased in the ASD group at baseline, and at week 18 had significantly decreased and were closer to the TD group (Table 21, 1-tailed Wilcoxon rank test p=0.05). The other two tyrosine derivatives—tyramine O-sulfate and 4-hydrophenylacetate—were not significantly changed after MTT. In summary, 3 hypotheses-based fecal metabolites (p-cresol sulfate, dopamine, and biliverdin) significantly changed and became closer to the levels of the TD group.

TABLE 20

Normalized fecal metabolites (hypothesized at the beginning of the study) and their median values of ASD and TD samples at baseline. p values are written in bold when they are less than 0.05 by two-tailed Mann-Whitney U test before correcting for multiple hypotheses.

| SUPER PATHWAY | SUB PATHWAY | BIOCHEMICAL | un-adj. P value | Median | |
|---|---|---|---|---|---|
| | | | | ASD | TD |
| Amino Acid | Glutamate Metabolism | gamma-aminobutyrate_GABA | 0.47 | −0.21 | −0.19 |
| | | glutamate | 0.92 | −0.33 | −0.19 |
| | Phenylalanine and Tyrosine Metabolism | 4-hydroxyphenylacetate | 0.04 | −0.15 | −0.22 |
| | | dopamine | 0.57 | −0.60 | −0.60 |
| | | p-cresol | 0.33 | −0.11 | −0.23 |
| | | p-cresol_sulfate | 0.03 | −0.10 | −0.42 |
| | | tyramine_O-sulfate | 0.03 | −0.45 | −0.17 |

TABLE 20-continued

Normalized fecal metabolites (hypothesized at the beginning of the study)
and their median values of ASD and TD samples at baseline. p values are written in
bold when they are less than 0.05 by two-tailed Mann-Whitney U test before
correcting for multiple hypotheses.

| SUPER PATHWAY | SUB PATHWAY | BIOCHEMICAL | un-adj. P value | Median ASD | Median TD |
|---|---|---|---|---|---|
| | Tryptophan Metabolism | indole | 0.01 | 0.18 | −0.70 |
| | | serotonin | 0.33 | −0.21 | 0.05 |
| | Cofactors and Vitamins | bilirubin | 0.56 | −0.33 | −0.36 |
| | Hemoglobin and Porphyrin | bilirubin_E, E)* | 0.35 | −0.35 | −0.35 |
| | Metabolism | biliverdin | 0.09 | −0.24 | −0.50 |

TABLE 21

Fecal metabolites (with hypothesis) and their ratios (median) between ASD samples at baseline, week 3, week 10, and week
18 compared with TD samples at baseline. p values are written in bold when they are less than 0.05 by one-tailed Wilcoxon
signed-rank test before correcting for multiple hypotheses. To obtain the ratios, each metabolite was normalized such that
the median value was one in the TD group at baseline.

| SUPER PATHWAY | SUB PATHWAY | BIOCHEMICAL | Median Ratio (ASD/TD$_{baseline}$) Baseline | Week 3 | Week 10 | Week 18 | p value Baseline vs. Week 3 | Week 10 | Week 18 |
|---|---|---|---|---|---|---|---|---|---|
| Amino Acid | Glutamate Metabolism | Gamma-aminobutyrate_(GABA) | 0.81 | 0.72 | 0.51 | 0.74 | 0.28 | 0.11 | 0.12 |
| | | glutamate | 0.93 | 1.00 | 1.03 | 1.16 | 0.23 | 0.42 | 0.31 |
| | Phenylalanine and Tyrosine Metabolism | 4-hydroxyphenyl-acetate | 1.59 | 1.03 | 0.98 | 0.99 | 0.07 | 0.32 | 0.12 |
| | | dopamine* | 1.00 | 4.51 | 2.97 | 1.00 | 0.28 | 0.46 | 0.02 |
| | | p-cresol | 1.14 | 0.65 | 0.74 | 1.38 | 0.06 | 0.05 | 0.32 |
| | | p-cresol_sulfate | 3.14 | 1.69 | 1.88 | 1.05 | 0.11 | 0.16 | 0.05 |
| | | tyramine_O-sulfate | 0.18 | 0.10 | 0.25 | 0.17 | 0.32 | 0.38 | 0.48 |
| | Tryptophan Metabolism | indole | 3.50 | 2.45 | 2.89 | 2.90 | 0.19 | 0.46 | 0.12 |
| | | serotonin | 0.63 | 0.51 | 0.66 | 0.56 | 0.43 | 0.49 | 0.15 |
| Cofactors and Vitamins | | bilirubin | 1.42 | 4.67 | 1.00 | 0.66 | 0.12 | 0.44 | 0.12 |
| Hemoglobin and Porphyrin | | Bilirubin_(E,E)* | 1.00 | 1.00 | 1.00 | 1.00 | 0.11 | 0.37 | 0.17 |
| Metabolism | | biliverdin | 1.69 | 1.52 | 1.54 | 1.27 | 0.47 | 0.25 | 0.04 |

*Average dopamine ratios between ASD and TD samples (ASD/TD$_{baseline}$) were 4.58 at baseline, 6.63 at week 3, 4.54 at week 10, and 2.38 at week 18.

PICRUST/HUMAnN Analyses Predicted Microbial Functions but not Significance

With 16S rRNA gene amplicon sequencing data, PICRUSt and HUMAnN analyses predicted 116 microbial function modules in total throughout the samples. However, none of the functional modules identified showed statistical significance after correcting for multiple hypotheses testing.

Figure 16A:
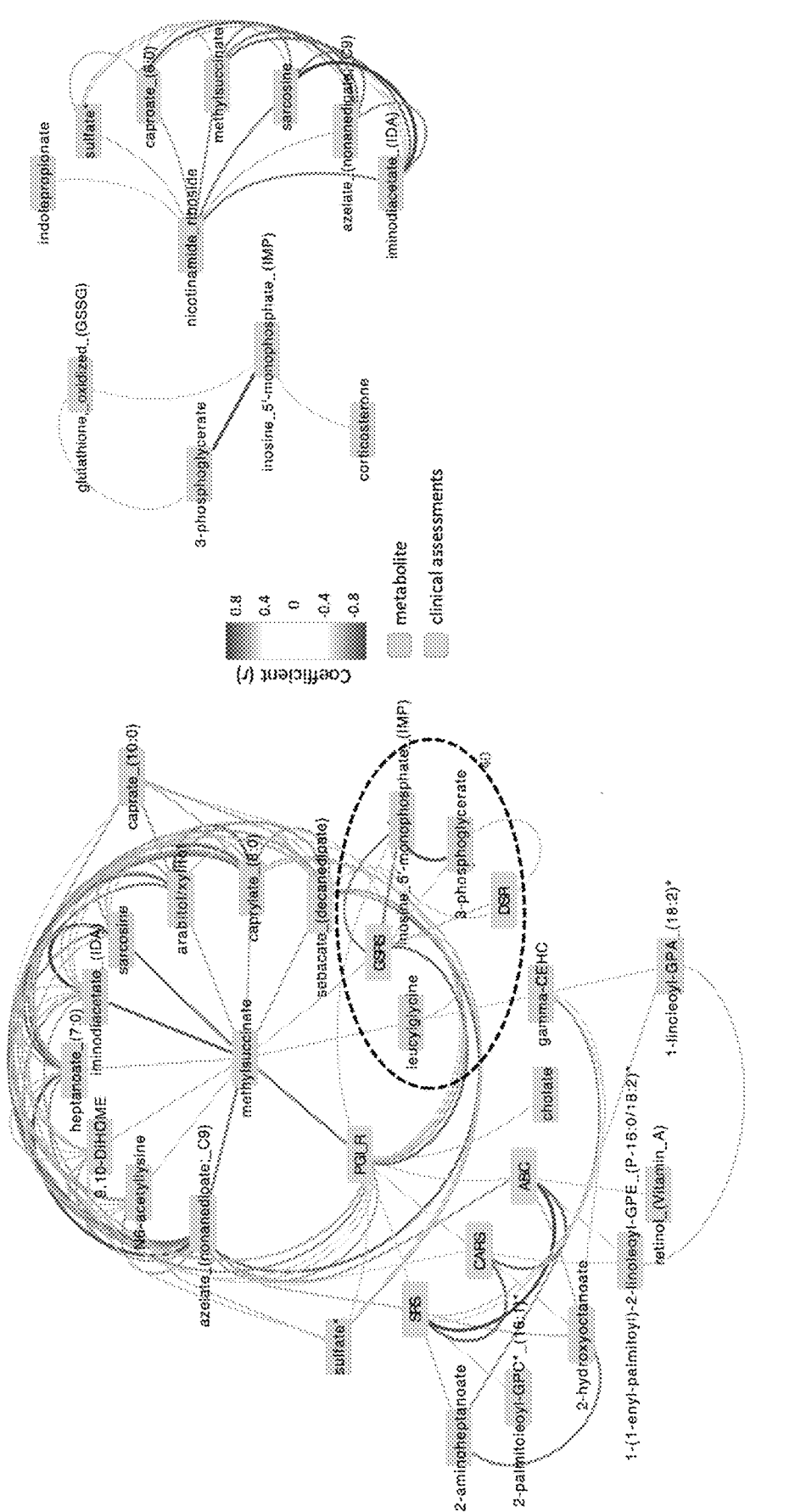
FIG. 16A. Co-occurrence network analysis with plasma metabolites associated with clinical assessment scores (highlighted in green). Blue and red lines between metabolites indicate positive and negative correlations, respectively.

Co-Occurrence Networks Showed Links Between Metabolites/Microbes/Clinical Assessments FIG. 16A displays the plasma metabolites that had the most significant correlations (Spearman correlation coefficient $|r|>0.5$) with clinical assessments of GI and ASD-related symptoms. IMP levels were strongly negatively correlated with both GI assessments—GSRS and DSR (a black-dotted circle in FIG. 2a,c); in other words, the increase of IMP levels to normal levels after MTT was strongly associated with improvements in GI symptoms. Methylsuccinate was strongly correlated with PGI-R (Spearman correlation, $|r|=0.75$, FIG. 2a,d), i.e, the increase of methylsuccinate to normal levels after MTT was strongly associated with improvements in ASD-related symptoms. There were also many other weaker correlations of metabolites with clinical assessments. Iminodiacetate was positively correlated with the PGI-R (r=0.61), but caprylate and heptanoate were both negatively correlated with the PGI-R (r=−0.58 and −0.66). For plasma metabolites and the three gut bacteria (*Bifidobacterium, Prevotella*, and *Desulfovibrio*), only one significant correlation was found, between *Bifidobacterium* and 5-(galactosylhydroxy)-L-lysine (r=0.54, p<0.01).

Figure 17A:
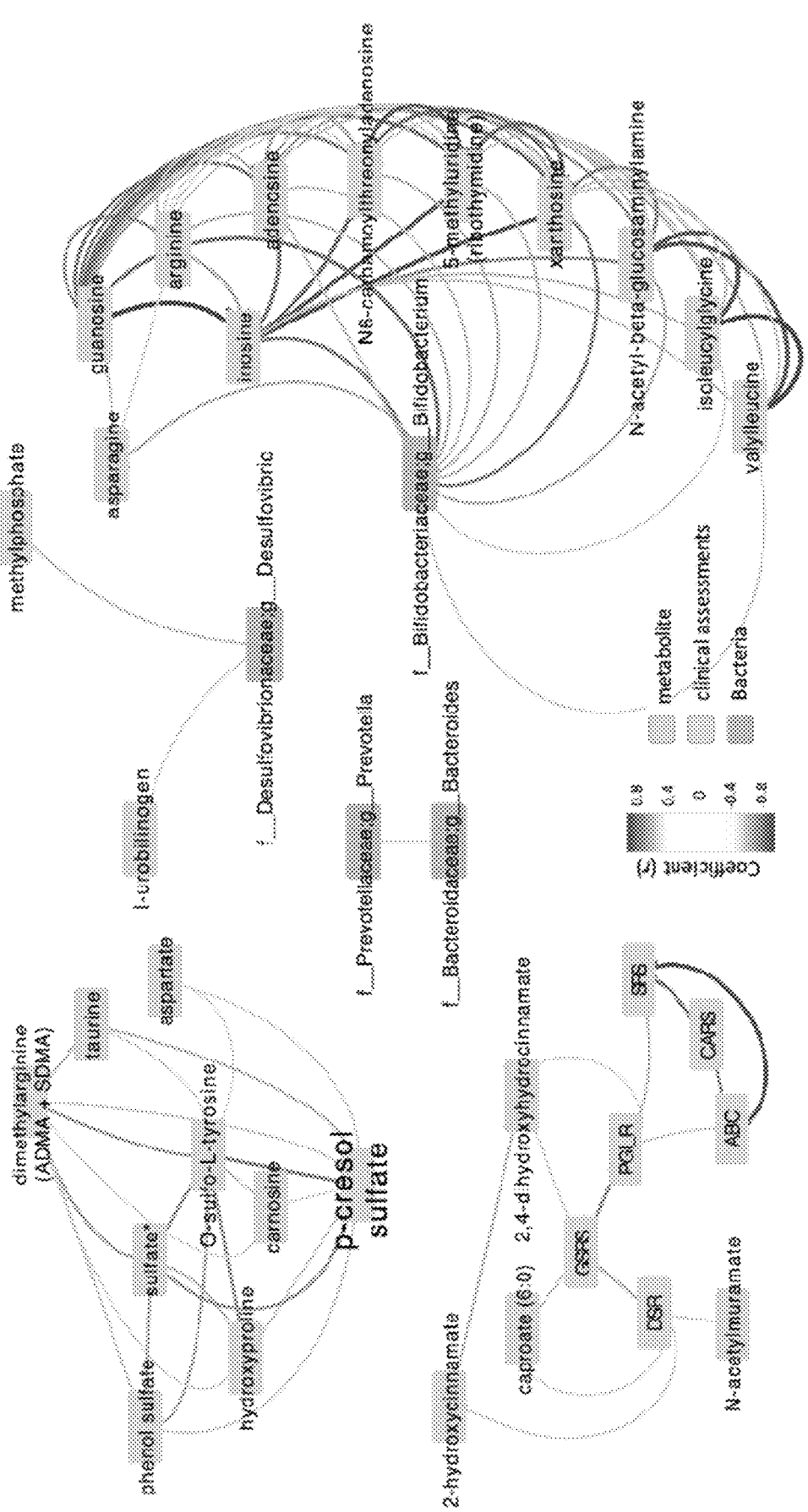
FIG. 17A. Co-occurrence network analysis between fecal metabolites, clinical measurement, and bacterial components in stool. Co-occurrence network associated with p-cresol sulfate, clinical measurements, and key significant bacteria of *Bifidobacterium*, *Prevotella*, and *Desulfovibrio*.
Figure 17B:
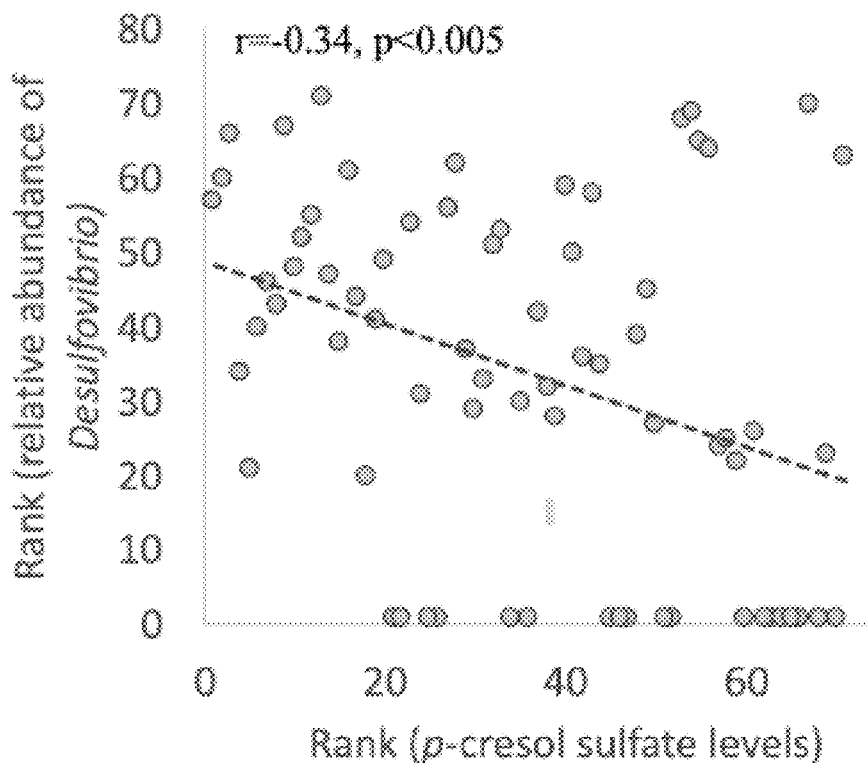
FIG. 17B. Correlation between Sulfate reducing *Desulfovibrio* and p-cresol sulfate (Spearman correlation, p<0.005).

FIG. 17A shows a co-occurrence network analysis between fecal metabolites, clinical measurements, and three bacteria (*Bifidobacterium, Prevotella*, and *Desulfovibrio*), which were the three gut microbes which significantly changed in response to MTT. Co-occurrence network analysis shows that *Bifidobacterium* is strongly correlated with many stool metabolites, especially negatively correlated with amino acids/peptides (arginine, asparagine, isoleucylglycine, and valylleucine) and nucleotides (adenosine, xanthosine, and inosine) (FIG. 17A). In contrast, sulfate reducing *Desulfovibrio* was not strongly correlated with metabolites of interests, but there was a modest significant negative correlation with p-cresol sulfate (r=−0.34, p<0.005) and sulfate (r=−0.40, p<0.001), FIG. 17B, C). p-cresol sulfate and sulfate levels were strongly and significantly correlated with each other (p<0.001 and r=0.67, FIG. 3d). GI and behavioral symptoms were associated with several metabolites, but those metabolites were not correlated with any of the three bacteria, suggesting that other bacteria (or subsets of those bacteria) are affecting the metabolites associated with GI and ASD symptoms.

Participants in the MTT trial experienced major changes in their gut microbiome. MTT involved using vancomycin (an antibiotic), a stomach acid suppressant, and a bowel cleanse to reduce the initial microbiome, and adding new microbiota from very healthy donors by fecal microbiota transplant daily for 7-8 weeks. This study demonstrates that MTT resulted in major changes in plasma metabolite profiles, and modest changes in fecal profiles (summarized in FIG. 18). One reason may be due to small sample size and greater statistical noise in fecal samples. Another possible hypothesis for the major change in plasma but not fecal metabolites is that perhaps MTT improved epithelial cell integrity and reduced intestinal permeability, resulting in less diffusion of fecal metabolites into the bloodstream and thus a more normal set of plasma metabolites. The other hypothesis is that by modifying the microbiota in the gut, important host interactions that rely on microbial metabolites were also modified leading to the overproduction or consumption of systemic metabolites.

Plasma Metabolites

For plasma metabolites, PCA found that overall the ASD group was initially very different from the TD group (primarily due to PC1), but after vancomycin (week 3) the two groups were more similar, and after 10 weeks of MTT, there was little difference between the ASD and TD groups (FIG. 1a). The heatmap analysis (FIG. 15B) shows that many individual metabolites that were initially higher (cluster 1, n=23) or lower (clusters 3 and 4, n=25) in ASD shifted towards more normal levels after MTT; however, some metabolites with abnormal levels at baseline did not improve (clusters 2 and 5, n=25). These individual shifts contributed to an overall change in plasma metabolites as shown in the PCA (summarized in FIG. 15A). As hypothesized, some neurotransmitters that were significantly different between the ASD and TD groups at baseline significantly improved after MTT. Glutamate levels were significantly higher in ASD plasma samples at baseline and were significantly reduced at the end of the treatment in week 10 (Table 16 and 17). This observation is consistent with what was hypothesized, because glutamate is a major excitatory neurotransmitter that has been related to anxiety and excitation, which are behavioral symptoms that children with ASD experience. Serotonin levels in plasma samples were not different between ASD and TD groups at baseline but significantly increased at week 10 (Table 16 and 17). High level of serotonin in blood (hyperserotonemica), however, has been suspected as one of ASD phenotypehas previously been reported in a subset of people with ASD and may contribute to their symptoms. Thus, changes in the concentrations of these metabolites could have contributed to improvements. Bilirubin and its oxidized form biliverdin possess antioxidant properties, and their relative abundances were significantly low in plasma of autistic samples at baseline (Table 16), reflecting a deficit on preventing oxidative stress in children with ASD. MTT, however, did not change bilirubin and biliverdin levels in plasma (Table 17), so these may be a useful target for other future therapies.

After correcting for multiple hypotheses, 10 additional plasma metabolites were found that were significantly different in ASD vs. controls at baseline (Table 18). Sarcosine and nicotinamide riboside were significantly lower in ASD samples, and their levels significantly increased after MTT (Table 18 and 19). Sarcosine, also called N-methylglycine, is converted to glycine that has a vital role in a wide range of human physiology including nucleic acid synthesis and central nervous system homeostasis. Sarcosine supplementation is beneficial for depression and schizophrenia. Nicotinamide riboside is a pyridine-nucleoside form of vitamin B3 and a precursor for nicotinamide adenine dinucleotide (NAD+), a critical molecule involved in hundreds of redox and other reactions. Typically, tryptophan or aspartate are converted to NAD, but an alternative path involves synthesis of NAD from nicotinamide riboside (Salvage pathways) when the normal pathway is blocked. NAD levels were found to be significantly lower in children with ASD in another study and found to increase significantly after treatment with a vitamin/mineral supplement or by supplementation with NADH or ribose. Nicotinamide riboside supplementation prevented neurological damage and improved cognitive and physical function in an Alzheimer's disease model.

Figure 16B:
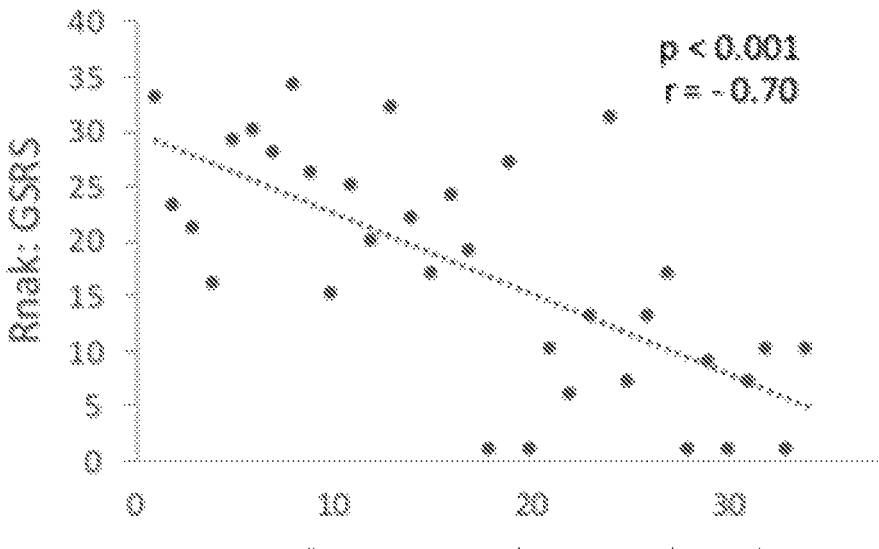
FIG. 16B. Rank-based plot to show strong correlations between GSRS and inosine 5'-monophosphate. p and r values are for rank-based spearman correlation tests.
Figure 16C:
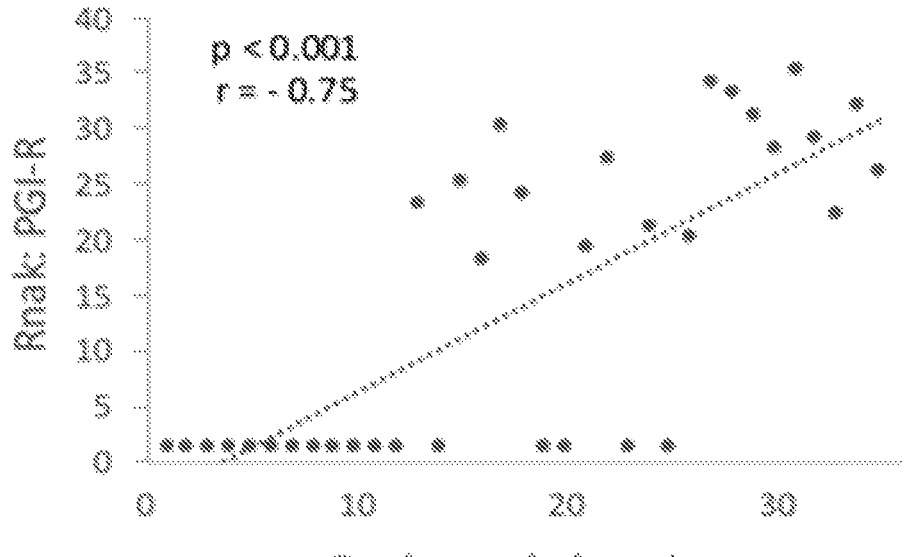
FIG. 16C. Rank-based plot to show strong correlations between PGI-R and methylsuccinate. p and r values are for rank-based spearman correlation tests.

Intriguingly, nicotinamide riboside in plasma samples is positively correlated with tryptophan derivatives, indolepropionate (or indole-3-propionate) and methylsuccinate (FIG. 16B). Indolepropionate helps maintain mucosal homeostasis and is a neuroprotective antioxidant, which is consistent with our findings of low levels in the ASD group before MTT, but normal levels after MTT. Methylsuccinate is a competitive inhibitor of succinate dehydrogenase that is involved in GABA shunt and reactive oxygen stress (ROS) homeostasis. Methylsuccinate was strongly positively correlated with PGI-R and negatively correlated with GSRS (r=−0.51), consistent with improvements in ASD and GI symptoms after MTT. Methylsuccinate was positively correlated with sarcosine (r=0.76) and leucylglycine (r=0.53), and negatively correlated with heptanoate (r=−0.53) and caprylate (r=−0.57). Iminodiacetate was also positively correlated with sarcosine (r=0.93) and methylsuccinate (r=0.81)

Inosine 5'-monophosphate (IMP) was significantly lower in the ASD group at baseline and increased after MTT; that increase was strongly correlated with improvements in GI symptoms (GSRS and DSR) (FIG. 2c). IMP is involved in nicotinamide adenine dinucleotide (NAD+)-dependent oxidation that converts IMP and NAD+ to xanthosine monohphosphate and NADH (inosine-5'-monophosphate dehydrogenase). Inosine-5'-monophosphate dehydrogenase activity was suggested to be related to irritable bowel disease. IMP was significantly and positively correlated with 3-phosphoglycerate (3PG) and oxidized glutathione (FIG. 16B). No meaningful metabolic relation was found between these three metabolites, but 3PG is linked to energy generation in mitochondria and folate metabolism. Glutathione is an antioxidant which can neutralize ROS and has many important roles in the body including detoxification and immune function. In a previous study, reduced glutathione (GSH) levels were lower in plasma samples of children with ASD, and a redox ratio of reduced to oxidized glutathione (GSH: GSSG) was lower compared with typically-developing children. In our plasma samples, oxidized glutathione (GSSG) levels was comparable between groups at baseline and significantly increased after MTT (Table 17). Since reduced glutathione was not measured in our analysis, the redox ratio of glutathione was not available to compare with the previous study.

Caprylate and heptanoate are medium-chain fatty acids (MCFAs) that were highly correlated with one another (r=0.79), and both were also negatively correlated with sarcosine (r=−0.58). Methylsuccinate were negatively correlated with caprylate (r=−0.57) and heptanoate (r=−0.53), and iminodiacetate were also negatively correlated with caprylate (r=−0.55) and heptanoate (r=−0.51). The ASD group had average levels of caprylate and heptanoate at baseline that were 190% and 590% above normal, respectively, and decreased to normal levels after MTT. They were both significantly correlated with the PGI-R (r=−0.58 and −0.66), so that their decrease after MTT was correlated with an improvement in ASD symptoms. Galactonate is formed by oxidation of galactose, possibly by galactose dehydrogenase. At baseline, the level of galactonate was significantly lower in ASD group, suggesting impaired production. Another study, however, found galactonate was higher in children with ASD.

Fecal Metabolites

Several of the metabolites that were hypothesized to be abnormal were in fact significantly different in ASD vs. controls (without controlling for multiple hypotheses testing), including higher levels of p-cresol sulfate, 4-hydroxyphenylacetate, and indole, and lower levels of tyramine O-sulfate (Table 20 and 21). p-cresol sulfate decreased significantly toward normal levels after MTT (see Table 21), which is in line with what was expected, but 4-hydroxyphenylacetate, tyramine O-sulfate, and indole did not significantly change.

Figure 17C:
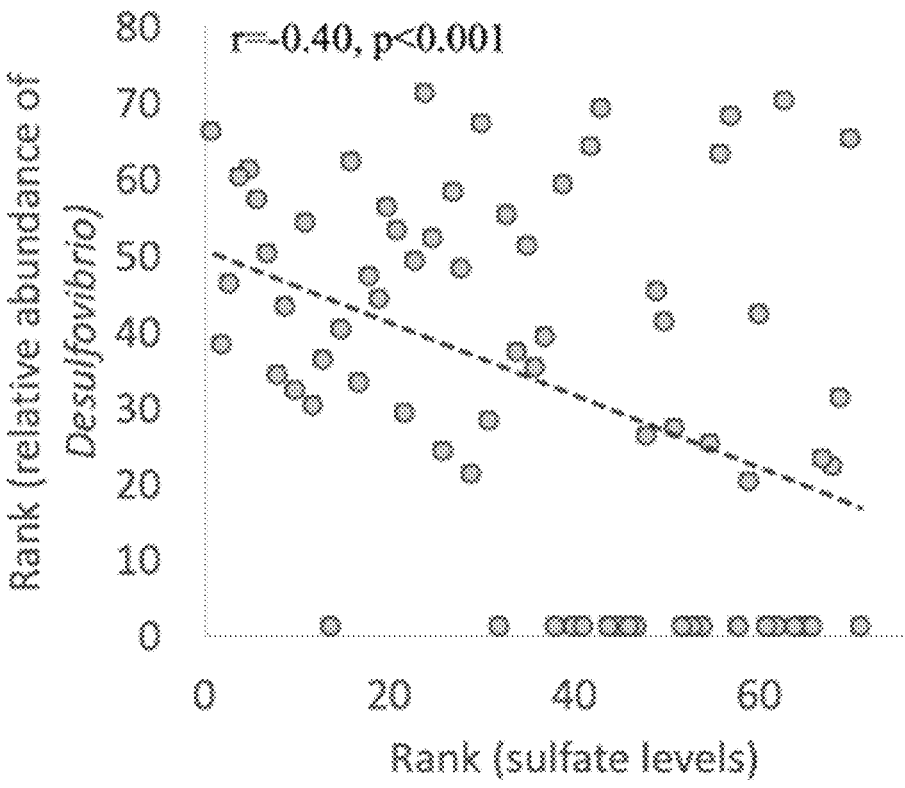
Figure 17D:
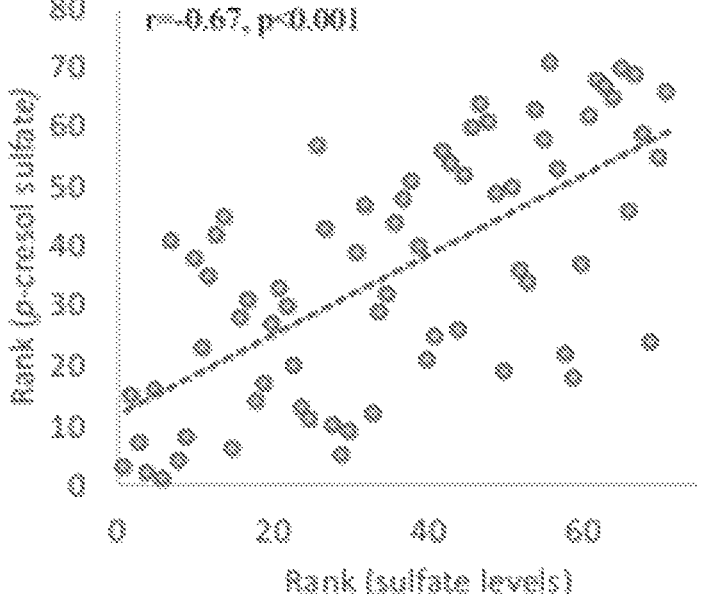

Elevated p-cresol sulfate induces oxidative stress, and tyrosine metabolism along with p-cresol has been implicated in the etiology of ASD through human and animal studies. A previous study with an autism mouse model claimed p-ethylphenyl sulfate (4-EPS) as an important metabolite associated with autism symptoms and pointed out its similar chemical structure to p-cresol sulfate, a uremic toxin, and Axial Biotherapeutics has reported elevated concentrations of 4-EPS in children with ASD. In this study, higher but not statistically significant p-cresol levels were observed in ASD fecal samples (Table 20). Notably, the decrease in p-cresol sulfate after MTT was modestly but significantly associated with the increase in *Desulfovibrio* (FIG. 17B). *Desulfovibrio* has not been listed as a beneficial microbe but rather been accepted as a detrimental one in the view of autism phenotype, but here it was significantly increased after MTT at week 10, suggesting it may have some beneficial role. Significant correlations between *Desulfovibrio*, p-cresol sulfate, and sulfate (FIG. 17B-D) support a potential role for sulfate reducing microbes like *Desulfovibrio* in the metabolism of p-cresol sulfate. Regarding 4-EPS, it was only identified in plasma samples and its levels was marginally lower in ASD samples (two-tailed Mann-Whitney U test p=0.09). This observation is not consistent with Hsiao et al. data on mice, and we did not see any change after MTT. A larger study is needed to clarify if 4-EPS is relevant to human ASD.

Overall, it is intriguing that this study showed significant changes in metabolic features in plasma metabolites but not much in fecal metabolites even though substantial changes in gut microbiota were found after MTT. This distinct result between plasma and fecal samples reflects some of the challenges of working with complex gut microbiota and their metabolites. This study relied on a small sample size with different GI disorder types (e.g., constipation, diarrhea, or abdominal pain), and a larger cohort may help differentiate subtle but important changes in fecal metabolites that could be masked in this study. Despite these shortcomings, observation on the significance in fecal p-cresol sulfate as well as global changes in plasma samples indicate how strong and effective MTT was in this trial of ASD.

Overall, MTT drove global changes in plasma metabolite profiles in children with ASD. Vancomycin seems to initiate a shift in the plasma metabolite profiles, but microbiota transfer resulted in further shifts and seemed to stabilize the effect of vancomycin. As a result, the overall plasma metabolite profiles in the ASD group were modulated from being distinctly different from the TD group to becoming very similar to the TD group. Among plasma metabolites that were significantly different in ASD at baseline, glutamate and medium chain fatty acids (caprylate and heptanoate) were significantly higher at baseline compared with control and significantly decreased after MTT. Indoleproprionate, sarcosine, methylsuccinate, nicotinamide riboside, IMP, valylglycine, and iminodiacetate were significantly lower at baseline and increased after MTT. Other metabolites like leucylglycine, galactonate, bilirubin, and biliverdin were abnormal at baseline and did not improve after MTT, so those are potential targets for other future therapies. Overall, this data provides some insight into why microbiota transplant therapy appears to be able to significantly reduce GI and ASD symptoms. It also suggests a biochemical basis for some ASD symptoms.

In contrast, for fecal metabolites only a few metabolites were different at baseline, and none were significantly different after correction for multiple hypotheses testing. At baseline, p-cresol sulfate, 4-hydroxyphenylacetate, tyramine O-sulfate, and indole were initially different between groups (unadjusted p<0.05), and only p-cresol sulfate significantly changed after MTT. There were significant correlations between p-cresol sulfate, sulfate, and *Desulfovibrio*, suggesting a potential role of *Desulfovibrio* on the metabolism of p-cresol sulfate and possible autism etiology. Further studies of fecal and blood metabolites in ASD, both before and after MTT, are warranted, as well as clinical trials of other therapies to address the metabolic changes which MTT was not able to correct.

REFERENCES

1. Baio, J., et al., *Prevalence of autism spectrum disorder among children aged 8 Years—Autism and developmental disabilities monitoring network,* 11 *Sites, United States,* 2014. Mmwr Surveillance Summaries, 2018. 67(6): p. 1-23.
2. Xu, G. F., et al., *Prevalence and treatment patterns of autism spectrum disorder in the United States,* 2016. JAMA Pediatrics, 2019. 173(2): p. 153-159.
3. Johnson, C. P. and S. M. Myers, *Identification and evaluation of children with autism spectrum disorders.* Pediatrics, 2007. 120(5): p. 1183-1215.
4. Sharon, G., et al., *The Central Nervous System and the Gut Microbiome.* Cell, 2016. 167(4): p. 915-932.
5. McElhanon, B. O., et al., *Gastrointestinal symptoms in autism spectrum disorder: a meta-analysis.* Pediatrics, 2014. 133.
6. Vargason, T., D. L. McGuinness, and J. Hahn, *Gastrointestinal symptoms and oral antibiotic use in children with autism spectrum disorder: Retrospective analysis of a privately insured US population.* Journal of Autism and Developmental Disorders, 2019. 49(2): p. 647-659.
7. Adams, J. B., et al., *Gastrointestinal flora and gastrointestinal status in children with autism-comparisons to typical children and correlation with autism severity.* BMC Gastroenterol, 2011. 11.
8. Kang, D. W., et al., *Differences in fecal microbial metabolites and microbiota of children with autism spectrum disorders.* Anaerobe, 2017. 49: p. 121-131.
9. Wang, M. B., et al., *Alterations in gut glutamate metabolism associated with changes in gut microbiota composition in children with autism spectrum disorder.* Msystems, 2019. 4(1): p. 12.

10. Liu, F. T., et al., *Altered composition and function of intestinal microbiota in autism spectrum disorders: a systematic review*. Translational Psychiatry, 2019. 9: p. 13.

11. Finegold, S. M., et al., *Pyrosequencing study of fecal microflora of autistic and control children*. Anaerobe, 2010. 16.

12. Strati, F., et al., *New evidences on the altered gut microbiota in autism spectrum disorders*. Microbiome, 2017. 5: p. 11.

13. Tomova, A., et al., *Gastrointestinal microbiota in children with autism in Slovakia*. Physiology & Behavior, 2015. 138: p. 179-187.

14. Kang, D. W., et al., *Reduced incidence of Prevotella and other fermenters in intestinal microflora of autistic children*. PLoS One, 2013. 8(7): p. e68322.

15. Song, Y. L., CX. Liu, and S. A. Finegold, *Real-time PCR quantitation of Clostridia in feces of autistic children*. Applied and Environmental Microbiology, 2004. 70(11): p. 6459-6465.

16. Williams, B. L., et al., *Application of novel PCR-based methods for detection, quantification, and phylogenetic characterization of Sutterella species in intestinal biopsy samples from children with autism and gastrointestinal disturbances*. mBio, 2012. 3: e00261-11(1).

17. Krajmalnik-Brown, R., et al., *Gut bacteria in children with autism spectrum disorders: challenges and promise of studying how a complex community influences a complex disease*. Microb Ecol Health Dis, 2015. 26.

18. Finegold, S. M., *Desulfovibrio species are potentially important in regressive autism*. Med Hypotheses, 2011. 77.

19. Arumugam, M., et al., *Enterotypes of the human gut microbiome*. Nature, 2011. 473(7346): p. 174-180.

20. Krajmalnik-Brown, R., et al., *Effects of gut microbes on nutrient absorption and energy regulation*. Nutrition in Clinical Practice, 2012. 27(2): p. 201-214.

21. De Angelis, M., et al., *Fecal microbiota and metabolome of children with autism and pervasive developmental disorder not otherwise specified*. Plos One, 2013. 8(10): p. 18.

22. Wang, L., et al., *Elevated fecal short chain fatty acid and ammonia concentrations in children with autism spectrum disorder*. Digestive Diseases and Sciences, 2012. 57(8): p. 2096-2102.

23. Ming, X., et al., *Metabolic perturbance in autism spectrum disorders: A metabolomics study*. Journal of Proteome Research, 2012. 11(12): p. 5856-5862.

24. Yap, I. K. S., et al., *Urinary metabolic phenotyping differentiates children with autism from their unaffected siblings and age-matched controls*. Journal of Proteome Research, 2010. 9(6): p. 2996-3004.

25. Shinohe, A., et al., *Increased serum levels of glutamate in adult patients with autism*. Progress in Neuro-Psychopharmacology & Biological Psychiatry, 2006. 30(8): p. 1472-1477.

26. El-Ansary, A. and L. AI-Ayadhi, *GABAergic/glutamatergic imbalance relative to excessive neuroinflammation in autism spectrum disorders*. Journal of Neuroinflammation, 2014. 11.

27. Adams, J. B., et al., *Effect of a vitamin/mineral supplement on children and adults with autism*. BMC Pediatr, 2011. 11.

28. Gabriele, S., et al., *Urinary p-cresol is elevated in young French children with autism spectrum disorder a replication study*. Biomarkers, 2014. 19(6): p. 463-470.

29. Hsiao, E. Y., et al., *Microbiota modulate behavioral and physiological abnormalities associated with neurodevelopment disorders*. Cell, 2013. 155.

30. Sharon, G., et al., *Human Gut Microbiota from Autism Spectrum Disorder Promote Behavioral Symptoms in Mice*. Cell, 2019. 177(6): p. 1600-+.

31. Kang, D.-W., et al., *Microbiota Transfer Therapy alters gut ecosystem and improves gastrointestinal and autism symptoms: an open-label study*. Microbiome, 2017. 5(1): p. 10.

32. Kang, D. W., et al., *Long-term benefit of Microbiota Transfer Therapy on autism symptoms and gut microbiota*. Scientific Reports, 2019. 9: p. 9.

33. Qin, J. J., et al., *A human gut microbial gene catalogue established by metagenomic sequencing*. Nature, 2010. 464.

34. Lozupone, C. A., et al., *Diversity, stability and resilience of the human gut microbiota*. Nature, 2012. 489(7415): p. 220-230.

35. Long, T., et al., *Whole-genome sequencing identifies common-to-rare variants associated with human blood metabolites*. Nature Genetics, 2017. 49(4): p. 568-+.

36. Chong, J., et al., *MetaboAnalyst 4.0: towards more transparent and integrative metabolomics analysis*. Nucleic Acids Research, 2018. 46(W1): p. W486-W494.

37. Lopes, C. T., et al., *Cytoscape Web: an interactive web-based network browser*. Bioinformatics, 2010. 26(18): p. 2347-2348.

38. Langille, M. G., et al., *Predictive functional profiling of microbial communities using 16S rRNA marker gene sequences*. Nature Biotechnology, 2013. 31(9): p. 814-+.

39. Abubucker, S., et al., *Metabolic reconstruction for metagenomic data and its application to the human microbiome*. Plos Computational Biology, 2012. 8(6): p. 17.

40. Segata, N., et al., *Metagenomic biomarker discovery and explanation*. Genome Biology, 2011. 12(6): p. 18.

41. Yap, I. K. S., et al., *Metabonomic and microbiological analysis of the dynamic effect of vancomycin-induced gut microbiota modification in the mouse*. Journal of Proteome Research, 2008. 7(9): p. 3718-3728.

42. Adams, J. B., et al., *Nutritional and metabolic status of children with autism vs. neurotypical children, and the association with autism severity*. Nutrition & Metabolism, 2011. 8: p. 32.

43. Bak, L. K., A. Schousboe, and H. S. Waagepetersen, *The glutamate/GABA-glutamine cycle: aspects of transport, neurotransmitter homeostasis and ammonia transfer*. Journal of Neurochemistry, 2006. 98(3): p. 641-653.

44. Brown, M. S., et al., *Increased glutamate concentration in the auditory cortex of persons with autism and first-degree relatives: A 1H-MRS study*. Autism Research, 2013. 6(1): p. 1-10.

45. Stocker, R., A. N. Glazer, and B. N. Ames, *Antioxidant activity of albumin-bound bilirubin*. Proceedings of the National Academy of Sciences of the United States of America, 1987. 84(16): p. 5918-5922.

46. Stocker, R., et al., *Antioxidant activities of bile-pigments—Biliverdin and bilirubin*. Methods in Enzymology, 1990. 186: p. 301-309.

47. Frustaci, A., et al., *Oxidative stress-related biomarkers in autism: Systematic review and meta-analyses*. Free Radical Biology and Medicine, 2012. 52(10): p. 2128-2141.

48. Chauhan, A., et al., *Increased oxidative stress and inflammation in autism*. Journal of Neurochemistry, 2006. 98: p. 29-29.

49. Rose, S., et al., *Evidence of oxidative damage and inflammation associated with low glutathione redox status in the autism brain*. Translational Psychiatry, 2012. 2.

50. Wang, W. W., et al., *Glycine metabolism in animals and humans: implications for nutrition and health*. Amino Acids, 2013. 45(3): p. 463-477.

51. Tsai, G. C., et al., *Glycine transporter I inhibitor, N-methylglycine (Sarcosine), added to antipsychotics for the treatment of schizophrenia*. Biological Psychiatry, 2004. 55(5): p. 452-456.

52. Bogan, K. L. and C. Brenner, *Nicotinic acid nicotinamide and nicotinamide riboside: A molecular evaluation of NAD(+) precursor vitamins in human nutrition, in Annual Review of Nutrition*. 2008, Annual Reviews: Palo Alto. p. 115-130.

53. Chi, Y. L. and A. A. Sauve, *Nicotinamide riboside, a trace nutrient in foods, is a Vitamin B3 with effects on energy metabolism and neuroprotection*. Current Opinion in Clinical Nutrition and Metabolic Care, 2013. 16(6): p. 657-661.

54. Freedenfeld, S. H., et al., *Biochemical effects of ribose and NADH therapy in children with autism*. Autism Insights, 2011. 2011(3): p. 3-13.

55. Hou, Y. J., et al., *NAD(+) supplementation normalizes key Alzheimer's features and DNA damage responses in a new AD mouse model with introduced DNA repair deficiency*. Proceedings of the National Academy of Sciences of the United States of America, 2018. 115(8): p. E1876-E1885.

56. Zhang, L. S. and S. S. Davies, *Microbial metabolism of dietary components to bioactive metabolites: opportunities for new therapeutic interventions*. Genome Medicine, 2016. 8.

57. Burke, J. J., J. N. Siedow, and D. E. Moreland, *Succinate-dehydrogenase—A partial-purification from mung bean hypocotyls and soybean cotyledons*. Plant Physiology, 1982. 70(6): p. 1577-1581.

58. Haglund, S., et al., *The Role of Inosine-5'-Monophosphate Dehydrogenase in Thiopurine Metabolism in Patients With Inflammatory Bowel Disease*. Therapeutic Drug Monitoring, 2011. 33(2): p. 200-208.

59. Amelio, I., et al., *Serine and glycine metabolism in cancer*. Trends in Biochemical Sciences, 2014. 39(4): p. 191-198.

60. Droge, W. and R. Breitkreutz, *Glutathione and immune function*. Proceedings of the Nutrition Society, 2000. 59(4): p. 595-600.

61. James, S. J., et al., *Metabolic endophenotype and related genotypes are associated with oxidative stress in children with autism*. American Journal of Medical Genetics Part B-Neuropsychiatric Genetics, 2006. 141B(8): p. 947-956.

62. Coelho, A. I., et al., *Sweet and sour an update on classic galactosemia*. Journal of Inherited Metabolic Disease, 2017. 40(3): p. 325-342.

63. Mu, C. L., et al., *Metabolic Framework for the Improvement of Autism Spectrum Disorders by a Modified Ketogenic Diet: A Pilot Study*. Journal of Proteome Research, 2020. 19(1): p. 382-390.

64. Watanabe, H., et al., *p-Cresyl sulfate causes renal tubular cell damage by inducing oxidative stress by activation of NADPH oxidase*. Kidney International, 2013. 83(4): p. 582-592.

65. Needham, B., Mazmanian, S., Conrad, M., Rao S., and Campbell, S. *Elevation of a Putative Bacterial Metabolite in a Pediatric ASD Population. in the International Society for Autism Research (INSAR) conference*. 2018. Rotterdam, Netherlands.

66. Tomova, A., et al., *Gastrointestinal microbiota in children with autism in Slovakia*. Physiol Behav, 2015. 138.

67. Finegold, S. M., *State of the art; microbiology in health and disease. Intestinal bacterial flora in autism*. Anaerobe, 2011. 17(6): p. 367-368.

68. Clayton, T. A., et al., *Pharmacometabonomic identification of a significant host-microbiome metabolic interaction affecting human drug metabolism*. Proceedings of the National Academy of Sciences of the United States of America, 2009. 106(34): p. 14728-14733.

What is claimed is:

1. A method of treating Autism Spectrum Disorder (ASD) in a subject diagnosed with a gastrointestinal (GI) problem, the method comprising:

(a) measuring or having measured a level of each metabolite in a selected combination of at least two metabolites in a biological sample obtained from the subject, wherein the at least two metabolites in combination are selected from the group consisting of tyramine O-sulfate and inosine 5'-monophosphate (IMP); IMP and iminodiacetate (IDA); IMP and methylsuccinate; nicotinamide riboside and sphingomyelin (d18:2/23:0, d18:1/23:1, d17:1/24:1); IMP and 1-stearoyl-GPS (18:0); nicotinamide riboside and bilirubin; IMP and sarcosine; IMP and leucylglycine; iminodiacetate (IDA) and 1-linoleoyl-2-arachidonoyl-GPC (18:2/20:4n6); galactonate and 10-undecenoate (11:1n1); nicotinamide riboside and tartarate; IMP and caprylate (8:0); nicotinamide riboside and inosine 5'-monophosphate (IMP); inosine 5'-monophosphate (IMP) and 1-(1-enyl-oleoyl)-GPE (P-18:1); 3-phosphoglycerate and glycerophosphoethanolamine; 3-phosphoglycerate and 1-oleoyl-GPS (18:1); nicotinamide riboside and biliverdin; IMP and 1-stearoyl-GPI (18:0); IMP and 1-arachidonoyl-GPI (20:4); carnitine and 2'-deoxyadenosine; 1-(1-enyl-oleoyl)-GPE (P-18:1) and hydroxyproline; adenine and N-stearoyl-sphingosine (d18:1/18:0);

(b) comparing the measured level of each metabolite in the selected combination against a database of control metabolite level for each metabolite, wherein the control level for each metabolite is determined by measuring a metabolite level of in control typically developing (TD) subjects with no history of bearing a child with ASD, wherein the database is stored on a computer system and wherein the comparing comprises calculating Type I (FPR; false positive rate) and Type II (FNR; false negative rate) errors for the selected combination of metabolites using FDA or logistic regression;

(c) indicating an ASD diagnosis when, for the selected combination, the Type I error is below 10%, and a Type II error is 10%; and (d) administering a medical, behavioral, or nutritional treatment to the subject identified as having ASD, wherein the treatment comprises administering to the subject:

(i) a behavioral management therapy, a cognitive behavior therapy, an early intervention, an educational and school-based therapy, a joint attention therapy, an occupational therapy, a parent-mediated therapy, a physical therapy, social skills train-
ing, or a speech-language therapy;
    (ii) a medication selected from an antipsychotic
    drug, a selective serotonin re-uptake inhibitor
    (SSRI), a tricyclic, a psychoactive or anti-psy-
    chotic medication, a stimulant, an anti-anxiety
    medication, or an anticonvulsant;
    (iii) a nutritional supplementation with one or more
    of the metabolites of step (a) identified as having
    a Type I error of below 10%, and a Type II error
    of below 10%; or
    (iv) a composition comprising fecal microbiota from
    a healthy neurotypical human donor.
  2. The method of claim 1, further comprising preparing a
sample extract from the biological sample using Ultrahigh
Performance Liquid Chromatography-Tandem Mass Spec-
troscopy (UPLC-MS/MS) to obtain the levels of the at least
two metabolites.
  3. The method of claim 2, wherein the level of a metabo-
lite is measured using:
    i. reverse phase chromatography positive ionization meth-
    ods optimized for hydrophilic compounds (LC/MS Pos
    Polar);
    ii. reverse phase chromatography positive ionization
    methods optimized for hydrophobic compounds (LC/
    MS Pos Lipid);
    iii. reverse phase chromatography with negative ioniza-
    tion conditions (LC/MS Neg); or
    iv. a HILIC chromatography method coupled to negative
    (LC/MS Polar).
  4. The method of claim 2, wherein the level of a metabo-
lite is calculated from a peak area and standard calibration
curve obtained for the metabolite using UPLC-MS/MS.
  5. The method of claim 4, wherein measuring further
comprises identifying each metabolite by automated com-
parison of ion features in the sample extract to a reference
library of chemical standard entries that included retention
time, molecular weight (m/z), preferred adducts, and in-
source fragments as well as associated MS spectra.
  6. The method of claim 1, wherein the database of
metabolite control measured levels are measured in biologi-
cal samples obtained from typically developing (TD) indi-
viduals with no GI problems.
  7. The method of claim 1, wherein the biological sample
is blood or blood plasma.
  8. The method of claim 7, wherein the at least two
metabolites in combination are selected from the group
consisting of tyramine O-sulfate and inosine 5'-monophos-
phate; inosine 5'-monophosphate (IMP) and iminodiacetate
(IDA); IMP and sarcosine; IMP and methylsuccinate; nico-
tinamide riboside and sphingomyelin (d18:2/23:0, d18:1/23:
1, d17:1/24:1); IMP and caprylate (8:0); IMP and 1-stearoyl-
GPS (18:0); nicotinamide riboside and bilirubin; IMP and
sarcosine; IMP and leucylglycine; iminodiacetate (IDA) and
1-linoleoyl-2-arachidonoyl-GPC (18:2/20:4n6); galactonate
and 10-undecenoate (11:1n1); nicotinamide riboside and
tartarate; nicotinamide riboside and inosine 5'-monophos-
phate (IMP); inosine 5'-monophosphate (IMP) and 1-(1-
enyl-oleoyl)-GPE (P-18:1); 3-phosphoglycerate and glyc-
erophosphoethanolamine; 3-phosphoglycerate and 1-oleoyl-
GPS (18:1); nicotinamide riboside and biliverdin; IMP and
1-stearoyl-GPI (18:0); and IMP and 1-arachidonoyl-GPI
(20:4).
  9. The method of claim 1, wherein the biological sample
is a fecal sample.
  10. The method of claim 9, wherein each two metabolite
in a selected combination of at least two metabolites are selected from the group consisting of carnitine and 2'-de-
oxyadenosine; 2'-deoxyadenosine and 3-hydroxy-3-methyl-
glutarate; 1-(1-enyl-oleoyl)-GPE (P-18:1) and hydroxypro-
line; and adenine and N-stearoyl-sphingosine (d18:1/18:0).
  11. A method of treating Autism Spectrum Disorder
(ASD) in a subject diagnosed with a gastrointestinal (GI)
problem, the method comprising:
    (a) measuring or having measured a level of each metabo-
    lite in a selected combination of three metabolites in a
    biological sample obtained from the subject, wherein
    the three metabolites are selected from the group con-
    sisting of sarcosine, tyramine O-sulfate, and inosine
    5'-monophosphate; IMP, iminodiacetate (IDA), and
    tyramine O-sulfate; IMP, caproate (6:0), and tyramine
    O-sulfate; heptanoate (7:0), biliverdin, and indolepro-
    pionate; IMP, heptanoate (7:0), and biliverdin; IMP,
    picolinate, and tyramine O-sulfate; IMP, heptanoate
    (7:0), and tyramine O-sulfate; IMP, 1-oleoyl-GPS (18:
    1), and creatine; caprylate (8:0), 1-palmitoyl-GPI (16:
    0), and 3-phosphoglycerate; and IMP, azelate (nonane-
    dioate; C9), and biliverdin; indole, hydroxyproline, and
    2'-deoxyadenosine; N-stearoyl-sphingosine (d18:1/18:
    0), delta-tocopherol, and diaminopimelate; galactonate,
    N-acetylsphingosine, and adenine; carnitine,
    N-stearoyl-sphingosine (d18:1/18:0), and adenine; imi-
    dazole propionate, N-acetylsphingosine, and adenine;
    (b) administering a medical, behavioral, or nutritional
    treatment to the subject identified as a candidate for
    treatment of ASD with GI, wherein the treatment
    comprises administering to the subject:
    (i) a behavioral management therapy, a cognitive behavior
    therapy, an early intervention, an educational and
    school-based therapy, a joint attention therapy, an occu-
    pational therapy, a parent-mediated therapy, a physical
    therapy, social skills training, or a speech-language
    therapy;
    (ii) a medication selected from an antipsychotic drug, a
    selective serotonin re-uptake inhibitor (SSRI), a tricy-
    clic, a psychoactive or anti-psychotic medication, a
    stimulant, an anti-anxiety medication, or an anticon-
    vulsant;
    (iii) a nutritional supplementation with one or more of the
    metabolites of step (a) identified as having a Type I
    error of below 10%, and a Type II error of below 10%;
    or
    (iv) a composition comprising fecal microbiota from a
    healthy neurotypical human donor.
  12. A method of treating Autism Spectrum Disorder
(ASD) in a subject diagnosed with a gastrointestinal (GI)
problem, the method comprising:
    (a) measuring or having measured a level of each metabo-
    lite in a selected combination of four metabolites in a
    biological sample obtained from the subject, wherein
    the four metabolites are selected from the group con-
    sisting of sarcosine, tyramine O-sulfate, inosine
    5'-monophosphate, and arachidonate (20:4n6); IMP,
    picolinate, tyramine O-sulfate, and arachidonate (20:
    4n6); IMP, galactonate, picolinate, and tyramine O-sul-
    fate; 3-phosphoglycerate, caproate (6:0), picolinate,
    and tyramine O-sulfate; IMP, iminodiacetate (IDA),
    tyramine O-sulfate, and arachidonate (20:4n6); IMP,
    iminodiacetate (IDA), leucylglycine, and tyramine
    O-sulfate; IMP, 2-aminophenol sulfate, picolinate, and
    tyramine O-sulfate; iminodiacetate (IDA), 3-phospho-
    glycerate, glycerophosphoethanolamine, and tyramine
    O-sulfate; iminodiacetate (IDA), 3-phosphoglycerate,
    tyramine O-sulfate, and arachidonate (20:4n6); IMP, sarcosine, sphingomyelin (d18:2/23:0, d18:1/23:1, d17:1/24:1), and tyramine O-sulfate; indole, 10-nonadecenoate (19:1n9), adenine, and theobromine; indole, adenine, biliverdin, and theobromine;

(b) administering a medical, behavioral, or nutritional treatment to the subject identified as a candidate for treatment of ASD with GI, wherein the treatment comprises administering to the subject:

(i) a behavioral management therapy, a cognitive behavior therapy, an early intervention, an educational and school-based therapy, a joint attention therapy, an occupational therapy, a parent-mediated therapy, a physical therapy, social skills training, or a speech-language therapy;

(ii) a medication selected from an antipsychotic drug, a selective serotonin re-uptake inhibitor (SSRI), a tricyclic, a psychoactive or anti-psychotic medication, a stimulant, an anti-anxiety medication, or an anticonvulsant;

(iii) a nutritional supplementation with one or more of the metabolites of step (a) identified as having a Type I error of below 10%, and a Type II error of below 10%; or (iv) a composition comprising fecal microbiota from a healthy neurotypical human donor.

13. A method of treating Autism Spectrum Disorder (ASD) in a subject diagnosed with a gastrointestinal (GI) problem, the method comprising:

(a) measuring or having measured a level of each metabolite in a selected combination of five metabolites in a biological sample obtained from the subject, wherein the five metabolites are selected from the group consisting of IMP, galactonate, picolinate, tyramine O-sulfate, and arachidonate (20:4n6); IMP, 1-stearoyl-GPS (18:0), picolinate, creatine, and tyramine O-sulfate; IMP, iminodiacetate (IDA), biliverdin, arachidonate (20:4n6), and 2-oxindole-3-acetate; IMP, picolinate, gamma-glutamylhistidine, tyramine O-sulfate, and arachidonate (20:4n6); IMP, iminodiacetate (IDA), leucylglycine, 1-palmitoyl-GPI (16:0), and tyramine O-sulfate; IMP, citrate, sphingomyelin (d18:2/23:0, d18:1/23:1, d17:1/24:1), fructose, and arachidonate (20:4n6); IMP, picolinate, 9,10-DiHOME, tyramine O-sulfate, and arachidonate (20:4n6); IMP, 2-methylserine, picolinate, tyramine O-sulfate, and arachidonate (20:4n6); IMP, caproate (6:0), tyramine O-sulfate, arachidonate (20:4n6), and 1-linoleoyl-2-arachidonoyl-GPC (18:2/20:4n6); IMP, bilirubin, sphingomyelin (d18:2/23:0, d18:1/23:1,d17:1/24:1), arachidonate (20:4n6), and tartarate; imidazole propionate, hydroxyproline, theobromine, 2-hydroxy-3-methylvalerate, and indole;

(b) administering a medical, behavioral, or nutritional treatment to the subject identified as a candidate for treatment of ASD with GI, wherein the treatment comprises administering to the subject:

(i) a behavioral management therapy, a cognitive behavior therapy, an early intervention, an educational and school-based therapy, a joint attention therapy, an occupational therapy, a parent-mediated therapy, a physical therapy, social skills training, or a speech-language therapy;

(ii) a medication selected from an antipsychotic drug, a selective serotonin re-uptake inhibitor (SSRI), a tricyclic, a psychoactive or anti-psychotic medication, a stimulant, an anti-anxiety medication, or an anticonvulsant;

(iii) a nutritional supplementation with one or more of the metabolites of step (a) identified as having a Type I error of below 10%, and a Type II error of below 10%; or (iv) a composition comprising fecal microbiota from a healthy neurotypical human donor.

14. A method of treating Autism Spectrum Disorder (ASD) in a subject diagnosed with a gastrointestinal (GI) problem, the method comprising: administering to the subject a medical, behavioral, nutritional treatment, or a composition comprising fecal microbiota from healthy neurotypical human, wherein the subject has been determined as having ASD with GI disorder by, for a selected combination of at least two metabolites, a Type I error of below 10%, and a Type II error of below 10% for a level of each two metabolite in a selected combination of at least two metabolites in a biological sample obtained from the subject, wherein two metabolites in combination are selected from the group consisting of tyramine O-sulfate and inosine 5'-monophosphate (IMP) IMP and iminodiacetate (IDA); IMP and sarcosine, IMP and methylsuccinate; nicotinamide riboside and sphingomyelin (d18:2/23:0, d18:1/23:1, d17:1/24:1); IMP and 1-stearoyl-GPS (18:0); nicotinamide riboside and bilirubin; IMP and sarcosine; IMP and leucylglycine; iminodiacetate (IDA) and 1-linoleoyl-2-arachidonoyl-GPC (18:2/20:4n6); galactonate and 10-undecenoate (11:1n1); nicotinamide riboside and tartarate; IMP and caprylate (8:0); nicotinamide riboside and inosine 5'-monophosphate (IMP); inosine 5'-monophosphate (IMP) and 1-(1-enyl-oleoyl)-GPE (P-18:1); 3-phosphoglycerate and glycerophosphoethanolamine; 3-phosphoglycerate and 1-oleoyl-GPS (18:1); nicotinamide riboside and biliverdin; IMP and 1-stearoyl-GPI (18:0), and IMP and 1-arachidonoyl-GPI (20:4), wherein the treatment comprises administering to the subject:

(a) a behavioral management therapy, a cognitive behavior therapy, an early intervention, an educational and school-based therapy, a joint attention therapy, an occupational therapy, a parent-mediated therapy, a physical therapy, social skills training, or a speech-language therapy;

(b) a medication selected from an antipsychotic drug, a selective serotonin re-uptake inhibitor (SSRI), a tricyclic, a psychoactive or anti-psychotic medication, a stimulant, an anti-anxiety medication, or an anticonvulsant;

(c) a nutritional supplementation with one or more of the metabolites identified as having a Type I error of below 10%, and a Type II error of below 10% for a level of each of the two metabolite in the combination; or (d) a composition comprising fecal microbiota from a healthy neurotypical human donor.

15. A method of classifying a subject as a candidate for treatment of Autism Spectrum Disorder (ASD) with a gastrointestinal (GI) disorder, the method comprising:

a) measuring a level of each of two metabolite in a selected combination of at least two metabolites in the biological sample using ultrahigh performance liquid chromatography-tandem mass spectroscopy (UPLC-MS/MS), wherein the at least two metabolites in combination are selected from the group consisting of tyramine O-sulfate and inosine 5'-monophosphate (IMP) IMP and iminodiacetate (IDA); IMP and sarcosine, IMP and methylsuccinate; nicotinamide riboside and sphingomyelin (d18:2/23:0, d18:1/23:1, d17:1/24:1); IMP and 1-stearoyl-GPS (18:0); nicotinamide riboside and bilirubin; IMP and sarcosine; IMP and leucylglycine; iminodiacetate (IDA) and 1-linoleoyl-2-arachidonoyl-GPC (18:2/20:4n6); galactonate and 10-undecenoate (11:1n1); nicotinamide riboside and tartarate; IMP and caprylate (8:0); nicotinamide riboside and inosine 5'-monophosphate (IMP); inosine 5'-monophosphate (IMP) and 1-(1-enyl-oleoyl)-GPE (P-18:1); 3-phosphoglycerate and glycerophosphoethanolamine; 3-phosphoglycerate and 1-oleoyl-GPS (18:1); nicotinamide riboside and biliverdin; IMP and 1-stearoyl-GPI (18:0); IMP and 1-arachidonoyl-GPI (20:4); carnitine and 2'-deoxyadenosine; 1-(1-enyl-oleoyl)-GPE (P-18:1) and hydroxyproline; adenine and N-stearoyl-sphingosine (d18:1/18:0);

b) generating, by a processor, a Type I (FPR; false positive rate) and a Type II (FNR; false negative rate) error for the each of the metabolite in the selected combination of metabolites using Fisher discriminant analysis (FDA) or logistic regression by comparing the measured level of each metabolite in the selected combination against a model comprising a database of control metabolite level determined by measuring a metabolite level in control typically developing (TD) subjects with no history of bearing a child with ASD, wherein the model has a classification accuracy of at least 0.05 and misclassification error of less than 0.05;

c) classifying the subject as a candidate for treatment of ASD with GI when, for the selected combination, the Type I error is below 10%, and a Type II error is below 10%; and d) administering a medical, behavioral, or nutritional treatment to the subject identified as a candidate for treatment of ASD with GI, wherein the treatment comprises administering to the subject:

(i) a behavioral management therapy, a cognitive behavior therapy, an early intervention, an educational and school-based therapy, a joint attention therapy, an occupational therapy, a parent-mediated therapy, a physical therapy, social skills training, or a speech-language therapy;

(ii) a medication selected from an antipsychotic drug, a selective serotonin re-uptake inhibitor (SSRI), a tricyclic, a psychoactive or anti-psychotic medication, a stimulant, an anti-anxiety medication, or an anti-convulsant;

(iii) a nutritional supplementation with one or more of the metabolites of step (a) identified as having a Type I error of below 10%, and a Type II error of below 10%; or (iv) a composition comprising fecal microbiota from a healthy neurotypical human donor.

* * * * *